(12) United States Patent
Cheng et al.

(10) Patent No.: US 9,043,995 B2
(45) Date of Patent: Jun. 2, 2015

(54) TRANSGENIC FISH AND USES THEREOF

(71) Applicant: CITY UNIVERSITY OF HONG KONG, Kowloon (HK)

(72) Inventors: Shuk Han Cheng, Kowloon (HK); Xue Ping Chen, Hunan Province (CN)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 0 days.

(21) Appl. No.: 13/769,533

(22) Filed: Feb. 18, 2013

(65) Prior Publication Data

US 2013/0152222 A1    Jun. 13, 2013

Related U.S. Application Data

(62) Division of application No. 12/730,956, filed on Mar. 24, 2010, now Pat. No. 8,395,018.

(51) Int. Cl.
| | |
|---|---|
| C07H 21/02 | (2006.01) |
| A01K 15/00 | (2006.01) |
| A01K 67/027 | (2006.01) |
| C12N 15/63 | (2006.01) |
| C12N 15/85 | (2006.01) |

(52) U.S. Cl.
CPC ............ *A01K 67/0275* (2013.01); *C12N 15/63* (2013.01); *A01K 2217/05* (2013.01); *A01K 2217/052* (2013.01); *A01K 2217/203* (2013.01); *A01K 2217/206* (2013.01); *A01K 2227/40* (2013.01); *A01K 2267/0393* (2013.01); *C12N 15/8509* (2013.01); *C12N 2800/106* (2013.01); *C12N 2830/002* (2013.01); *C12N 2830/008* (2013.01)

(58) Field of Classification Search
CPC ..... C12N 15/00; C12N 2830/00; C12N 15/63
See application file for complete search history.

(56) References Cited

U.S. PATENT DOCUMENTS

| 6,759,568 B2 | 7/2004 | Yamashita |
| 2006/0101528 A1 | 5/2006 | Demeneix et al. |

FOREIGN PATENT DOCUMENTS

| CN | 1904048 A | 1/2007 |
| WO | 03/102176 A1 | 12/2003 |
| WO | 2004/023867 A2 | 3/2004 |
| WO | 2007/113204 A2 | 10/2007 |

OTHER PUBLICATIONS

Partial European Search Report issued in European application No. EP11305315, completed Aug. 1, 2011.
Database EMBL [Online], "*Oryzias melastigma* choriogenin H gene, 3' UTR and flanking region," retrieved from EBI accession No. EM_OV:DQ778335 (Jul. 31, 2006).
Scholz et al., "Analysis of estrogenic effects by quantification of green fluorescent protein in juvenile fish of a transgenic medaka," *Environmental Toxicology and Chemistry*, 24(10):2553-2561 (2005).
Databse EMBL [Online], "*Oryzias melastigma* choriogenin H gene, complete cds," retrieved from Genbank accession No. EF392365 (Feb. 11, 2007).
Pati, 2004, Cancer Res, 64:5608-5616.
Cok, 2001, Jour Biol Chem, 276:23179-23185.
Jordan BioEssays, 1988, 8:140-145.
Kurauchi, 2005, Environ Sci Technol, 39:2762-2768.
Ueno, 2004, Mechanisms of Development, 121:803-815.
Zeng, 2005, Environ Sci Technol, 39:9001-9008.
Chen, 2008, Ecotoxicology and Environmental Safety, 71:200-208.
Clontech, pEGFP-1 Vector Information Sheet, Oct. 3, 2002, Catalog #6086-1, pp. 1-3.

*Primary Examiner* — Valarie Bertoglio
(74) *Attorney, Agent, or Firm* — Heslin Rothenberg Farley & Mesiti P.C.; Andrew K. Gonsalves, Esq.

(57) ABSTRACT

The present invention relates to a transgenic fish having at least one genomically integrated expression cassette containing a 5'-regulatory nucleotide sequence responsive to hormones, particularly estrogenic hormones, connected in a functional manner upstream of a nucleotide sequence encoding a reporter protein. The present invention further relates to methods of using the transgenic fish for various purposes, including, for example: (1) identifying estrogenic endocrine disruptors; (2) monitoring estrogen-like activity of test samples; (3) identifying anti-estrogenic endocrine disruptors; and (4) investigating the effects of endocrine disruptors on liver regeneration. Expression cassettes, host cells, and transgenic cells of aquatic animals are also disclosed.

20 Claims, 15 Drawing Sheets dph: days post hatching

*p<0.05

*p<0.05

*p<0.05

SEQUENCE LISTING

```
<160> NUMBER OF SEQ ID NOS: 27

<210> SEQ ID NO 1
<211> LENGTH: 8455
<212> TYPE: DNA
<213> ORGANISM: Oryzias melastigma

<400> SEQUENCE: 1
gaattcacta gtgattacta tagggcacgc gtggtcgacg gcccgggctg gtatcgtgag      60
ccatgtatcg cgtatcgtat cgtatcgtga ggtacccagt gattcccagc cctaataatt     120
atggctaaat actatatatg tagaaatcta actgttgtta aaaaagccag agtttttta      180 atcttcacaa agaaattgtt ttgcaaatta atgaaaatcc aatgcaaaag ctgttaggac     240
agtcgaagcc tggacttgtt tggcatcata ttttattatt attattatga ttcctttctt     300
ttgttacccc ctggcaagtt catatcaatt attctgtaat tctcggtatt ggatcattta     360
```

```
ttctttatat gtgctacatt ttgacaaaaa aaaatcgata ttatgaacat tatacccttta    420 caaatctgtt ttacacatct cctgatttta caaagaaaat attatactaa ttaaactaaa    480
tgtagtgata aagctccaaa tttatttggt ttattttccc aaatccatca ttatttacaa    540
tatttcattt tgtccaaaca caaaaataaa gtttcacaac tagatagatt atcatgattt    600
tacctctgtt ttttttttt caatttttt cctataataa ctacccaggc gtttatcttg    660
aaaaattagt tattgttctg tgttctgttc tacataagag gattaaggcc atggaggaat    720
taaacgggta tggataattc taagtttaaa gtcagaattc tgactttttt ttcctcggaa    780
ttctgacttt tttcccagaa ttctggcctt ttatatattt tttagaaaga tttagaaaca    840
tattaaattt cttactgcta catttcatct cgtacctcca aaacccaaca tattttgtct    900
ataaaggttg agcttaaaaa tatatatttt ttcaattaaa agaaaataac tgaaaaactg    960
gaatttaatc ttaaaactac caagaagtta tctatttaat cattatgttt acattcaagt   1020
cgtcttaggg ccacaaggta cttagccttt gctgttattt acaaagacga caatttaagt   1080
gtatgaagtg atctttataa atcagtcaaa tatattttt taaatgcact cattcccctt   1140
tggcagcaag ttgtggcgaa aatcctttat aatcttcaaa ttacaagtat gaacaatatt   1200
gtttccttta aaacaattag cagtctaatc attttctata atatgaaagt tcatatctta   1260
tgtagttgaa aagtgtgcta tttttgtaat tgtatttctt tttatatatt ttgcatttag   1320
tgaactactg cattaactag cttgcaatac ttttcgcatt gtgtctctca taaaaaatat   1380
agatatggtt atttaaaaaa atgcgtttac tcttaattgt tgccttttgg agtaaaattt   1440
tatgcttttg tctgtattgc cttttgaca ttcagaagag gatgcttctg tatgacggcg   1500
tattaaggcc ttgagggtat catgtctgtg gtgtgactga atgattacat tgatgctgtt   1560
ttacactttg aaaatcacca tttgaaacca agttttgtct cacaattgca tcaaacagaa   1620
aaaaaaccat caaagcaagc taattgaatg ttgattggtt taatccaagt cattacagtt   1680
tattccacct gagtctagat gattctaaca gattgtttga ctgttgtcaa aatgatccta   1740
catgaatgca agtccaaagc aagataaatg ctctttctct tcaaatgatt tgacattaat   1800
cttcccctaa aatttattat tggtcataat attgataaat ctttgtttcg tgatgcatga   1860
gaccttatca cctaattttg cagtaaagag agtcaactaa aaaatttct gacactcttt   1920 tgttacttat tatctcatga aatcctttgt actgttttgc cttggggttt ttattgacta   1980
acatctcttt aatcacacat aattcaactg ttcataattc caaatatgtt ttagcttttg   2040
ttataacgat ttaagttaca gcaatgtgtt ttatttttt ctgtatttaa ctgaactatg   2100
ttgcccttat aaacagttac atgtatgtaa taggagtggc ctgatattgc cacacacccc   2160
tcatcggatc ctatgtcatg gacaaatagc tccactatat ggtcaaacat aagtataact   2220
taagaaagta acagaaaaat ttaatttaaa aaagttttt tttttttttt gtcttttcca   2280
tttctttatt ttatttattt aaatccaaaa aaagtcaaat cctttacttc tcggcacata   2340 attttttcaaa caatctttt aaataaaatt attaattaaa gcaaatattc attcacaaaa   2400 aaaaacttt agagtttgaa aaatgcgaat ttaaagttgt attattataa tcaatattga   2460
tttaagttta caaatagatt taaaaaaaaa atggaaatct gctatgtttc cttgacagcc   2520
ttcaaaagtt tccttctgga aaagttaaac tgttgttttg tgacggtgtt ttttttaaa   2580 cgctttgtct ggatcaatta aagcatagtt ttttcacatt tgcggttttt cacggagaga   2640
ggaagtttcc tttattgtgt atcctgccct gagtaccagt gacattagag cctgtaacgt   2700
```

```
gtcaaataaa gtgacacagt tggccagatc taaagtctcg gatgttgtgt tctggtcaaa   2760
taaacatatg acaatgaata aaagttgagg tcacatggac attttgaaaa gggcttttat   2820
gacctagagt ttgatttgta gataaacccc tttatgtcaa actgtcatca aacacaaccc   2880
tgatccaaca gcgttacccc ttagctatca cagttcactt tgtaaatttg tcacaaaaaa   2940
tgggtcataa tcatcaaaat gaattataat ttctaagaaa ttatagcatt tagatattgc   3000
acctttttaa acacctcaaa attactggtt tcttttcttt ttattattto tttagtttta   3060 agtttgtttt gaaatgatc ttaatattgc agcggagtag cacgtattta actaaaatta   3120
aaactactaa ccatgaacat ttttcagcat ttgtgtggtt tagttttgt gacatgtttg   3180 catgtagtca tattttgagt ttttgaggtg cttttttaaca gctttcagaa gcagtttaac   3240
catttaaaat taagaaaatt caagctcaga ttacacttttt catattatct tagtttgtga   3300
aaaaatagta ttataatata ttagaagact ttcttctaca caggactacc tgaggtttaa   3360
acaacacttt atcaactgag aggtagcact gaaatatgtg cgctgcaagt tatttaattg   3420
tttttttttt tttattttttt agctcttgct acctagaaac attgtaaaaa aaattactga   3480
aactttacac attaattttc tgaagacctc atcataatcc atgatgttta acgggtttga   3540
attgcactta ttttttactgc atcataatta ccacatccac tctattaaat tctattccaa   3600
taccagagtt aaggctagag tttggtacac tacgaccgat ccacagttat gcaacgtaat   3660
tctgagaaac tatgagtctc ctttattatt cctctatcaa accagtggtg aaggaagtat   3720
tttaattttt acttaaataa aacttttcaa cattaaacaa ttcaaatgtg tgtgcgtctg   3780
tctgaattca tttaattatt cgttaattga ttttctacac aattaatact tgcatatgtt   3840 ttgcttttttt taaatgctaa ctttattaca ttttctgatt ggggctaaaa atcaactgga   3900
aagaaaatgg ttttttttac acttcattat gtcctgtttg gggttgctgg agcctgtccg   3960
agttacctca ggggaaaagc cagagtgcac cctgaacatt gagaggtcac acacagacac   4020
atccatccat gttcttaacc tgctaaatcc cttattaagc atgatttgg actgtctgaa   4080 gaaaagccaa gcaagaacat gccaagtcca cgcaaagggt cccaaccat gctttcaacc   4140 aggaccagct tactgtgagg tgagaccgct aactactgca ccacagtgca gcccatattt   4200
agacttaatg caatatattg tgttttgggg aagaagctgg agagcctgga gggaaccagt   4260
gcatggggaa aacatacaaa cctcacacag caaggatcac atctgcctca gtatgtattt   4320
ttacagctta ctgtaattaa aaacagtaaa aaaaaaaaa ctaaaaaaaa aaacatcaaa   4380
ttgccacaaa aagtacatga tttaaaaaaa ggtttctgtc tacatgttta catcttaatt   4440
tgatttaaaa cactaaaaaa tacataagat tgcccccaaa aaatgcaatt ataaaaagca   4500
catgatttaa aaaaaaaaag gtatccgtac gtatttttag atcttaattt ggcttaaaca   4560
ctaaaaaata cattagattg ccaaaaaatg caattataaa tatacatgtt ttttaataaa   4620
agccatcagc tgcacatgca ttttgggaaa aaaaggttgt cttatagaaa aagtccacat   4680
ccattacaca atttaactgt ttactttgaa taaaaacaca ttactgtgct gctttattat   4740
tgctctcact ctatggggtt caaactaatg tgtatttgtc atttttgtgc tttgtttagt   4800
ggatatctaa cagtatgtca acagactgaa agggcaaaag aggtaattac ttcctaaaca   4860
gctaacatta gattgtttct gtcatggaaa atgcatgaaa acatactgca acaatttatt   4920
ttaatgttca ttaagtgcta aggttttttag gattcttgaa atcctcaaat tgatatgtta   4980
gcgacacata tttgactata atggtcttct gttatttcat tcatttatgt aacaaaaaca   5040
ataacacaaa aatgtacata acttttcatt tactcgagac ctattagtta aaaaaatgtg   5100
```

```
gaggaatgag ccttttcttt actacgtcga aatataaaat ttctgagaca taaatcaatt    5160
ataaatatac agtatatggc ctgattaaaa aaaagaaaaa aacttttcaa ctgattttgt    5220
aatgcagaaa atcatgctta gcacaaccag agcattcgcc aacatataca tttgatgtgg    5280
acatcatcct aataacctca tataaaaggt ttttttttgac caaaatgtgt acaatatgag   5340
gttttgttgc agattcaggg aaaagatcac tttgtttgtc attgcctact atcaaaacaa    5400
acatttgagg acagataagt tcgagactgc aaagaccctg aaaaggtctc catgacctgg    5460
atgtcacaaa agcctttcat tcattccaac gcaacgacct gatctggcat ttcacgcaaa    5520
ggacagaata gtccacatga attacataaa attgacttaa caaaacacac cctgaagcgt    5580
ttgtgattgg gagctacttg gtttgagagg tggagtttga agagcatcaa aggtaaagac    5640
acataaatag agcaggagag ggaaatttac acttagggac ccatcgggtc agacagctgt    5700
gggaccatgg caaggcactg gagtattacg gttttttccg cactagctct gatatgttct    5760
ttcctggcga cccaagtgga tgctcagaaa ggccccctc aagaccctaa ggttccatac     5820
cctccatact atccacagcc gaagccgcag gaccctcaac acgtttcacc gccttacaac    5880
ccagggaagc cgcagtatcc agggaagcca cagtatccag ggaagccgca gagtccacag    5940
tatcctcaga cccctcagta tcctcagacc cctcagcagc cgcagagtcc acagtatcct    6000 cagaccctc agtatcctca gaccctcag cagccgcaga gtcctcagta tcctcagtcc     6060
cctcagtatc ctcagactcc tcagtccct cagtatcctc agtccctca gtatcctcag     6120 actcctcagt atcctcagaa tcctaaggtg tatggtgatg acagttctaa gccttcaact    6180
ccgtcaaagc ctagctatcc tcagcctcag gccccccagt acccatctaa gcctcaagct    6240
ccccagctgc ctcaggcccc ccagtaccca actaagcctc aagctcccca gctgcctcaa    6300
gctccccagc tgcctcaggc cccccagtac ccaactaagc tcaagctcc tcagtatcct    6360 caagctcctc agcagcctca ggccccccag tacccaacta gcctcaagc tcctcagcag    6420 ccccaggctc cccagtaccc aactaagcct caagctcctc agtaccctca gctcctcag    6480 cagccccagg ctcccagta cccaacaaaa cctcagcagc cccagtaccc aacaaagcct    6540
cagtctcctc agtaccctca agatcctaaa atccaaaatc ctcagaatcc tcctcttcat    6600
cctccccctg ttaagagctg tgaggtgccc cgcgatgtga gagtcccatg tggagttcca    6660
gacatctctc cttctgcatg cgatgccatt gactgctgtc atgatggcca agcctgctac    6720
tttggaacag gaggtaagtg gtttctccag ctgctatgat cagaggcttt ttgtaaggtg    6780
acggctgatc gtgcaatcgt cgatcccatc tatttcttct agcaaccgtt cagtgcacca    6840
aggacggaca cttcatcgtt gtggtggcca aggatgtcac cttacccat ctcgatcttg     6900 aaactatttc acttttggga ccgggtcaag aatgtgagc tgttgactct aattcagctt     6960
tcgccatcta ctactttccc gtcactcagt gcggcactca tgtcacggta acactcagtc    7020
ttgtttatat cttatagtca taggtcaat cttttgagatt ctatccttct tattgttaaa    7080
ttttgaacca ttaaaaggaa gagcccgggg ttatagtcta tgaaaaccgg atgacatcct    7140
catatgaagt tggagttgga ccgcttggag ctattaccag agacagctct tttgagtagg    7200
tcatcatttg tgtttagtat caaacagatt tactaatgtc taactaatat ctatcagggg    7260
taaacagaat catgcacagt gtattaacac agttctttt ctcaggctcc tcttccagtg     7320
cagataccat gcaacatctg ttgaaactct ggtcgtggaa gtgctgccag tggatagtcc    7380
tctttccatt gctgagcttg gaccectcaa tgtgtacttg caaattgcca atggagtatg    7440
```

```
tcagacaaag ggctgcgacg aaggtcagtg cacggcagtc tggcacagcc agtgtgtttg    7500
tcaaacattt gaaaaagctg cctgtcgtaa cgtttgtttg ctcccacagt ggcggcagcc    7560
tacacctctt tctacacgga tgccgactat cctgtgacca aagtactgag agaaccagtc    7620
tatgtggacg ttcaaatcct tggcagaaca gatccaaatc tggttctgac tcttggacgc    7680
tgttgggcaa ccacaagccc caatgctttc agtctgcccc agtgggacat tttgattgac    7740
gggtaaaaaa aaaaaaatct accaattcat tccataaaga ccattttgt tcaaactaag     7800 ctccaaatct cacactttt agccgaatta ctaaatatct aaccaaccat tacttcttct      7860
ttaccttttt tccatccaga tgtccatatg aagatgatcg ctacctgtct gcgttggttc    7920
caatcgattc ctcctctggt ttgccattcc caactcatca cagacgcttc ttattcaaga    7980
tgtttacctt tgttgatcct cattcaatgg aaccactaag ggaaaaggtg ggtactgaat    8040
tactcaagta gaggtttaac ttggcttcta acctgtactt ttctttcagg tgtacattca    8100
ctgcagcaca gctgcatgcg ttccaggaca gggtaccagt tgtgaaccct catgcagcag    8160
aagaagtagg gggctcattt ataaccgttc acatgttttt tttgttgttg taatgaccat    8220
gtccactcat cattggccat gttttgtgtc ttttgtaga aggaagagat actgacgctg      8280
tatccattag aacggatgaa agaaaggttg tggtatcgtc tggagaagtg ctcatggtgg    8340
ccgaagctgc tggacagtct taactgtgaa ccgacagaag ctccagagtt cggaaaaaat    8400
aacataacat tatgaaaatc tgtttcatca tggttcagaa ttaaatgcat aaagt          8455

<210> SEQ ID NO 2
<211> LENGTH: 4838
<212> TYPE: DNA
<213> ORGANISM: Oryzias melastigma

<400> SEQUENCE: 2
ctcgtacctc caaacccaa catattttgt ctataaaggt tgagcttaaa aatatatatt      60
ttttcaatta aaagaaaata actgaaaaac tggaatttaa tcttaaaact accaagaagt    120
tatctattta atcattatgt ttacattcaa gtcgtcttag ggccacaagg tacttagcct    180
ttgctgttat ttacaaagac gacaatttaa gtgtatgaag tgatctttat aaatcagtca    240
aatatatttt tttaaatgca ctcattcccc tttggcagca agttgtggcg aaaatccttt    300
ataatcttca aattacaagt atgaacaata ttgtttcctt taaaacaatt agcagtctaa    360
tcattttcta taatatgaaa gttcatatct tatgtagttg aaaagtgtgc tattttttgta   420 attgtatttc ttttttatata ttttgcattt agtgaactac tgcattaact agcttgcaat  480
acttttcgca ttgtgtctct cataaaaaat atagatatgg ttatttaaaa aaatgcgttt    540
actcttaatt gttgccttt ggagtaaaat tttatgcttt tgtctgtatt gccttttga      600 cattcagaag aggatgcttc tgtatgacgg cgtattaagg ccttgagggt atcatgtctg    660
tggtgtgact gaatgattac attgatgctg ttttacactt tgaaaatcac catttgaaac    720
caagttttgt ctcacaattg catcaaacag aaaaaaaacc atcaaagcaa gctaattgaa    780
tgttgattgg tttaatccaa gtcattacag tttattccac ctgagtctag atgattctaa    840
cagattgttt gactgttgtc aaaatgatcc tacatgaatg caagtccaaa gcaagataaa    900
tgctctttct cttcaaatga tttgacatta atctttccct aaaatttatt attggtcata    960
atattgataa atctttgttt cgtgatgcat gagaccttat cacctaattt tgcagtaaag   1020
agagtcaact aaaaaatttt ctgacactct tttgttactt attatctcat gaaatccttt    1080
gtactgtttt gccttggggt ttttattgac taacatctct ttaatcacac ataattcaac    1140
```

```
tgttcataat tccaaatatg ttttagcttt tgttataacg atttaagtta cagcaatgtg    1200 ttttatttt  ttctgtattt aactgaacta tgttgccctt ataaacagtt acatgtatgt    1260
aataggagtg gcctgatatt gccacacacc cctcatcgga tgctatgtca tggacaaata    1320
gctccactat atggtcaaac ataagtataa cttaagaaag taacagaaaa atttaattta    1380
aaaaaagttt tttttttttt ttgtcttttc catttcttta ttttatttat ttaaatccaa    1440
aaaaagtcaa atcctttact tctcggcaca taattttca  aacaatcttt ttaaataaaa    1500
ttattaatta aagcaaatat tcattcacaa aaaaaaactt ttagagtttg aaaaatgcga    1560
atttaaagtt gtattattat aatcaatatt gatttaagtt tacaaataga tttaaaaaaa    1620
aaatggaaat ctgctatgtt tccttgacag ccttcaaaag tttccttctg gaaaagttaa    1680
actgttgttt tgtgacggtg tttttttta  aacgctttgt ctggatcaat taagcatag     1740 tttttttcaca tttgcggttt ttcacggaga gaggaagttt cctttattgt gtatcctgcc   1800
ctgagtacca gtgacattag agcctgtaac gtgtcaaata aagtgacaca gttggccaga   1860
tctaaagtct cggatgttgt gttctggtca aataaacata tgacaatgaa taaaagttga   1920
ggtcacatgg acattttgaa aagggctttt atgacctaga gtttgatttg tagataaacc   1980
cctttatgtc aaactgtcat caaacacaac cctgatccaa cagcgttacc ccttagctat   2040
cacagttcac tttgtaaatt tgtcacaaaa aatgggtcat aatcatcaaa atgaattata   2100
atttctaaga aattatagca tttagatatt gcacctttt  aaacacctca aaattactgg   2160
tttcttttct ttttattatt tctttagttt taagtttgtt ttgaaaatga tcttaatatt    2220
gcagcggagt agcacgtatt taactaaaat taaaactact aaccatgaac attttcagc    2280 atttgtgtgg tttagttttt gtgacatgtt tgcatgtagt catattttga gttttttgagg   2340 tgcttttta  cagctttcag aagcagttta accatttaaa attaagaaaa ttcaagctca    2400
gattacactt ttcatattat cttagtttgt gaaaaaatag tattataata tattagaaga    2460 cttctcttcta cacaggacta cctgaggttt aaacaacact ttatcaactg agaggtagca   2520
ctgaaatatg tgcgctgcaa gttatttaat tgttttttt  tttttattt  ttagctcttg    2580 ctacctagaa acattgtaaa aaaaattact gaaactttac acattaattt tctgaagacc   2640
tcatcataat ccatgatgtt taacgggttt gaattgcact tattttact  gcatcataat    2700 taccacatcc actctattaa attctattcc aataccagag ttaaggctag agtttggtac   2760
actacgaccg atccacagtt atgcaacgta attctgagaa actatgagtc tcctttatta   2820
ttcctctatc aaaccagtgg tgaaggaagt attttaattt ttacttaaat aaaacttttc   2880
aacattaaac aattcaaatg tgtgtgcgtc tgtctgaatt catttaatta ttcgttaatt   2940 gatttctac  acaattaata cttgcatatg ttttgctttt tttaaatgct aactttatta   3000
cattttctga ttggggctaa aaatcaactg gaaagaaaat ggttttttt  acacttcatt   3060 atgtcctgtt tggggttgct ggagcctgtc cgagttacct caggggaaaa gccagagtgc   3120
accctgaaca ttgagaggtc acacacagac acatccatcc atgttcttaa cctgctaaat   3180
cccttattaa gcatgatttt ggactgtctg aagaaaagcc aagcaagaac atgccaagtc   3240
cacgcaaaag ggtcccaacc atgctttcaa ccaggaccag cttactgtga ggtgagaccg   3300
ctaactactg caccacagtg cagcccatat ttagacttaa tgcaatatat tgtgttttgg   3360
ggaagaagct ggagagcctg gagggaacca gtgcatgggg aaaacataca aacctcacac   3420
agcaaggatc acatctgcct cagtatgtat ttttacagct tactgtaatt aaaaacagta   3480
```

```
aaaaaaaaaa aactaaaaaa aaaaacatca aattgccaca aaaagtacat gatttaaaaa   3540
aaggtttctg tctacatgtt tacatcttaa tttgatttaa aacactaaaa aatacataag   3600 attgcccca aaaaatgcaa ttataaaaag cacatgattt aaaaaaaaaa aggtatccgt    3660
acgtattttt agatcttaat ttggcttaaa cactaaaaaa tacattagat tgccaaaaaa   3720
tgcaattata aatatacatg ttttttaata aaagccatca gctgcacatg cattttggga   3780 aaaaaggtt gtcttataga aaagtccac atccattaca caatttaact gtttactttg     3840
aataaaaaca cattactgtg ctgctttatt attgctctca ctctatgggg ttcaaactaa   3900
tgtgtatttg tcattttgt gctttgttta gtggatatct aacagtatgt caacagactg    3960
aaagggcaaa agaggtaatt acttcctaaa cagctaacat tagattgttt ctgtcatgga   4020
aaatgcatga aaacatactg caacaattta ttttaatgtt cattaagtgc taaggttttt   4080
aggattcttg aaatcctcaa attgatatgt tagcgacaca tatttgacta taatggtctt   4140
ctgttatttc attcatttat gtaacaaaaa caataacaca aaaatgtaca taacttttca   4200
tttactcgag acctattagt taaaaaaatg tggaggaatg agccttttct ttactacgtc   4260
gaaatataaa atttctgaga cataaatcaa ttataaatat acagtatatg cctgattaa    4320 aaaaagaaa aaaactttc aactgatttt gtaatgcaga aaatcatgct tagcacaacc     4380
agagcattcg ccaacatata catttgatgt ggacatcatc ctaataacct catataaaag   4440
gttttttttg accaaaatgt gtacaatatg aggttttgtt gcagattcag ggaaaagatc   4500
actttgtttg tcattgccta ctatcaaaac aaacatttga ggacagataa gttcgagact   4560
gcaaagaccc tgaaaaggtc tccatgacct ggatgtcaca aaagcctttc attcattcca   4620
acgcaacgac ctgatctggc atttcacgca aggacagaa tagtccacat gaattacata    4680
aaattgactt aacaaaacac accctgaagc gtttgtgatt gggagctact tggtttgaga   4740
ggtggagttt gaagagcatc aaaggtaaag acacataaat agagcaggag agggaaattt   4800
acacttaggg acccatcggg tcagacagct gtgggacc                          4838
```

<210> SEQ ID NO 3
<211> LENGTH: 761
<212> TYPE: DNA
<213> ORGANISM: Oryzias melastigma

<400> SEQUENCE: 3

```
tttaggattc ttgaaatcct caaattgata tgttagcgac acatatttga ctataatggt    60
cttctgttat ttcattcatt tatgtaacaa aaacaataac acaaaaatgt acataacttt   120
tcatttactc gagacctatt agttaaaaaa atgtggagga atgagccttt tctttactac   180
gtcgaaatat aaaatttctg agacataaat caattataaa tatacagtat atggcctgat   240
taaaaaaaag aaaaaaactt tcaactgat tttgtaatgc agaaaatcat gcttagcaca    300
accagagcat tcgccaacat atacatttga tgtggacatc atcctaataa cctcatataa   360
aaggtttttt ttgaccaaaa tgtgtacaat atgaggtttt gttgcagatt cagggaaaag   420
atcactttgt ttgtcattgc ctactatcaa aacaaacatt tgaggacaga taagttcgag   480
actgcaaaga ccctgaaaag gtctccatga cctggatgtc acaaaagcct tcattcatt   540 ccaacgcaac gacctgatct ggcatttcac gcaaggaca gaatagtcca catgaattac    600
ataaaattga cttaacaaaa cacaccctga agcgtttgtg attgggagct acttggtttg   660
agaggtggag tttgaagagc atcaaaggta aagcacata aatagagcag gagagggaaa    720
tttacactta gggacccatc gggtcagaca gctgtgggac c                      761
```

<210> SEQ ID NO 4
<211> LENGTH: 361
<212> TYPE: DNA
<213> ORGANISM: Oryzias melastigma

<400> SEQUENCE: 4

| | | | | | | |
|---|---|---|---|---|---|---|
| gttgcagatt | cagggaaaag | atcactttgt | ttgtcattgc | ctactatcaa | aacaaacatt | 60 |
| tgaggacaga | taagttcgag | actgcaaaga | ccctgaaaag | gtctccatga | cctggatgtc | 120 |
| acaaaagcct | ttcattcatt | ccaacgcaac | gacctgatct | ggcatttcac | gcaaaggaca | 180 |
| gaatagtcca | catgaattac | ataaaattga | cttaacaaaa | cacaccctga | agcgtttgtg | 240 |
| attgggagct | acttggtttg | agaggtggag | tttgaagagc | atcaaaggta | aagacacata | 300 |
| aatagagcag | gagagggaaa | tttacactta | gggacccatc | gggtcagaca | gctgtgggac | 360 |
| c | | | | | | 361 |

<210> SEQ ID NO 5
<211> LENGTH: 831
<212> TYPE: DNA
<213> ORGANISM: Oryzias melastigma

<400> SEQUENCE: 5

| | | | | | | |
|---|---|---|---|---|---|---|
| ctgtgaaccg | acagaagctc | cagagttcgg | aaaaaataac | ataacattat | gaaaatctgt | 60 |
| ttcatcatgg | ttcagaatta | aatgcataaa | gtgaaaaatc | tgttgcaggt | gtttggaatg | 120 |
| tattgcaaaa | acaaaacaag | ttgatacata | aaggtagcaa | catttcttca | catttcatgt | 180 |
| aaaaaaaaaa | aaaaagtttc | ttcacatcag | tatagcaggt | gtgtagatac | agttgacaaa | 240 |
| atacaacact | tccaccttaa | tattctatat | ggatcaaatg | tgactgtttt | cagtgaaacg | 300 |
| tcacgacaat | aaagtcacat | aatacatttc | acttttacac | aaattttac | tgtctgtttc | 360 |
| tgttcttaaa | catacaagca | ctgaaaacag | agatgaatcc | agtataacca | aacaactcaa | 420 |
| acgacaataa | aaaaaacaaa | aaaattgttt | tattatttta | aaatgtttaa | aaaaagttca | 480 |
| atttttaaat | caaagtaggt | caaccatttt | taatactgga | tcaacaaaca | aaaacaatta | 540 |
| acaaaaaaaa | tcagagttaa | tggaaggtaa | acacacacat | ccgtgaagac | aaaaacacaa | 600 |
| gattattatt | taaaaactga | actagacagc | ttacttctca | gaaatctgcg | actgtaagga | 660 |
| aaactgtttt | ccttgttgct | ttcaatttgt | aaaattgaaa | gatgtcaata | aataatttac | 720 |
| cctcttgcat | tttgaaaaca | attgtacttt | cttggaagaa | tatttggcat | aaatgcatgt | 780 |
| ttacatgtgg | atgtcgggtt | tttaagcacc | tgctatggtg | agcttgggcc | a | 831 |

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6

| | | |
|---|---|---|
| gtaatacgac | tcactatagg gc | 22 |

<210> SEQ ID NO 7
<211> LENGTH: 19
<212> TYPE: DNA
<213> ORGANISM: Artificial
<220> FEATURE:
<223> OTHER INFORMATION: Primer

```
<400> SEQUENCE: 7
actatagggc acgcgtggt                                              19

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
aacgtgttga gggtcctgcg gcttc                                       25

<210> SEQ ID NO 9
<211> LENGTH: 28
<212> TYPE: DNA
<213> ORGANISM: Artificial
<220> FEATURE:
<223> OTHER INFORMATION: Primer

<400> SEQUENCE: 9
ctgtggatag tatggagggt atggaacc                                    28

<210> SEQ ID NO 10
<211> LENGTH: 35
<212> TYPE: DNA
<213> ORGANISM: Artificial
<220> FEATURE:
<223> OTHER INFORMATION: Primer

<400> SEQUENCE: 10
gtgtaatgga tgtggacttt ttctataaga caacc                            35

<210> SEQ ID NO 11
<211> LENGTH: 26
<212> TYPE: DNA
<213> ORGANISM: Artificial
<220> FEATURE:
<223> OTHER INFORMATION: Primer

<400> SEQUENCE: 11
cccaaaatgc atgtgcagct gatggc                                      26

<210> SEQ ID NO 12
<211> LENGTH: 25
<212> TYPE: DNA
<213> ORGANISM: Artificial
<220> FEATURE:
<223> OTHER INFORMATION: Primer

<400> SEQUENCE: 12
gaaaatctgt ttcatcatgg ttcag                                       25

<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
ttcacaactg gtaccctgtc ctgg                                        24

<210> SEQ ID NO 14
<211> LENGTH: 58
```

```
<212> TYPE: DNA
<213> ORGANISM: Artificial
<220> FEATURE:
<223> OTHER INFORMATION: Primer

<400> SEQUENCE: 14
tgcatggcat gcttaattaa ctgcagcccg gggtcgactc gtacctccaa aacccaac        58

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
ctccagtgcc ttgccatggt                                                  20

<210> SEQ ID NO 16
<211> LENGTH: 31
<212> TYPE: DNA
<213> ORGANISM: Artificial
<220> FEATURE:
<223> OTHER INFORMATION: Primer

<400> SEQUENCE: 16
tcgactgcag tgctctcact ctatggggtt c                                     31

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
ctccagtgcc ttgccatggt                                                  20

<210> SEQ ID NO 18
<211> LENGTH: 30
<212> TYPE: DNA
<213> ORGANISM: Artificial
<220> FEATURE:
<223> OTHER INFORMATION: Primer

<400> SEQUENCE: 18
agctactagt ccatctacat ggccaagaag                                       30

<210> SEQ ID NO 19
<211> LENGTH: 25
<212> TYPE: DNA
<213> ORGANISM: Artificial
<220> FEATURE:
<223> OTHER INFORMATION: Primer

<400> SEQUENCE: 19
attttgccga tttcggccta ttggt                                            25

<210> SEQ ID NO 20
<211> LENGTH: 29
<212> TYPE: DNA
<213> ORGANISM: Artificial
<220> FEATURE:
<223> OTHER INFORMATION: Primer

<400> SEQUENCE: 20
```

```
tgcagcggcc gcctgtgaac cgacagaag                                    29
```

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21

```
cacggatgtg tgtgtttacc                                              20
```

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22

```
gaaaatctgt tcatcatgg ttcag                                         25
```

<210> SEQ ID NO 23
<211> LENGTH: 24
<212> TYPE: DNA
<213> ORGANISM: Artificial
<220> FEATURE:
<223> OTHER INFORMATION: Primer

<400> SEQUENCE: 23

```
ttcacaactg gtaccctgtc ctgg                                         24
```

<210> SEQ ID NO 24
<211> LENGTH: 29
<212> TYPE: DNA
<213> ORGANISM: Artificial
<220> FEATURE:
<223> OTHER INFORMATION: Primer

<400> SEQUENCE: 24

```
tgcagcggcc gcctgtgaac cgacagaag                                    29
```

<210> SEQ ID NO 25
<211> LENGTH: 24
<212> TYPE: DNA
<213> ORGANISM: Artificial
<220> FEATURE:
<223> OTHER INFORMATION: Primer

<400> SEQUENCE: 25

```
ttcacaactg gtaccctgtc ctgg                                         24
```

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26

```
tgctgcccga caaccactac c                                            21
```

<210> SEQ ID NO 27
<211> LENGTH: 23
<212> TYPE: DNA
<213> ORGANISM: Artificial

```
<220> FEATURE:
<223> OTHER INFORMATION: Primer

<400> SEQUENCE: 27
ttacttgtac agctcgtcca tgc                                              23
```

TRANSGENIC FISH AND USES THEREOF

CROSS REFERENCE TO RELATED APPLICATIONS

This application is a divisional of U.S. patent application Ser. No. 12/730,956, filed Mar. 24, 2010, the disclosure of which is hereby incorporated herein by reference in its entirety.

FIELD OF THE INVENTION

The present invention relates generally to transgenic fish and their use in, inter alia, detecting estrogenic and anti-estrogenic compounds, monitoring estrogen-like activity in the environment, and elucidating liver regeneration.

BACKGROUND OF THE INVENTION

Many chemical substances that have been regarded as safe are found to have the activity to disrupt the endocrine system and cause adverse effects in organisms. The wide presence of these kinds of chemicals in the environment has raised attention and concern worldwide. Because of the increasing reports of the estrogenic effects of these substances on male organisms, most of the research efforts have been directed to estrogen-like endocrine disruptors.

It is important to have a rapid, sensitive, economical, and quantifiable method to identify chemical substances that can mimic estrogen or interfere with the estrogen endocrine system, and that can assist in evaluating the biological effects of these chemical substances on organisms. Of the current available methods, in vitro cell line assays and in vivo transgenic fish assays have been investigated. Cell line assays can be rapid and sensitive, but they cannot provide information on toxicodynamic and toxicokinetic effects of test substances on organisms. Currently, transgenic fish assays can overcome some of the deficiencies of the cell line assays. However, current transgenic fish assays are limited in that they cannot be used to monitor endocrine disruptors in freshwater species, and they cannot be used in a marine environment.

SUMMARY OF THE INVENTION

One aspect of the present invention relates to an expression cassette that includes: (i) a reporter nucleotide sequence encoding a reporter protein; (ii) an estrogen-responsive 5'-regulatory nucleotide sequence isolated from a medaka fish, where the regulatory nucleotide sequence is operably linked 5' to the reporter nucleotide sequence to induce expression of the reporter protein in the presence of estrogen or an estrogen-like compound; and (iii) a 3'-regulatory region operably linked 3' to the reporter nucleotide sequence.

Another aspect of the present invention relates to a transformation vector that includes an expression cassette of the present invention.

Another aspect of the present invention relates to a host cell transduced with an expression cassette of the present invention.

Another aspect of the present invention relates to a transgenic cell of an aquatic animal, where the transgenic cell includes at least one expression cassette of the present invention.

Another aspect of the present invention relates to a transgenic fish that includes at least one expression cassette of the present invention. The transgenic fish exhibits an observable mark when exposed to a liquid medium containing an estrogen or an estrogen-like compound. The observable mark includes a reporter protein expressed by the at least one expression cassette.

Another aspect of the present invention relates to a method of preparing a transgenic fish for use in detecting the presence of an estrogen or estrogen-like compound in a liquid medium. This method involves transforming a non-transgenic fish with the expression cassette of the present invention, thereby yielding a transgenic fish that includes at least one of the expression cassettes.

Another aspect of the present invention relates to a method of screening a liquid medium for an estrogenic substance.

Another aspect of the present invention relates to a method of screening a liquid medium for an estrogenic substance. This method involves exposing a transgenic fish of the present invention to a liquid medium to be tested (i.e., to be tested for the presence of an estrogenic substance). After this exposing step, the method then involves determining whether or not the transgenic fish exhibits an observable mark produced by the induced expression of the reporter gene (contained in the transgenic fish). The presence of the observable mark indicates that the liquid medium contains an estrogenic substance.

Another aspect of the present invention relates to a method of screening for a compound having anti-estrogenic activity. This method involves the following steps: (a) providing a first transgenic fish and a second transgenic fish of the present invention, where the first and second transgenic fish are of the same species and at substantially the same developmental stage; (b) exposing the first transgenic fish to a first liquid medium, where the first liquid medium includes an estrogen or estrogen-like compound; (c) exposing the second transgenic fish to a second liquid medium, where the second liquid medium includes the first liquid medium and a test compound; and (d) comparing the quantified intensity of any observable mark exhibited by the first transgenic fish with the quantified intensity of any observable mark exhibited by the second transgenic fish, where a decrease in the quantified intensity of the observable mark in the second transgenic fish compared to that of the first transgenic fish indicates that the test compound has anti-estrogenic activity.

Another aspect of the present invention relates to a method for investigating the effect of an estrogenic compound on liver regeneration. Generally, this method involves performing a partial hepatectomy on an adult transgenic fish of the present invention, where the partial hepatectomy is effective to remove a portion of the liver of the transgenic fish; exposing the transgenic fish to a test liquid medium containing a test estrogenic compound; and analyzing the liver of the transgenic fish to detect any regeneration of liver tissue.

Another aspect of the present invention relates to a method for investigating the effect of different estrogenic compounds on liver regeneration, as opposed to investigating a single estrogenic compound. Generally, this method involves the following steps: (a) providing a first transgenic fish and a second transgenic fish of the present invention, where the first and second transgenic fish are adults of the same species; (b) exposing the first transgenic fish to a first liquid medium that includes a first test estrogenic compound solution; (c) exposing the second transgenic fish to a second liquid medium comprising a second test estrogenic compound solution; (d) quantifying the intensity of any observable mark exhibited by the first transgenic fish and the second transgenic fish; (e) performing a partial hepatectomy on the first and second transgenic fish, where the partial hepatectomy is effective to remove a portion of the liver of the first and second transgenic fish; (f) repeating steps (b) through (d) of this method; and (g)

analyzing the liver of the first and second transgenic fish to compare the effects of the estrogenic compounds contained in the first liquid medium and the second liquid medium on any regeneration of liver tissue.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

FIGS. 3E-3G show that the expression of transgene GFP can also be induced in the liver of embryo, larva and male fish by 17β-estradiol.

DETAILED DESCRIPTION OF THE INVENTION

Figure 1:
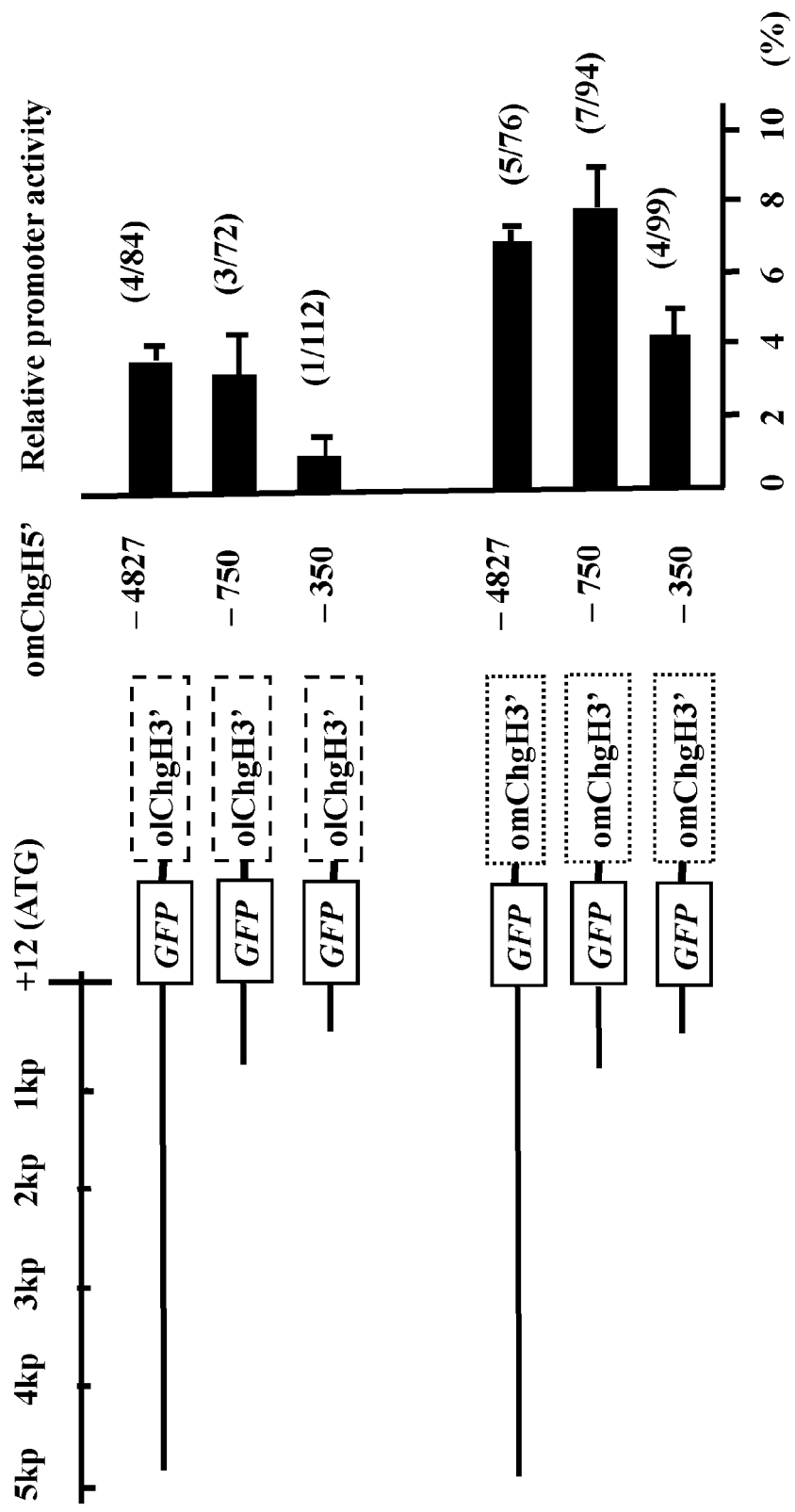
FIG. 1 depicts the relative promoter activity of different lengths of omChgH5'-upstream region represented by the frequency of GFP positive larva derived from embryos injected with nucleic acid sequences including the omChgH promoter-EGFP (enhanced green fluorescence protein) in response to 17β-estradiol.

In one aspect, the present invention relates to a transgenic fish that contains an expression cassette that includes an estrogen-responsive 5'-regulatory nucleotide sequence isolated from a medaka fish, where the estrogen-responsive 5'-regulatory nucleotide sequence is operably linked 5' to a reporter nucleotide sequence. When the transgenic fish is exposed to a liquid medium containing estrogen or an estrogen-like compound, the reporter nucleotide sequence expresses a corresponding reporter protein that can be detected in vivo or in vitro. The transgenic fish of the present invention is useful for a variety of applications, including, without limitation, for use in detecting estrogenic compounds and anti-estrogenic compounds, monitoring estrogen-like activity in the environment, and elucidating liver regeneration.

The transgenic fish of the present invention can be of various freshwater, brackish water, or saltwater (marine water) species of fish, including, without limitation, fish of the *Oryzias* species and the *Danio* species. Fish in the *Oryzias* genus belong to the Adrianichthyidae family and include, for example, *Oryzias melastigma* (alternative name *Oryzias dancena*) (Marine or brackish medaka), *Oryzias latipes* (Japanese medaka), *Oryzias celebensis, Oryzias marmoratus, Oryzias matanensis, Oryzias nigrimas* (black buntingi), *Oryzias orthognathus* (buntingi), and *Oryzias profundicola*. Fish in the *Danio* genus belong to the Cyprinidae family and include, for example, *Danio rerio* (zebra fish), *Danio albolineatus, Danio abolineatus, Danio choprae, Danio dangila, Danio erythromicron, Danio feegradei, Danio kerri, Danio kyathit, Danio margaritatus, Danio meghalayensis, Danio nigrofasciatus*, and *Danio roseus*.

With regard to the brackish medaka fish (*Oryzias melastigma*), this species is one of many medaka species identified as belonging to the *Oryzias* genus (some species being set forth herein above). The brackish medaka fish is native to coastal waters and fresh waters in Pakistan, India, Burma and Thailand (K. Naruse, *Fish Biol. L. Medaka* 8:1-9 (1996)), and thrives in waters of varying salinity ranging from 0 parts per thousand (ppt) to as high as 35 ppt. Additionally, this brackish medaka fish has a number advantages for transgenic development, including: (1) small size (2-3 cm for adult fish); (2) relatively short generation time (2-3 months); (3) dimorphic sex (e.g., females have a flat distal surface of the anal fin, while that of males is convex due to separated longer fin rays); (4) high prolific capacity to reproduce; (5) translucent eggs and larvae (up to 15 days post fertilization), which facilitates the positioning of DNA microinjection needles and observation of internal organs; and (6) adaptable to various transgenic techniques used to produce transgenic fish of other *Oryzias* species (e.g., *Oryzias latipes*).

Regarding the highly prolific capacity of the brackish medaka fish to reproduce, spawning of this fish can be induced all year round, and each pair of female and male fish can produce 20-30 eggs daily for up to several months under indoor maintained conditions (e.g., 28±1° C. with a constant light cycle of 14 h-light/8 h-dark and fed with commercial hormone-free flake food and brine shrimp (*Artemia salina*)). Eggs usually hatch in 11 to 15 days at 28±1° C.

*Oryzias latipes* has been used to produced transgenic fish carrying a variety of transgenes (e.g., K. Ozato et al., *Cell Differ.* 19:237-244 (1986); K. Inoue et al., *Cell Difer. Dev.* 27(1):57-68 (1989); E. Tamiya et al., *Nucleic Acids Res.* 18:1072 (1990); K. Inoue et al., *Cell Differ. Dev.* 29(2):123-

128 (1990); J. Lu et al., *Mol. Marine. Biol. and Biotechnol.* 1(4/5):366-375 (1992); H. J. Tsai et al., *Mol. Mar. Biol. Biotechnol.* 4(1):1-9 (1995); R. N. Winn et al., *Marine Env. Res.* 40(3):247-265 (1995)). Studies have shown that the two medaka species of *Oryzias melastigma* and *Oryzias latipes* share high morphological, physiology, and genomic similarity, and that it is easy to adapt the transgenic technique from *Oryzias latipes* to the brackish medaka *Oryzias melastigma* (X. Chen et al., *Ectoxicol. Environ. Saf* 71:200-208 (2008); X. Chen et al., *Comp. Biochem. Physiol. C. Toxicol. Pharmacol.* 149:647-655 (2009)).

In one embodiment, the transgenic fish of the present invention is engineered to contain one or more copy of a linearized nucleic acid sequence containing the promoter region of an estrogen target gene, which is operably ligated to the coding region of a reporter gene (e.g., a fluorescence protein gene), and then flanked by a termination sequence (e.g., an mRNA polyadenylation signal sequence). The promoter region sequence and the termination sequence can originate from the same estrogen target gene, although the present invention does not require that they have the same origin.

A suitable promoter region can be one that is derived from an estrogen-dependent gene. In one embodiment, a particular estrogen-dependent gene contemplated by the present invention can include, without limitation, the choriogenin H genes from *Oryzias melastigma* (the gene being abbreviated as "omChgH") and *Oryzias latipes* (the gene being abbreviated as "olChgH").

The omChgH gene of *Oryzias melastigma* has been characterized as being highly sensitive to estrogen and estrogen-like substances. The complete coding sequence of the omChgH gene of *Oryzias melastigma* has been determined and deposited as GenBank Accession No. EF392365. As used herein, the omChgH gene coding sequence corresponds to SEQ ID NO:1, as follows:

```
   1    gaattcacta gtgattacta tagggcacgc gtggtcgacg gcccgggctg gtatcgtgag
  61    ccatgtatcg cgtatcgtat cgtatcgtga ggtacccagt gattcccagc cctaataatt
 121    atggctaaat actatatatg tagaaatcta actgttgtta aaaaagccag agttttttta
 181    atcttcacaa agaaattgtt ttgcaaatta atgaaaatcc aatgcaaaag ctgttaggac
 241    agtcgaagcc tggacttgtt tggcatcata ttttattatt attattatga ttcctttctt
 301    ttgttacccc ctggcaagtt catatcaatt attctgtaat tctcggtatt ggatcattta
 361    ttctttatat gtgctacatt ttgacaaaaa aaaatcgata ttatgaacat tataccttta
 421    caaatctgtt ttacacatct cctgatttta caaagaaaat attatactaa ttaaactaaa
 481    tgtagtgata aagctccaaa tttatttggt ttattttccc aaatccatca ttatttacaa
 541    tatttcattt tgtccaaaca caaaaataaa gtttcacaac tagatagatt atcatgattt
 601    tacctctgtt ttttttttt caatttttt cctataataa ctacccaggc gtttatcttg
 661    aaaaattagt tattgttctg tgttctgttc tacataagag gattaaggcc atggaggaat
 721    taaacgggta tggataattc taagtttaaa gtcagaattc tgactttttt ttcctcggaa
 781    ttctgacttt tttcccagaa ttctggcctt ttatatattt tttagaaaga tttagaaaca
 841    tattaaattt cttactgcta catttcatct cgtacctcca aaacccaaca tattttgtct
 901    ataaggttg agcttaaaaa tatatatttt ttcaattaaa agaaaataac tgaaaaactg
 961    gaatttaatc ttaaaactac caagaagtta tctatttaat cattatgttt acattcaagt
1021    cgtcttaggg ccacaaggta cttagccttt gctgttattt acaaagacga caatttaagt
1081    gtatgaagtg atctttataa atcagtcaaa tatattttt taaatgcact cattcccctt
1141    tggcagcaag ttgtggcgaa aatcctttat aatcttcaaa ttacaagtat gaacaatatt
1201    gtttccttta aaacaattag cagtctaatc attttctata atatgaaagt tcatatctta
1261    tgtagttgaa aagtgtgcta ttttttgtaat tgtatttctt tttatatatt ttgcatttag
1321    tgaactactg cattaactag cttgcaatac ttttcgcatt gtgtctctca taaaaaatat
1381    agatatggtt atttaaaaaa atgcgtttac tcttaattgt tgccttttgg agtaaaattt
1441    tatgcttttg tctgtattgc cttttttgaca ttcagaagag gatgcttctg tatgacggcg
1501    tattaaggcc ttgagggtat catgtctgtg gtgtgactga atgattacat tgatgctgtt
1561    ttacactttg aaaatcacca tttgaaacca agttttgtct cacaattgca tcaaacagaa
1621    aaaaaccat caaagcaagc taattgaatg ttgattggtt taatccaagt cattacagtt
1681    tattccacct gagtctagat gattctaaca gattgtttga ctgttgtcaa aatgatccta
```

-continued

```
1741  catgaatgca agtccaaagc aagataaatg ctctttctct tcaaatgatt tgacattaat
1801  cttccccta aatttattat tggtcataat attgataaat ctttgtttcg tgatgcatga
1861  gaccttatca cctaattttg cagtaaagag agtcaactaa aaaattttct gacactcttt
1921  tgttacttat tatctcatga aatcctttgt actgttttgc cttggggttt ttattgacta
1981  acatctcttt aatcacacat aattcaactg ttcataattc caaatatgtt ttagcttttg
2041  ttataacgat ttaagttaca gcaatgtgtt ttattttttt ctgtatttaa ctgaactatg
2101  ttgcccttat aaacagttac atgtatgtaa taggagtggc ctgatattgc cacacacccc
2161  tcatcggatg ctatgtcatg gacaaatagc tccactatat ggtcaaacat aagtataact
2221  taagaaagta acagaaaaat ttaatttaaa aaagttttt ttttttttt gtcttttcca
2281  tttcttatt ttatttattt aaatccaaaa aaagtcaaat cctttacttc tcggcacata
2341  attttcaaa caatctttt aaataaaatt attaattaaa gcaaatattc attcacaaaa
2401  aaaaacttt agagtttgaa aaatgcgaat ttaaagttgt attattataa tcaatattga
2461  tttaagttta caaatagatt taaaaaaaaa atggaaatct gctatgtttc cttgacagcc
2521  ttcaaaagtt tccttctgga aaagttaaac tgttgttttg tgacggtgtt tttttttaaa
2581  cgctttgtct ggatcaatta aagcatagtt ttttcacatt tgcggttttt cacggagaga
2641  ggaagtttcc tttattgtgt atcctgccct gagtaccagt gacattagag cctgtaacgt
2701  gtcaaataaa gtgacacagt tggccagatc taaagtctcg gatgttgtgt tctggtcaaa
2761  taaacatatg acaatgaata aaagttgagg tcacatggac attttgaaaa gggcttttat
2821  gacctagagt ttgatttgta gataaacccc tttatgtcaa actgtcatca aacacaaccc
2881  tgatccaaca gcgttacccc ttagctatca cagttcactt tgtaaatttg tcacaaaaaa
2941  tgggtcataa tcatcaaaat gaattataat ttctaagaaa ttatagcatt tagatattgc
3001  acctttttaa acacctcaaa attactggtt tctttctt ttattatttc tttagtttta
3061  agtttgtttt gaaaatgatc ttaatattgc agcggagtag cacgtatta actaaaatta
3121  aaactactaa ccatgaacat ttttcagcat ttgtgtggtt tagttttgt gacatgtttg
3181  catgtagtca tattttgagt ttttgaggtg cttttaaca gctttcagaa gcagtttaac
3241  catttaaaat taagaaaatt caagctcaga ttacacttt catattatct tagtttgtga
3301  aaaaatagta ttataatata ttagaagact ttcttctaca caggactacc tgaggtttaa
3361  acaacacttt atcaactgag aggtagcact gaaatatgtg cgctgcaagt tatttaattg
3421  ttttttttt tttatttt agctcttgct acctagaaac attgtaaaaa aaattactga
3481  aactttacac attaattttc tgaagacctc atcataatcc atgatgttta acgggtttga
3541  attgcactta ttttactgc atcataatta ccacatccac tctattaaat tctattccaa
3601  taccagagtt aaggctagag tttggtacac tacgaccgat ccacagttat gcaacgtaat
3661  tctgagaaac tatgagtctc ctttattatt cctctatcaa accagtggtg aaggaagtat
3721  tttaattttt acttaaataa aacttttcaa cattaaacaa ttcaaatgtg tgtgcgtctg
3781  tctgaattca tttaattatt cgttaattga ttttctacac aattaatact tgcatatgtt
3841  ttgctttttt taaatgctaa cttattaca ttttctgatt ggggctaaaa atcaactgga
3901  aagaaaatgg tttttttac acttcattat gtcctgtttg gggttgctgg agcctgtccg
3961  agttacctca ggggaaaagc cagagtgcac cctgaacatt gagaggtcac acacagacac
4021  atccatccat gttcttaacc tgctaaatcc cttattaagc atgattttgg actgtctgaa
4081  gaaaagccaa gcaagaacat gccaagtcca cgcaaagggt cccaaccat gctttcaacc
4141  aggaccagct tactgtgagg tgagaccgct aactactgca ccacagtgca gcccatattt
```

```
4201  agacttaatg caatatattg tgttttgggg aagaagctgg agagcctgga gggaaccagt
4261  gcatggggaa aacatacaaa cctcacacag caaggatcac atctgcctca gtatgtattt
4321  ttacagctta ctgtaattaa aaacagtaaa aaaaaaaaaa ctaaaaaaaa aaacatcaaa
4381  ttgccacaaa aagtacatga tttaaaaaaa ggtttctgtc tacatgttta catcttaatt
4441  tgatttaaaa cactaaaaaa tacataagat tgcccccaaa aaatgcaatt ataaaaagca
4501  catgatttaa aaaaaaaaag gtatccgtac gtattttttag atcttaattt ggcttaaaca
4561  ctaaaaaata cattagattg ccaaaaaatg caattataaa tatacatgtt ttttaataaa
4621  agccatcagc tgcacatgca tttttgggaaa aaaaggttgt cttatagaaa aagtccacat
4681  ccattacaca atttaactgt ttactttgaa taaaaacaca ttactgtgct gctttattat
4741  tgctctcact ctatggggtt caaactaatg tgtatttgtc attttttgtgc tttgtttagt
4801  ggatatctaa cagtatgtca acagactgaa agggcaaaag aggtaattac ttcctaaaca
4861  gctaacatta gattgtttct gtcatggaaa atgcatgaaa acatactgca acaatttatt
4921  ttaatgttca ttaagtgcta aggtttttag gattcttgaa atcctcaaat tgatatgtta
4981  gcgacacata tttgactata atggtcttct gttatttcat tcatttatgt aacaaaaaca
5041  ataacacaaa aatgtacata acttttcatt tactcgagac ctattagtta aaaaaatgtg
5101  gaggaatgag cctttttcttt actacgtcga aatataaaat ttctgagaca taaatcaatt
5161  ataaatatac agtatatggc ctgattaaaa aaaagaaaaa aacttttcaa ctgattttgt
5221  aatgcagaaa atcatgctta gcacaaccag agcattcgcc aacatataca tttgatgtgg
5281  acatcatcct aataacctca tataaaaggt ttttttttgac caaaatgtgt acaatatgag
5341  gttttgttgc agattcaggg aaaagatcac tttgtttgtc attgcctact atcaaaacaa
5401  acatttgagg acagataagt tcgagactgc aaagaccctg aaaaggtctc catgacctgg
5461  atgtcacaaa agcctttcat tcattccaac gcaacgacct gatctggcat ttcacgcaaa
5521  ggacagaata gtccacatga attacataaa attgacttaa caaaacacac cctgaagcgt
5581  ttgtgattgg gagctacttg gtttgagagg tggagtttga agagcatcaa aggtaaagac
5641  acataaatag agcaggagag ggaaatttac acttagggac ccatcgggtc agacagctgt
5701  gggaccatgg caaggcactg gagtattacg gttttttccg cactagctct gatatgttct
5761  ttcctggcga cccaagtgga tgctcagaaa ggcccccctc aagaccctaa ggttccatac
5821  cctccatact atccacagcc gaagccgcag gaccctcaac acgtttcacc gccttacaac
5881  ccagggaagc cgcagtatcc agggaagcca cagtatccag ggaagccgca gagtccacag
5941  tatcctcaga cccctcagta tcctcagacc cctcagcagc cgcagagtcc acagtatcct
6001  cagacccctc agtatcctca gaccccctcag cagccgcaga gtcctcagta tcctcagtcc
6061  cctcagtatc ctcagactcc tcagtcccct cagtatcctc agtcccctca gtatcctcag
6121  actcctcagt atcctcagaa tcctaaggtg tatggtgatg acagttctaa gccttcaact
6181  ccgtcaaagc ctagctatcc tcagcctcag gccccccagt acccatctaa gcctcaagct
6241  ccccagctgc ctcaggcccc ccagtaccca actaagcctc aagctcccca gctgcctcaa
6301  gctccccagc tgcctcaggc ccccagtac ccaactaagc ctcaagctcc tcagtatcct
6361  caagctcctc agcagcctca ggcccccag tacccaacta gcctcaagc tcctcagcag
6421  ccccaggctc cccagtaccc aactaagcct caagctcctc agtaccctca agctcctcag
6481  cagccccagg ctccccagta cccaacaaaa cctcagcagc cccagtaccc aacaaagcct
6541  cagtctcctc agtaccctca agatcctaaa aatccaaatc ctcagaatcc tcctcttcat
```

```
6601  cctcccctg ttaagagctg tgaggtgccc cgcgatgtga gagtcccatg tggagttcca
6661  gacatctctc cttctgcatg cgatgccatt gactgctgtc atgatggcca agcctgctac
6721  tttggaacag gaggtaagtg gtttctccag ctgctatgat cagaggcttt ttgtaaggtg
6781  acggctgatc gtgcaatcgt cgatcccatc tatttcttct agcaaccgtt cagtgcacca
6841  aggacggaca cttcatcgtt gtggtggcca aggatgtcac cttaccccat ctcgatcttg
6901  aaactatttc acttttggga ccgggtcaag aatgtggagc tgttgactct aattcagctt
6961  tcgccatcta ctactttccc gtcactcagt gcggcactca tgtcacggta acactcagtc
7021  ttgtttatat cttatagtca taaggtcaat cttgagatt ctatccttct tattgttaaa
7081  ttttgaacca ttaaaaggaa gagcccgggg ttatagtcta tgaaaaccgg atgacatcct
7141  catatgaagt tggagttgga ccgcttggag ctattaccag agacagctct tttgagtagg
7201  tcatcatttg tgtttagtat caaacagatt tactaatgtc taactaatat ctatcagggg
7261  taaacagaat catgcacagt gtattaacac agttcttttt ctcaggctcc tcttccagtg
7321  cagataccat gcaacatctg ttgaaactct ggtcgtggaa gtgctgccag tggatagtcc
7381  tctttccatt gctgagcttg gaccctcaa tgtgtacttg caaattgcca atggagtatg
7441  tcagacaaag ggctgcgacg aaggtcagtg cacggcagtc tggcacagcc agtgtgtttg
7501  tcaaacattt gaaaagctg cctgtcgtaa cgtttgtttg ctcccacagt ggcggcagcc
7561  tacacctctt tctacacgga tgccgactat cctgtgacca aagtactgag agaaccagtc
7621  tatgtggacg ttcaaatcct tggcagaaca gatccaaatc tggttctgac tcttggacgc
7681  tgttgggcaa ccacaagccc caatgctttc agtctgcccc agtgggacat tttgattgac
7741  gggtaaaaaa aaaaaatct accaattcat tccataaaga ccatttttgt tcaaactaag
7801  ctccaaatct cacactttt agccgaatta ctaaatatct aaccaaccat tacttcttct
7861  ttaccttttt tccatccaga tgtccatatg aagatgatcg ctacctgtct gcgttggttc
7921  caatcgattc ctcctctggt ttgccattcc caactcatca cagacgcttc ttattcaaga
7981  tgtttacctt tgttgatcct cattcaatgg aaccactaag ggaaaaggtg ggtactgaat
8041  tactcaagta gaggtttaac ttggcttcta acctgtactt ttctttcagg tgtacattca
8101  ctgcagcaca gctgcatgcg ttccaggaca gggtaccagt tgtgaaccct catgcagcag
8161  aagaagtagg gggctcattt ataaccgttc acatgttttt tttgttgttg taatgaccat
8221  gtccactcat cattggccat gttttgtgtc tttttgtaga aggaagagat actgacgctg
8281  tatccattag aacggatgaa agaaaggttg tggtatcgtc tggagaagtg ctcatggtgg
8341  ccgaagctgc tggacagtct taactgtgaa ccgacagaag ctccagagtt cggaaaaat
8401  aacataacat tatgaaaatc tgtttcatca tggttcagaa ttaaatgcat aaagt
```

The estrogen-responsive 5'-regulatory nucleotide sequence of the present invention can include, without limitation, any sequence of the promoter region of the omChgH gene of SEQ ID NO:1.

In one embodiment, a suitable estrogen-responsive 5'-regulatory nucleotide sequence of the present invention comprises a nucleotide sequence corresponding to SEQ ID NO:2, as follows:

```
ctcgtacctc caaaacccaa catattttgt ctataaaggt tgagcttaaa aatatatatt    60
ttttcaatta aaagaaaata actgaaaaac tggaatttaa tcttaaaact accaagaagt   120
tatctattta atcattatgt ttacattcaa gtcgtcttag ggccacaagg tacttagcct   180
ttgctgttat ttacaaagac gacaattaa gtgtatgaag tgatctttat aaatcagtca    240
aatatatttt tttaaatgca ctcattcccc tttggcagca agttgtgcg aaaatccttt    300
ataatcttca aattacaagt atgaacaata ttgtttcctt taaaacaatt agcagtctaa   360
```

-continued

```
tcattttcta taatatgaaa gttcatatct tatgtagttg aaaagtgtgc tatttttgta      420
attgtatttc ttttatata ttttgcattt agtgaactac tgcattaact agcttgcaat      480
acttttcgca ttgtgtctct cataaaaaat atagatatgg ttatttaaaa aaatgcgttt      540
actcttaatt gttgcctttt ggagtaaaat tttatgcttt tgtctgtatt gccttttga      600 cattcagaag aggatgcttc tgtatgacgg cgtattaagg ccttgagggt atcatgtctg      660
tggtgtgact gaatgattac attgatgctg ttttacactt tgaaaatcac catttgaaac      720
caagttttgt ctcacaattg catcaaacag aaaaaaaacc atcaaagcaa gctaattgaa      780
tgttgattgg tttaatccaa gtcattacag tttattccac ctgagtctag atgattctaa      840
cagattgttt gactgttgtc aaaatgatcc tacatgaatg caagtccaaa gcaagataaa      900
tgctcttcct cttcaaatga tttgacatta atctttccct aaaatttatt attggtcata      960
atattgataa atctttgttt cgtgatgcat gagaccttat cacctaattt tgcagtaaag     1020
agagtcaact aaaaaatttt ctgacactct tttgttactt attatctcat gaaatccttt     1080
gtactgtttt gccttggggt ttttattgac taacatctct ttaatcacac ataattcaac     1140
tgttcataat tccaaatatg tttagcttt tgttataacg atttaagtta cagcaatgtg     1200
ttttattttt ttctgtattt aactgaacta tgttgccctt ataaacagtt acatgtatgt     1260
aataggagtg gcctgatatt gccacacacc cctcatcgga tgctatgtca tggacaaata     1320
gctccactat atggtcaaac ataagtataa cttaagaaag taacagaaaa atttaattta     1380 aaaaagttt ttttttttt ttgtcttttc catttctta ttttatttat ttaaatccaa     1440
aaaaagtcaa atcctttact tctcggcaca taattttca aacaatctttt ttaaataaaa     1500 ttattaatta aagcaaatat tcattcacaa aaaaaactt ttagagtttg aaaaatgcga     1560
atttaaagtt gtattattat aatcaatatt gatttaagtt tacaaataga tttaaaaaaa     1620
aaatggaaat ctgctatgtt tccttgacag ccttcaaaag tttccttctg gaaaagttaa     1680
actgttgttt tgtgacggtg ttttttttta aacgctttgt ctggatcaat taaagcatag     1740
ttttttcaca tttgcggttt ttcacggaga gaggaagttt cctttattgt gtatcctgcc     1800
ctgagtacca gtgacattag agcctgtaac gtgtcaaata aagtgacaca gttggccaga     1860
tctaaagtct cggatgttgt gttctggtca aataaacata tgacaatgaa taaaagttga     1920
ggtcacatgg acattttgaa aagggctttt atgacctaga gtttgatttg tagataaacc     1980
cctttatgtc aaactgtcat caaacacaac cctgatccaa cagcgttacc ccttagctat     2040
cacagttcac tttgtaaatt tgtcacaaaa aatgggtcat aatcatcaaa atgaattata     2100
atttctaaga aattatagca tttagatatt gcaccttttt aaacacctca aaattactgg     2160
tttcttttct ttttattatt tctttagttt taagtttgtt ttgaaaatga tcttaatatt     2220
gcagcggagt agcacgtatt taactaaaat taaaactact aaccatgaac attttcagc     2280 atttgtgtgg tttagttttt gtgacatgtt tgcatgtagt catatttga gtttttgagg     2340 tgcttttaa cagctttcag aagcagttta accatttaaa attaagaaaa ttcaagctca     2400
gattacactt ttcatattat cttagtttgt gaaaaatag tattataata tattagaaga     2460
ctttcttcta cacaggacta cctgaggttt aaacaacact ttatcaactg agaggtagca     2520
ctgaaatatg tgcgctgcaa gttatttaat tgtttttttt ttttatttt ttagctcttg     2580 ctacctagaa acattgtaaa aaaaattact gaaactttac acattaattt tctgaagacc     2640
```

-continued

```
tcatcataat ccatgatgtt taacgggttt gaattgcact tatttttact gcatcataat      2700
taccacatcc actctattaa attctattcc aataccagag ttaaggctag agtttggtac      2760
actacgaccg atccacagtt atgcaacgta attctgagaa actatgagtc tcctttatta      2820
ttcctctatc aaaccagtgg tgaaggaagt attttaattt ttacttaaat aaaacttttc      2880
aacattaaac aattcaaatg tgtgtgcgtc tgtctgaatt catttaatta ttcgttaatt      2940
gattttctac acaattaata cttgcatatg ttttgctttt tttaaatgct aacttttatta    3000 cattttctga ttggggctaa aaatcaactg gaaagaaaat ggttttttttt acacttcatt    3060 atgtcctgtt tggggttgct ggagcctgtc cgagttacct caggggaaaa gccagagtgc     3120
accctgaaca ttgagaggtc acacacagac acatccatcc atgttcttaa cctgctaaat     3180
cccttattaa gcatgatttt ggactgtctg aagaaaagcc aagcaagaac atgccaagtc     3240
cacgcaaaag ggtcccaacc atgctttcaa ccaggaccag cttactgtga ggtgagaccg     3300
ctaactactg caccacagtg cagcccatat ttagacttaa tgcaatatat tgtgttttgg    3360
ggaagaagct ggagagcctg gagggaacca gtgcatgggg aaaacataca aacctcacac    3420
agcaaggatc acatctgcct cagtatgtat ttttacagct tactgtaatt aaaaacagta    3480
aaaaaaaaaa aactaaaaaa aaaaacatca aattgccaca aaagtacat gatttaaaaa     3540 aaggtttctg tctacatgtt tacatcttaa tttgatttaa aacactaaaa aatacataag    3600
attgccccca aaaatgcaa ttataaaaag cacatgattt aaaaaaaaaa aggtatccgt     3660 acgtatttt agatcttaat ttggcttaaa cactaaaaaa tacattagat tgccaaaaaa     3720
tgcaattata aatatacatg ttttttaata aaagccatca gctgcacatg cattttggga    3780
aaaaaaggtt gtcttataga aaagtccac atccattaca caatttaact gtttactttg     3840
aataaaaaca cattactgtg ctgctttatt attgctctca ctctatgggg ttcaaactaa    3900
tgtgtatttg tcatttttgt gctttgttta gtggatatct aacagtatgt caacagactg    3960
aaagggcaaa agaggtaatt acttcctaaa cagctaacat tagattgttt ctgtcatgga   4020
aaatgcatga aaacatactg caacaattta ttttaatgtt cattaagtgc taaggttttt    4080
aggattcttg aaatcctcaa attgatatgt tagcgacaca tatttgacta taatggtctt   4140
ctgttatttc attcatttat gtaacaaaaa caataacaca aaaatgtaca taacttttca    4200
tttactcgag acctattagt taaaaaaatg tggaggaatg agccttttct ttactacgtc    4260
gaaatataaa atttctgaga cataaatcaa ttataaatat acagtatatg gcctgattaa    4320
aaaaaagaaa aaaactttc aactgatttt gtaatgcaga aaatcatgct tagcacaacc     4380
agagcattcg ccaacatata catttgatgt ggacatcatc ctaataacct catataaaag    4440
gttttttttg accaaaatgt gtacaatatg aggttttgtt gcagattcag ggaaaagatc    4500
actttgtttg tcattgccta ctatcaaaac aaacatttga ggacagataa gttcgagact    4560
gcaaagaccc tgaaaggtc tccatgacct ggatgtcaca aaagcctttc attcattcca     4620
acgcaacgac ctgatctggc atttcacgca aaggacagaa tagtccacat gaattacata    4680
aaattgactt aacaaaacac accctgaagc gtttgtgatt gggagctact tggtttgaga    4740
ggtggagttt gaagagcatc aaaggtaaag acacataaat agagcaggag agggaaattt    4800
acacttaggg acccatcggg tcagacagct gtgggacc                            4838
```

The estrogen-responsive 5'-regulatory nucleotide sequence of SEQ ID NO:2 corresponds to a 4827 base pair region 5' upstream of the omChgH gene of SEQ ID NO:1. Base pairs 4828-4838 of SEQ ID NO:2 correspond to a 5'-untranslated region of the omChgH gene of SEQ ID NO:1.

In one embodiment, a suitable estrogen-responsive 5'-regulatory nucleotide sequence of the present invention comprises a nucleotide sequence corresponding to SEQ ID NO:3, as follows:

```
tttaggattc ttgaaatcct caaattgata tgttagcgac acatatttga ctataatggt        60
cttctgttat ttcattcatt tatgtaacaa aaacaataac acaaaaatgt acataacttt       120
tcatttactc gagacctatt agttaaaaaa atgtggagga atgagccttt tctttactac       180
gtcgaaatat aaaatttctg agacataaat caattataaa tatacagtat atggcctgat       240
taaaaaaaag aaaaaaactt ttcaactgat tttgtaatgc agaaaatcat gcttagcaca       300
accagagcat tcgccaacat atacatttga tgtggacatc atcctaataa cctcatataa       360
aaggtttttt ttgaccaaaa tgtgtacaat atgaggtttt gttgcagatt cagggaaaag       420
atcactttgt ttgtcattgc ctactatcaa aacaaacatt tgaggacaga taagttcgag       480
actgcaaaga ccctgaaaag gtctccatga cctggatgtc acaaaagcct ttcattcatt       540
ccaacgcaac gacctgatct ggcatttcac gcaaaggaca gaatagtcca catgaattac       600
ataaaattga cttaacaaaa cacaccctga agcgtttgtg attgggagct acttggtttg       660
agaggtggag tttgaagagc atcaaaggta aagacacata aatagagcag gagagggaaa       720
tttacactta gggacccatc gggtcagaca gctgtgggac c                          761
```

The estrogen-responsive 5'-regulatory nucleotide sequence of SEQ ID NO:3 corresponds to a 750 base pair region 5' upstream of the omChgH gene of SEQ ID NO:1. Base pairs 751-761 of SEQ ID NO:3 correspond to a 5'-untranslated region of the omChgH gene of SEQ ID NO:1.

In one embodiment, a suitable estrogen-responsive 5'-regulatory nucleotide sequence of the present invention comprises a nucleotide sequence corresponding to SEQ ID NO:4, as follows:

```
gttgcagatt cagggaaaag atcactttgt ttgtcattgc ctactatcaa aacaaacatt        60
tgaggacaga taagttcgag actgcaaaga ccctgaaaag gtctccatga cctggatgtc       120
acaaaagcct ttcattcatt ccaacgcaac gacctgatct ggcatttcac gcaaaggaca       180
gaatagtcca catgaattac ataaaattga cttaacaaaa cacaccctga agcgtttgtg       240
attgggagct acttggtttg agaggtggag tttgaagagc atcaaaggta aagacacata       300
aatagagcag gagagggaaa tttacactta gggacccatc gggtcagaca gctgtgggac       360
c                                                                       361
```

The estrogen-responsive 5'-regulatory nucleotide sequence of SEQ ID NO:4 corresponds to a 350 base pair region 5' upstream of the omChgH gene of SEQ ID NO:1. Base pairs 351-361 of SEQ ID NO:4 correspond to a 5'-untranslated region of the omChgH gene of SEQ ID NO:1.

The 3'-regulatory region of the present invention can include, without limitation, a choriogenin H3'-flanking region that includes choriogenin H 3'-untranslated region (represented as UTR). In one embodiment, a suitable 3'-regulatory region can include the omChgH 3' UTR deposited as GenBank Accession No. DQ778335, which corresponds to the nucleotide sequence of SEQ ID NO:5, as follows:

```
ctgtgaaccg acagaagctc cagagttcgg aaaaaataac ataacattat gaaaatctgt        60
ttcatcatgg ttcagaatta aatgcataaa gtgaaaaatc tgttgcaggt gtttggaatg       120
tattgcaaaa acaaaacaag ttgatacata aaggtagcaa catttcttca catttcatgt       180
aaaaaaaaaa aaaaagtttc ttcacatcag tatagcaggt gtgtagatac agttgacaaa       240
atacaacact tccaccttaa tattctatat ggatcaaatg tgactgtttt cagtgaaacg       300
tcacgacaat aaagtcacat aatacatttc acttttacac aaatttttac tgtctgtttc       360
tgttcttaaa catacaagca ctgaaaacag agatgaatcc agtataacca aacaactcaa       420
acgacaataa aaaaaacaaa aaaattgttt tattatttta aatgtttaa aaaagttca        480 attttttaaat caaagtaggt caaccatttt taatactgga tcaacaaaca aaaacaatta       540
acaaaaaaaa tcagagttaa tggaaggtaa acacacacat ccgtgaagac aaaaacacaa       600
```

```
gattattatt taaaaactga actagacagc ttacttctca gaaatctgcg actgtaagga      660
aaactgtttt ccttgttgct ttcaatttgt aaaattgaaa gatgtcaata aataatttac      720
cctcttgcat tttgaaaaca attgtactttt cttggaagaa tatttggcat aaatgcatgt    780
ttacatgtgg atgtcgggtt tttaagcacc tgctatggtg agcttgggcc a              831
```

The practice of the present invention will employ, unless otherwise indicated, conventional techniques of chemistry, molecular biology, microbiology, recombinant DNA, and immunology, which are within the capabilities of a person of ordinary skill in the art. Such techniques are explained in the literature. See, e.g., J. Sambrook, E. F. Fritsch, and T. Maniatis, 1989, *Molecular Cloning: A Laboratory Manual, Second Edition*, Books 1-3, Cold Spring Harbor Laboratory Press; Ausubel, F. M. et al. (1995 and periodic supplements) *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells, and organisms comprising transgenic cells are referred to as "transgenic organisms."

"Transformed," "transduced," "transgenic," and "recombinant" refer to a host cell or organism into which a heterologous nucleic acid molecule has been introduced. The nucleic acid molecule can be stably integrated into the genome generally known in the art and are disclosed in Sambrook and Russell, infra. See also Innis et al. (1995); and Gelfand (1995); and Innis and Gelfand (1999). For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the terms "polynucleotide," "nucleotide," and "nucleic acid" are intended to be synonymous with each other. "Polynucleotide" generally refers to any polyribonucleotide or polydeoxyribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can been made to DNA and RNA; thus, "polynucleotide" embraces chemically, enzymatically, or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

The polynucleotides described herein may comprise DNA or RNA. They may be single-stranded or double-stranded. They may also be polynucleotides that include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described herein. Where the polynucleotide is single-stranded, it is to be understood that the complementary sequence of that polynucleotide is also included.

The terms "variant," "homologue," or "derivative" in relation to a nucleotide sequence include any substitution of, variation of, modification of, replacement of, deletion of, or addition of one (or more) nucleotides from or to the sequence.

As indicated above, with respect to sequence identity, a "homologue" has at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

In particular, there is at least 95% identity, more particularly at least 96% identity, more particularly at least 97% identity, more particularly at least 98% identity, more particularly at least 99% identity. Nucleotide homology comparisons may be conducted using techniques well known in the art. One suitable sequence comparison program is the GCG Wisconsin Bestfit program, which is known in the art. The default scoring matrix has a match value of 10 for each identical nucleotide and −9 for each mismatch. The default gap creation penalty is −50 and the default gap extension penalty is −3 for each nucleotide. Various other methods are known in the art on how to calculate sequence identity.

In one embodiment, the estrogen-responsive 5'-regulatory nucleotide of the present invention has at least 98.1% or more sequence identity to a sequence corresponding to SEQ ID NO:2, SEQ ID NO:3, or SEQ ID NO:4. In particular, the estrogen-responsive 5'-regulatory nucleotide has 98.2% or more, 98.3% or more, 98.4% or more, 98.5% or more, 98.6% or more, 98.7% or more, 98.8% or more, 98.9% or more, 99.0% or more or 99.1% or more, 99.2% or more, 99.3% or more, 99.4% or more, 99.5% or more, 99.6% or more, 99.7% or more, 99.8% or more, 99.9% or more sequence identity to a sequence corresponding to SEQ ID NO:2, SEQ ID NO:3, or SEQ ID NO:4.

Polymerase chain reaction (PCR) may be employed during the processes involved in producing and detecting the transgenic fish of the present invention. Known methods of PCR include, but are not limited to, methods using paired primers, nested primers, single specific primers, degenerate primers, gene-specific primers, vector-specific primers, partially mismatched primers, and the like.

In one aspect, the present invention also relates to an expression cassette for use in producing the transgenic fish of the present invention. The expression cassette of the present invention includes the following: (i) a reporter nucleotide sequence encoding a reporter protein; (ii) an estrogen-responsive 5'-regulatory nucleotide sequence isolated from a medaka fish, wherein the regulatory nucleotide sequence is operably linked 5' to the reporter nucleotide sequence to induce expression of the reporter protein in the presence of estrogen or an estrogen-like compound; and (iii) a 3'-regulatory region operably linked 3' to the reporter nucleotide sequence.

In one embodiment, the expression cassette of the present invention includes a 5'-regulatory nucleotide sequence isolated from a brackish medaka fish of the species *Oryzias melastigma*. For example, the 5'-regulatory nucleotide sequence can be derived from the promoter region of a choriogenin H gene of *Oryzias melastigma*, where the choriogenin H gene has a nucleotide sequence of SEQ ID NO:1.

In one embodiment, the expression cassette of the present invention can include a 5'-regulatory nucleotide sequence that is derived from the promoter region of the *Oryzias melastigma* choriogenin H gene, where the nucleotide sequence corresponds to (i) SEQ ID NO:2 (corresponding to a −4827 bp omChgH5'-upstream region); (ii) SEQ ID NO:3 (corresponding to a −750 bp omChgH5'-upstream region); and (iii) SEQ ID NO:4 (corresponding to a −350 bp omChgH5'-upstream region).

In another embodiment, the reporter nucleotide sequence of the expression cassette of the present invention encodes a reporter protein that is an autofluorescent protein. Suitable examples of autofluorescent proteins can include, without limitation, an enhanced green fluorescent protein (EGFP), a green fluorescent protein (GFP), a blue fluorescent protein (BFP), a yellow fluorescent protein (YFP), a red fluorescent protein (RFP), and the like.

In one embodiment, the expression cassette of the present invention can include a 3'-regulatory region that comprises an mRNA polyadenylation signal. A suitable mRNA polyadenylation signal can include, without limitation, the 3'-flanking region of a choriogenin H gene of a medaka fish (e.g., *Oryzias melastigma* and *Oryzias latipes*). In particular, the mRNA polyadenylation signal can include, without limitation, the 3'-flanking region of the choriogenin H gene that includes the 3'-UTR (untranslated region) and the polyadenylation tail sequences of the choriogenin H gene. More particularly, the 3'-regulatory region can include the nucleotide sequence of SEQ ID NO:5.

The present invention also relates to a transformation vector that contains the expression cassette of the present invention.

The present invention also relates to a host cell transduced with the expression cassette of the present invention.

The present invention also relates to a transgenic cell of an aquatic animal, where the transgenic cell includes at least one expression cassette of the present invention. As set forth herein, the transgenic cell can be from an aquatic animal that is a freshwater, saltwater, and brackish water fish. Suitable examples of such fish are discussed herein and include, for example, *Oryzias* species and *Danio* species.

The present invention also relates to a transgenic fish that contains at least one expression cassette of the present invention. The transgenic fish of the present invention exhibits an observable mark when exposed to a liquid medium containing an estrogen or an estrogen-like compound. The observable mark includes the reporter protein expressed by the at least one expression cassette. The observable mark is visible in vivo or in vitro. The transgenic fish can be of a freshwater, saltwater, or brackish water fish. As noted, suitable examples of such fish are discussed herein and include, for example, *Oryzias* species and *Danio* species. In a particular embodiment, the transgenic fish is at a stage of development that includes, without limitation, an embryo stage, a larva stage, and/or an adult stage. More particularly, the transgenic fish can be a male adult.

The "expression cassette" of the present invention can also be referred to as a "recombinant construct." Recombinant constructs are generally known in the art to contain an expression control sequence (e.g., the estrogen-responsive 5'-regulatory nucleotide sequence), which is operably linked to a reporter sequence. That means that a polynucleotide comprising an expression control sequence of interest is cloned in a recombinant construct, such that the expression control sequence is operably linked to a reporter sequence. In particular, the reporter is a heterologous sequence.

The methods for making the recombinant constructs are conventional. Such methods, as well as many of the other molecular biological methods used in conjunction with the present invention, are discussed, e.g., in Sambrook, et al. (1989), Molecular Cloning, a Laboratory Manual, Cold Harbor Laboratory Press, Cold Spring Harbor, N.Y.; Ausubel et al. (1995). Current Protocols in Molecular Biology, N.Y., John Wiley & Sons Davis et al. (1986), Basic Methods in Molecular Biology, Elseveir Sciences Publishing, Inc., New York; Hames et al. (1985), Nucleic Acid Hybridization, IL Press; Dracopoli et al. Current Protocols in Human Genetics, John Wiley & Sons, Inc.; and Coligan et al. Current Protocols in Protein Science, John Wiley & Sons, Inc.

Suitable reporter sequences will be evident to those of skill in the art. For example, a suitable reporter protein can include autofluorescent proteins and enzymes detectable by a histochemical method.

As indicated elsewhere herein, the fluorescent protein can include, without limitation, a green fluorescent protein (GFP), an enhanced green fluorescent protein (EGFP), a red fluorescent protein (CFP and Red FP, RFP), a blue fluorescent protein (BFP), a yellow fluorescent protein (YFP), and fluorescent variants of these proteins. The heterologous fluorescent gene may be, for example, a gene encoding DsRed2, ZsGreen1, and ZsYellow1. The heterologous fluorescent gene may also be any variation or mutation of these genes, encoding fluorescent proteins including green fluorescent protein (GFP), enhanced green fluorescent protein (eGFP), yellow fluorescent protein (YFP), enhanced yellow fluorescent protein (eYFP), blue fluorescent protein (BFP), enhanced blue fluorescent protein (eBFP), cyan fluorescent protein (CFP), and enhanced cyan fluorescent protein (eCFP).

According to another embodiment, the enzyme that is detectable by a histochemical method is chosen from the group composed of luciferase, β-galactosidase, β-glucuronidase, alkaline phosphatase, chloramphenicol acetyl transferase, and alcohol dehydrogenase. According to a particular embodiment, it is luciferase. The term "luciferase" is intended to denote all the proteins which catalyze or initiate a bioluminescent reaction in the presence of a substrate called luciferin. The luciferase according to the invention may come from many organisms or systems that generate bioluminescence (see U.S. Pat. No. 6,152,358). For example, the luciferase according to the invention may come from *Renilla* (U.S. Pat. No. 5,418,155 and U.S. Pat. No. 5,292,658) or from *Photinus pyralis* or from *Luciola cruciata* (U.S. Pat. No. 4,968,613).

Techniques to detect protein reporters, either directly (e.g., by measuring the amount of reporter mRNA) or indirectly (e.g. by measuring the amount and/or activity of the reporter protein) are conventional. Many of these methodologies and analytical techniques can be found in such references as Current Protocols in Molecular Biology, F. M. Ausubel et al., eds., (a joint venture between Greene Publishing Associates, Inc. and John Wiley & Sons, Inc.), Enzyme Immunoassay, Maggio, ed. (CRC Press, Boca Raton, 1980); Laboratory Techniques in Biochemistry and Molecular Biology, T. S. Work and E. Work, eds. (Elsevier Science Publishers B. V., Amsterdam, 1985); Principles and Practice of Immunoassays, Price and Newman, eds. (Stockton Press, NY, 1991); and the like.

For example, changes in nucleic acid expression can be determined by polymerase chain reaction (PCR), ligase chain reaction (LCR), Qβ-replicase amplification, nucleic acid sequence based amplification (NASBA), and other transcription-mediated amplification techniques; differential display protocols; analysis of northern blots, enzyme linked assays, micro-arrays and the like. Examples of these techniques can be found in, for example, PCR Protocols A Guide to Methods and Applications (Innis et al., eds, Academic Press Inc. San Diego, Calif. (1990)).

In a particular embodiment, the amount and/or activity of a reporter expression product (e.g., a protein) is measured. A fluorescent marker, such as EGFP, can be detected by detecting its fluorescence in the cell (e.g., in a brackish medaka fish embryo). For example, fluorescence can be observed under a fluorescence microscope. Reporters such as EGFP, which are directly detectable without requiring the addition of exogenous factors, are preferred for detecting or assessing gene expression during fish embryonic development. A transgenic fish embryo carrying a recombinant construct of the invention encoding an EGFP reporter can provide a rapid real time in vivo system for analyzing spatial and temporal expression patterns of developmentally regulated liver genes, and for determining the presence of an estrogenic compound.

The recombinant construct of the present invention can be cloned into a suitable vector. The vector can then be used, e.g., to propagate the recombinant construct. Generally, before introducing a recombinant construct of the invention into a fish embryo, it is desirable to remove the vector sequences. Preferably, the vector/construct is designed so that the recombinant construct can be excised with one or two appropriate restriction enzymes.

Large numbers of suitable vectors are known to those of skill in the art, and many are commercially available. The following vectors are provided by way of example: (i) bacterial vectors, including pQE70, pQE60, pQE-9 (Qiagen), pBS, pD10, phagescript, psiX174, pBluescript SK, pBSKS, pNH8A, pNH16a, pNH18A, pNH46A (Stratagene), pTRC99a, pKK223-3, pKK233-3, pDR540, pRIT5 (Pharmacia); and (ii) eukaryotic vectors, including pWLNEO, pSV2CAT, pOG44, pXT1, pSG (Stratagene) pSVK3, pBPV, pMSG, pSVL (Pharmacia). However, any other plasmid or vector may be used as long as it is replicable and viable in the host.

In one aspect, the present invention provides a method for detecting the promoter activity in a cell of an estrogen-responsive 5'-regulatory nucleotide sequence of the present invention. This can be done in a eukaryotic cell by introducing the recombinant construct into the eukaryotic cell, and detecting the presence and/or activity of the reporter sequence in the cell. A variety of eukaryotic cells can be used; suitable cells will be evident to the skilled worker. In particular embodiments, the reporter sequence encodes EGFP, and the eukaryotic cell is in or from a fish, such as a brackish medaka fish, or is in or from a brackish medaka fish embryo.

Many art-recognized methods are available for introducing polynucleotides, such as the constructs of the present invention, into cells. The conventional methods that can be employed, include, e.g., transfection (e.g., mediated by DEAE-Dextran or calcium phosphate precipitation), infection via a viral vector (e.g., retrovirus, adenovirus, adeno-associated virus, lentivirus, pseudotyped retrovirus or poxvirus vectors), injection, such as microinjection, electroporation, sonoporation, a gene gun, liposome delivery (e.g., Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), or other liposomes developed according to procedures standard in the art), or receptor-mediated uptake and other endocytosis mechanisms.

Methods for introducing the recombinant construct into a fish embryo are discussed in more detail elsewhere herein.

As used herein, "transgenic fish" refers to fish, or progeny of a fish, into which an exogenous recombinant construct has been introduced. A fish into which a construct has been introduced includes fish that have developed from embryonic cells into which the construct has been introduced. As used herein, an exogenous construct is a nucleic acid that is artificially introduced, or was originally artificially introduced, into an animal. The term artificial introduction is intended to exclude introduction of a construct through normal reproduction or genetic crosses. That is, the original introduction of a gene or trait into a line or strain of animal by cross breeding is intended to be excluded.

However, fish produced by transfer, through normal breeding, of an exogenous construct (that is, a construct that was originally artificially introduced) from a fish containing the construct are considered to contain an exogenous construct. Such fish are progeny of fish into which the exogenous construct has been introduced. As used herein, progeny of a fish are any fish which are descended from the fish by sexual reproduction or cloning, and from which genetic material has been inherited. In this context, cloning refers to production of a genetically identical fish from DNA, a cell, or cells of the fish. The fish from which another fish is descended is referred to as a progenitor fish. As used herein, development of a fish from a cell or cells (embryonic cells, for example), or development of a cell or cells into a fish, refers to the developmental process by which fertilized egg cells or embryonic cells (and their progeny) grow, divide, and differentiate to form an adult fish.

In one embodiment, a transgenic fish of the present invention is one whose somatic and germ cells contain at least one genomically integrated copy of a recombinant construct of the invention. The invention further provides a transgenic fish gamete, including a transgenic fish egg or sperm cell, a transgenic fish embryo, and any other type of transgenic fish cell or cluster of cells, whether haploid, diploid, triploid or other zygosity having at least one genomically integrated copy of a recombinant construct of the present invention.

As used herein, the term "embryo" includes a single cell fertilized egg (i.e., a zygote) stage of the organism. In particular, the recombinant construct is integrated into the fish's somatic and germ cells such that it is stable and inheritable (is stably transmitted through the germ line). The transgenic fish or fish cell preferably contains a multiplicity of genomically integrated copies of the construct; more specifically, the multiple copies of the construct are integrated into the host organism's genome in a contiguous, head-to-tail orientation.

Progeny of the transgenic fish containing at least one genomically integrated copy of the construct, and transgenic fish derived from a transgenic fish egg, sperm, embryo or other fish cell of the present invention, are also included in the present invention. A fish is "derived from" a transgenic fish egg, sperm cell, embryo or other cell if the transgenic fish egg, sperm cell, embryo or other cell contributes DNA to the fish's genomic DNA. For example, a transgenic embryo of the present invention can develop into a transgenic fish of the present invention; a transgenic egg of the present invention can be fertilized to create a transgenic embryo of the present invention that develops into a transgenic fish of the present invention; a transgenic sperm cell of the present invention can be used to fertilize an egg to create a transgenic embryo of the present invention that develops into a transgenic fish of the present invention; and a transgenic cell of the present invention can be used to clone a transgenic fish of the present invention. In some embodiments of the present invention, the transgenic fish is sterile. The present invention further includes a cell line derived from a transgenic fish embryo or other transgenic fish cell of the present invention, which contains at least one copy of a recombinant construct of the present invention. Methods of isolating such cells and propagating them are conventional.

In one embodiment, the disclosed transgenic fish of the present invention are produced by introducing a recombinant construct of the present invention into cells of a fish, particularly into embryonic cells, and more particularly into a single cell embryo. Where the transgene construct is introduced into embryonic cells, the transgenic fish is obtained by allowing the embryo to develop into a fish. Introduction of constructs into embryonic cells of fish, and subsequent development of the fish, are simplified by the fact that embryos develop outside of the parent fish.

The disclosed recombinant constructs can be introduced into embryonic fish cells using any suitable technique. Many techniques for such introduction of exogenous genetic material have been demonstrated in fish and other animals. These include microinjection (described by, for example, Culp et al. (1991) *Proc Natl Acad Sci USA* 88, 7953-7957), electroporation (described by, for example, Inoue et al. (1990), *Cell. Differ. Develop.* 29, 123-128; Muller et al. (1993), *FEBS Lett.* 324, 27-32; Murakami et al. (1994), *J. Biotechnol.* 34, 35-42; Muller et al. (1992), *Mol. Mar. Biol. Biotechnol.* 1, 276-281; and Symonds et al. (1994), *Aquaculture* 119, 313-327), particle gun bombardment (Zelenin et al. (1991), *FEBS Lett.* 287, 118-120), retroviral vectors (Lu et al (1997). *Mol Mar Biol Biotechnol* 6, 289-95), and the use of liposomes (Szelei et al. (1994), *Transgenic Res.* 3, 116-119).

Embryos or embryonic cells can generally be obtained by collecting eggs immediately after they are laid. It is generally preferred that the eggs be fertilized prior to or at the time of collection. This is particularly accomplished by placing a male and female fish together in a tank that allows egg collection under conditions that stimulate mating. After collecting eggs, one technique is that the embryo be exposed for introduction of genetic material by removing the chorion. This can be done manually or, particularly, by using a protease such as pronase. A fertilized egg cell prior to the first cell division is considered a one-cell embryo, and the fertilized egg cell is thus considered an embryonic cell.

After introduction of the transgene construct, the embryo is allowed to develop into a fish. This generally need involve no more than incubating the embryos under the same conditions used for incubation of eggs. However, the embryonic cells can also be incubated briefly in an isotonic buffer. If appropriate, expression of an introduced transgene construct can be observed during development of the embryo.

Fish harboring a transgene can be identified by any suitable means. For example, the genome of potential transgenic fish can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgene construct can be accomplished by Southern or Northern blotting. Also, detection can be achieved using polymerase chain reaction (PCR) or other sequence-specific nucleic acid amplification techniques.

After "founder" transgenic fish are identified, one can mate them to wild type fish to identify those fish which comprise the transgene in their germ cells. Transgenic fish of the present invention can be either male or female. A transgenic fish of the present invention can be hemizygous for the transgene, which is a particular state for maintenance of transgenic fish lines. Alternatively, hemizygous fish can be crossed with each other to produce homozygous fish or fish lines. Homozygous diploids can also be produced by other methods, e.g., interruption of the second meiotic divisions with hydrostatic pressure using a French press.

The disclosed recombinant constructs can be integrated into the genome of the fish. However, the disclosed transgene construct can also be constructed as an artificial chromosome. Such artificial chromosomes containing more that 200 kb have been used in several organisms. Artificial chromosomes can be used to introduce very large transgene constructs into fish. This technology is useful since it can allow faithful recapitulation of the expression pattern of genes that have regulatory elements that lie many kilobases from coding sequences.

In another embodiment, the present invention includes a genomically identical population of transgenic fish, each of whose somatic and germ cells contain at least one genomically integrated copy of a recombinant construct of the present invention. The genomically identical population is a unisex population and can be male or female. Particular embodiments of the genomically identical transgenic fish population are essentially as described for the transgenic fish of the present invention. In an alternative embodiment, the present invention includes a population of transgenic fish, i.e., an in-bred line, the members of which are not necessarily genomically identical but are homozygous with respect to genomically integrated constructs.

The present invention also relates to various methods of using the transgenic fish of the present invention. In particular embodiments, these methods involve the detection of the presence or absence of an estrogenic compound in a medium, particularly in a liquid medium. More particularly, such methods are based on the induced expression of the reporter gene (also referred to herein as the reporter nucleotide sequence) that is operably linked to an estrogen-responsive 5'-regulatory nucleotide sequence of the present invention (as described elsewhere herein). Generally, when a transgenic fish of the present invention is exposed to an estrogenic compound, the estrogen-responsive 5'-regulatory nucleotide sequence will induce the expression of the reporter gene. Expression of the reporter gene results in an observable mark on the transgenic fish, indicating the presence of an estrogenic compound. As used herein, an "estrogenic compound or substance" refers to estrogen or any estrogen-like compound or substance.

As used herein, a "liquid medium" can refer to a number of different liquids. For example, it can include a liquid or water sample into which a test substance of interest has been added. It can also include a liquid or water sample into which a test substance of interest has not been added. Particular examples of a liquid medium suitable for use in the methods of the present invention can include freshwater, brackish water, and saltwater from any liquid or water source (e.g., rivers, lakes, bays, ponds, streams, oceans, etc.), whether these sources are natural or man-made.

Some of the various methods of using the transgenic fish of the present invention are generally provided below and more specifically provided in the Examples section hereof.

One method of the present invention relates to a method of screening a liquid medium for an estrogenic substance. This method involves exposing a transgenic fish of the present invention to a liquid medium to be tested (i.e., to be tested for the presence of an estrogenic substance). After this exposing step, the method then involves determining whether or not the transgenic fish exhibits an observable mark produced by the induced expression of the reporter gene (contained in the transgenic fish). The presence of the observable mark indicates that the liquid medium contains an estrogenic substance.

In one embodiment of this method, the determining step can include in vivo autofluorescence microscopy, where the reporter gene encodes an autofluorescent reporter protein.

In another embodiment of this method, the method can further include quantifying the estrogen-like activity of a test substance identified to be an estrogenic substance according to the determining step, where the test substance is identified as being an estrogenic substance if the transgenic fish exhibits an observable mark.

In another embodiment of this method, the quantifying step includes (i) generating at least one image of the observable mark; and (ii) subjecting the at least one image of the observable mark to image analysis software to quantify the signal intensity of the observable mark.

Another method of the present invention relates to a method of screening for a compound having anti-estrogenic activity. This method involves the following steps: (a) providing a first transgenic fish and a second transgenic fish of the present invention, where the first and second transgenic fish are of the same species and at substantially the same developmental stage; (b) exposing the first transgenic fish to a first liquid medium, where the first liquid medium includes an estrogen or estrogen-like compound; (c) exposing the second transgenic fish to a second liquid medium, where the second liquid medium includes the first liquid medium and a test compound; and (d) comparing the quantified intensity of any observable mark exhibited by the first transgenic fish with the quantified intensity of any observable mark exhibited by the second transgenic fish, where a decrease in the quantified intensity of the observable mark in the second transgenic fish compared to that of the first transgenic fish indicates that the test compound has anti-estrogenic activity.

Another method of the present invention relates to a method for investigating the effect of an estrogenic compound on liver regeneration. Generally, this method involves performing a partial hepatectomy on an adult transgenic fish of the present invention, where the partial hepatectomy is effective to remove a portion of the liver of the transgenic fish; exposing the transgenic fish to a test liquid medium containing a test estrogenic compound; and analyzing the liver of the transgenic fish to detect any regeneration of liver tissue.

In one embodiment of this method, the analyzing step can include comparing liver regeneration parameters of the transgenic fish taken at the following stages: (i) before the partial hepatectomy; (ii) after the partial hepatectomy but before the exposing step; and (iii) after the partial hepatectomy and after the exposing step. Suitable liver regeneration parameters can include, without limitation, liver volume, liver shape, liver weight, and/or liver-to-body weight ratio. In one aspect, determining the presence and/or intensity of the observable mark exhibited by the transgenic fish is effective to assist in measuring the liver regeneration parameters. In a particular embodiment, the liver shape and liver volume parameters are measured by generating three-dimensional images of the liver using confocal microscopy combined with image analysis software.

Another method of the present invention relates to a method for investigating the effect of different estrogenic compounds on liver regeneration, as opposed to investigating a single estrogenic compound. Generally, this method involves the following steps: (a) providing a first transgenic fish and a second transgenic fish of the present invention, where the first and second transgenic fish are adults of the same species; (b) exposing the first transgenic fish to a first liquid medium that includes a first test estrogenic compound solution; (c) exposing the second transgenic fish to a second liquid medium comprising a second test estrogenic compound solution; (d) quantifying the intensity of any observable mark exhibited by the first transgenic fish and the second transgenic fish; (e) performing a partial hepatectomy on the first and second transgenic fish, where the partial hepatectomy is effective to remove a portion of the liver of the first and second transgenic fish; (f) repeating steps (b) through (d) of this method; and (g) analyzing the liver of the first and second transgenic fish to compare the effects of the estrogenic compounds contained in the first liquid medium and the second liquid medium on any regeneration of liver tissue.

In one embodiment of this method, the analyzing step can include comparing liver regeneration parameters of the transgenic fish taken at the following stages: (i) before the partial hepatectomy; (ii) after the partial hepatectomy but before the exposing step; and (iii) after the partial hepatectomy and after the exposing step. Suitable liver regeneration parameters can include, without limitation, liver volume, liver shape, liver weight, and/or liver-to-body weight ratio. In one aspect, determining the presence and/or intensity of the observable mark exhibited by the transgenic fish is effective to assist in measuring the liver regeneration parameters. In a particular embodiment, the liver shape and liver volume parameters are measured by generating three-dimensional images of the liver using confocal microscopy combined with image analysis software.

In another embodiment of this method, the method can further include separating hepatocytes exhibiting observable marks from other liver cells not exhibiting observable marks, where the separating is conducted using flow cytometry.

In another embodiment of this method, the method can further include conducting hepatocyte metabolomic and proteomic analyses of the liver of the first and second transgenic fish.

Provided below are particular embodiments of various aspects of the present invention, some of which have been generally described above.

Cloning of Brackish Medaka-Derived Choriogenin H Gene

In a particular embodiment of the present invention, the brackish medaka fish to be used in cloning a choriogenin H gene (omChgH) and the medaka fish to be used in introduction of the constructed transgenic gene are not particularly limited, as long as they belong to a species *Oryzias melastigma* (alternative name *Oryzias dancena*). The medaka fish used in this embodiment of the present invention were obtained from a commercial hatchery in Taiwan. The obtained medaka fish can be maintained in freshwater, brackish water, as well as seawater. In this embodiment of the present invention, the fish were maintained in 30 ppt artificial seawater at 28±1° C. with a constant light cycle of 14 h-light/8 h-dark and fed with commercial hormone-free flake food and brine shrimp (*Anemia salina*).

The *Oryzias melastigma*-derived estrogen-responsive choriogenin H gene promoter region used in this embodiment of the present invention is captured after sequential genome walks in Dra I and EcoR V genomic DNA libraries according to the manufacturer's instruction on the genome walking kit (BD Biosciences).

In this embodiment of the present invention, choriogenin H 3'-flanking region includes choriogenin H 3'-untranslated region (represented as UTR) and partial genomic DNA sequence downstream is isolated. To clone 3'-UTR downstream genomic sequence, choriogenin H exon-intron structure is identified. The choriogenin H 3'-downstream genomic nucleotide is isolated using inverse-PCR (polymerase chain reaction). A sequence of ca. 800 bp choriogenin H 3'-flanking region from transcription terminal is isolated and deposited at GenBank with Accession No. DQ778335.

Construction of Transgene Plasmid

In one embodiment of the present invention, the *Oryzias melastigma*-derived choriogenin H promoter region cloned by the aforementioned method, EGFP cDNA sequence (i.e., the reporter nucleotide sequence), and *Oryzias melastigma*-derived choriogenin H 3'-flanking region cloned by the aforementioned method, or poly (A) signal of other genes, are introduced into a vector. The introduction of these nucleotide sequences into a vector can be performed in accordance with a known genetic engineering process. In this manner, it is possible to construct a recombinant vector into which the *Oryzias melastigma*-derived choriogenin H promoter region linked with EGFP encoding region are inserted.

In this and other embodiments of the present invention, the vector to be used is not particularly limited, as long as the promoter sequence, encoding sequence, and poly (A) signal sequence are operably inserted.

Production of Transgenic Brackish Medaka Fish

In one embodiment of the present invention, the recombinant transgene plasmid constructed as mentioned above is linearized and transferred into the plasma of brackish medaka fertilized eggs, thereby making the transgenic brackish medaka fish capable of expressing the EGFP regulated by the inserted omChgH promoter in an estrogen-dependent manner, just like its internal omChgH does. As the brackish medaka fertilized egg to be transferred in this and other embodiments of the present invention, embryos at one-cell stage within half an hour after fertilization are used. The recombinant transgene sequence can be transferred into the single-cell of fertilized eggs by means of microinjection.

To get one-cell stage brackish medaka eggs, a mating tank system can be used to separate male and female fish the day before microinjection. Male and female fish are released to mate by pulling the separator away from the mating tank before proceeding microinjection. In an embodiment of the present invention, the fertilized eggs which have been subjected to microinjection are raised at 28±1° C. for 2-3 months till they become adult fish.

Adult fish having the introduced gene integrated into its genome can be screened by the following methods. First, adult fish mate with wild fish and DNA is extracted from their eggs. The extracted DNA is then PCR amplified using EGFP specific primers, and the amplified product is subjected to electrophoresis. Second, adult fish mate with wild fish. Their eggs are raised to hatch out and then exposed to estrogen or estrogen-like chemical substances overnight or longer. These larvae are then checked under fluorescent microscope equipped with GFP filter set to see whether there is GFP expression in the liver. By these two methods, brackish medaka fish having the introduced nucleotide sequence integrated into the genome of a germ cell (sperm or egg) can be successfully identified.

Subsequently, the brackish medaka fish containing the introduced nucleotide sequence into the genome of a germ cell is mated with wild type fish. Their progeny inherit the introduced nucleotide sequence and can be screened for the introduced nucleotide sequence by the aforementioned two methods. This fish can pass the transgene from generation to generation. Such fish include a desired transgenic brackish medaka fish of the present invention.

Without any treatment, the expression of the introduced EGFP in the transgenic brackish medaka is restricted to the liver of reproducing females that synthesize high concentration of estrogen, and no EGFP expression is observed in the liver of embryos, larvae and male fish. However, when the transgenic brackish medaka fish is exposed to estrogen or estrogen-like chemical substances, the EGFP transgene can also be induced to express in the liver of embryo, larvae and male fish. The expression profile of the introduced EGFP is consistent with the internal expression profile of omChgH in this brackish medaka (X. Chen et al. Ectoxicol. Environ. Saf. 71:200-208 (2008)), except that omChgH protein is a secretary protein that will transport to ovary through blood circulation after its synthesis in the liver, while EGFP is not a secretory protein and will stay in the liver after its synthesis. As the transgenic brackish medaka female fish express EGFP without any outer induction, non-EGFP-expressing embryo, larvae and male transgenic brackish medaka fish are preferably to be used to test estrogen like activity.

Due to high translucency of the brackish medaka fish during embryo and early larvae stage, the response of the transgenic brackish medaka fish to estrogen or estrogen-like substances at these stages can be easily observed in vivo using a fluorescence microscope. The early stage larvae (before 15 days past fertilization), which are most translucent, are a particularly good stage for testing estrogen-like activity in vivo. Further, if the estrogen or estrogen-like chemicals treated transgenic brackish medaka fish are transferred to clean water, the induced EGFP signal will gradually disappear in around one week, and the EGFP can be re-induced if the fish is put back to solution containing estrogen or estrogen-like chemical substances.

Method of Detecting Estrogen-Like Activity

In one embodiment of the present invention, whether estrogen or estrogen-like substances are present or not in a test water sample can be easily detected by exposing the transgenic brackish medaka fish of the present invention into the test water for a period of time and then observing the exposed transgenic fish under fluorescence microscope to see whether EGFP expression is induced in the liver or not.

As used herein, "test water" can be, but is not restricted to, water collected from the environment (e.g., river, estuary, brackish, etc.), which may contain one or more than one estrogen-like substance, or water added with one substance (e.g., pharmaceuticals, cosmetics, food stuff, etc.), which may contain estrogen or estrogen-like substances, or water added with one or more than one chemical to be tested, which may act separately, or in combination, like estrogen.

When testing a potential estrogenic chemical or mixture substance, in one embodiment of the present invention, testing can be done in a serial of concentrations, since each chemical substance has varying toxicity as well as potential estrogen-like activity; additionally, it is also suitable and useful to include an estrogen (E2) exposure of known concentration as a reference to measure the estrogen-like activity and calculate the estrogen equivalency of the test chemical substance. Exposing the transgenic brackish medaka fish to the test water for 1-2 days will be long enough for most samples. The exposure condition may be the same as that of raising brackish medaka fish.

One advantage of this method is that estrogen-like activity of test water can be quantified by measuring the induced EGFP signal intensity in the liver. After appropriate time of exposure, fish exposed to test water of different estrogen-like activity will express varying quantities of EGFP in the liver, which can be easily differentiated by observation under fluorescence microscope. In one embodiment, to quantify the induced EGFP signal, fluorescence image of the EGFP expressing liver will be recorded using a camera connected to the fluorescence microscope, and the EGFP signal intensity in the liver area can be analyzed by image analysis software. When exposure to estrogen of known concentration is also included as reference, the estrogen-like activity of the test water can be converted to estrogen potency equivalent.

As embodiments of the transgenic brackish medaka fish of the present invention can be used to easily monitor the estrogen-like activity of test water, this method can be used to rapidly screen potential estrogenic chemical substances, as well as evaluate the combined estrogen-like activity of chemical mixtures. When chemical substances are tested separately as well as in combination, the mode of action of the chemical substances can be predicted. For example, some chemical substances may act estrogenically and some may act anti-estrogenically. When chemical substances of the same action mode, for example, estrogenic mode, are tested together, their total estrogen-like activity will be higher than that of any one of them alone. However, when estrogenic and anti-estrogenic chemical substances are mixed together, the final estrogen-like activity of the mixture will be lower than that of the estrogenic chemical substance.

Advantages of the Transgenic Brackish Medaka Fish Detection System

The various aspects of the present invention provide a number of advantages. Some of these advantages are described below, and such descriptions are not meant to include all of the advantages.

First, there are many advantages for using the transgenic fish of the present invention to detect estrogenic agents or events. The aqueous environment is the ultimate sink for natural and anthropogenic chemicals (J. P. Sumpter, Toxicol. Lett. 102-103:337-342 (1998)). Fish inhibit in water are environmentally relevant models for health risk assessment of aquatic environments. Despite the evolutionary distance between fish and humans, fish share most developmental pathways, physiological mechanisms and organ systems with humans (A. R. Cossins and D. L. Crawford, Nature Rev. Genet. 6:324-333 (2005)); and, thus, occupy a prominent position in the field of toxicology, development as well as biomedical studies. Fish are easy to handle, manipulate and observe, and are increasingly being used as an alternative, non-mammalian animal model to reduce or replace traditional mammalian models in research and testing. Fish, particularly small fish such as Japanese medaka (*Oryzias latipes*) and zebrafish (*Danio rerio*), have been widely used as laboratory model species in different fields of research. Advances made with these two aquarium fish models have led to the complete sequencing of their genomes (E. Ekker et al., Zebrafish 4, 239-251 (2003); M. Kasahara et al., Nature, 447:714-719 (2007)), and numerous transgenic fish strains have been established for these two research models, several of which have been aimed to detect estrogen-like activity as the present invention does (T. Kawamura, Zoolog. Sci. 19(2): 1355-1361 (2002); T. Ueno et al., Mech. Dev. 121(7-8):803-15 (2004); K. Krauchi et al., Environ. Sci. Technol. 39(8): 2762-8 (2005); Z. Zeng et al., Environ. Sci. Technol. 39(22): 9001-8 (2005); T. Hano et al., Environ. Sci. Technol. 41(4): 1473-9 (2007); M. A. Salam et al., J Environ Sci Health A Tox Hazard Subst Environ Eng. 43(3):272-7 (2008); J. Legler et al., Environ. Sci. Technol. 34:4439-4444 (2000); S. K. Tong et al., Genesis, 47(2):67-73 (2009)).

Second, it is advantageous to use fluorescence protein gene as reporter gene, through which the estrogen-like activity can be monitored by in vivo measurement of reporter gene expression without sacrificing the fish. Of these transgenic strains developed to detect estrogen-like activity, 3 strains used fluorescence protein reporter gene (T. Ueno et al., Mech. Dev. 121(7-8):803-15 (2004); K. Krauchi et al., Environ. Sci. Technol. 39(8):2762-8 (2005); Z. Zeng et al., Environ. Sci. Technol. 39(22):9001-8 (2005)), and have demonstrated its incomparable advantage for in vivo monitoring. However, none of these strains is sensitive enough to monitor the estrogen-like activity of environmental water samples without any concentration processing.

Third, the host organism can be selected to provide various advantages. For example, brackish medaka (*Oryzias melastigma*) shares most of the advantages that laboratory models zebrafish (*Danio rerio*) and Japanese medaka (*Oryzias latipes*) have, while possessing the advantage to thrive in varying salinity environment ranging from freshwater to seawater. The adaptability to a wide range of salinity makes this fish a universal model for both freshwater and seawater studies. And previous studies showed that research techniques and resources for this new model can be easily adapted from well established models such as zebrafish and Japanese medaka (X. Chen et al., Comp. Biochem. Physiol. C. Toxicol. Pharmacol. 149:647-655 (2009)).

Fourth, is that an estrogen-dependent liver-specific gene, omChgH, is identified and used in various embodiments of the present invention. omChgH is an egg envelope protein. The term "estrogen-dependent" used herein means this gene only expresses in the presence of estrogen or estrogen-like chemical substances. The term "liver-specific" used herein means the expression of this gene is restricted exclusively to the liver, not in any other organs. Under normal circumstances (in clean water without any treatment), this gene only expresses in reproducing female when internal estrogen concentration is high, but not in embryo, larvae and male fish (X. Chen et al. Ectoxicol. Environ. Saf. 71:200-208 (2008)), in which internal estrogen level is almost undetectable. However, in the presence of external estrogen or estrogen-like chemical substances, this gene can also be induced to express in non-expressing embryo, larvae and male fish. Thus, using fluorescence protein gene as reporter marker regulated by the promoter of omChgH, the induced expression of omChgH gene will be represented as fluorescence protein in the liver, which can be easily detected under fluorescence microscope.

As noted above, in one aspect, the present invention relates to the development of a transgenic fish containing a genomically integrated nucleotide sequence comprising a fluorescence protein gene as reporter marker regulated by an estrogen-responsive promoter.

EXAMPLES

The following examples, while exemplary of the present invention, are not to be construed as specifically limiting the invention. Accordingly, variations and equivalents, now known or later developed, that would be within the purview of one skilled in the art are to be considered to fall within the scope of this invention.

Example 1

Development of a Transgenic Fish

Preparation of Brackish Medaka Genomic DNA

Genomic DNA (represented as gDNA) was extracted from an adult female with intestine dissected out. The sample was pestled in liquid nitrogen to small particles and incubated with 10 ml DNA extraction solution (150 mM NaCl, 0.5% sodium dodecyl sulfate (SDS), 25 mM ethylenediaminetetraacetic acid (EDTA), 10 mM Tris-HCl, pH 8.0) and 1% proteinase K at 45° C. for more than 4 h. Same volume phenol was added to the solution and mixed by slow rotation for 0.5 h. After 2,000 rpm centrifugation for 10 min, aqueous phase containing gDNA was transferred to a new polytron tube (50 ml) and mixed with the same volume of phenol/chloroform on a rotor for 10 min. Solution was then centrifuged at 2,000 rpm for 10 min, and aqueous phase was transferred to a new tube. gDNA solution was further purified by same volume of chloroform followed by 5 min centrifugation at 2,000 rpm. Aqueous phase was transferred to a new tube and gDNA was precipitated out by absolute ethanol. gDNA was carefully picked out using transfer tips, dissolved in nuclease-free water and kept at −20° C.

Cloning Brackish Medaka-Derived omChgH Gene Promoter Region

The 5'-flanking region of choriogenin H gene was captured after two rounds of genome walking according to the manufacturer's instructions (BD Biosciences). Nested PCR amplifications were performed using two adaptor-specific primers (GW-AP1: 5'-GTAATACGACTCACTATAGGGC-3' (SEQ ID NO:6), outer and GW-AP2: 5'-ACTATAGGGCACGCGTGGT-3' (SEQ ID NO:7), inner; provided in the kit) in combination with two anti-sense gene specific primers (represented as GSPs). GSPs used in the first genome walking in Dra I gDNA library were outer: 5'-AACGTGTTGAGGGTCCTGCGGCTTC-3' (SEQ ID NO:8) and inner: 5'-CTGTGGATAGTATGGAGGGTATGGAACC-3' (SEQ ID NO:9); and GSPs for the second genome walking in EcoRV gDNA library were designed based on the result of the first genome walking, there were outer: 5'-GTGTAATGGATGTGGACTTTTTCTATAAGACAACC-3' (SEQ ID NO:10) and inner: 5'-CCCAAAATGCATGTGCAGCTGATGGC-3' (SEQ ID NO:11). A 50-μl PCR reaction contained 5 μl of 10×PCR buffer, 1 μl of dNTP (10 mM), 1 μl of GSP (10 μM), 1 μl of adaptor primer (10 μM), 5 μl of 1/50 diluted adaptor-ligated genomic library (for primary PCR) or 1/500 diluted primary PCR product (for secondary PCR) and 1 μl of 50×BD Advantage 2 polymerase mix (BD Biosciences). The amplification profile for both primary and secondary PCRs consisted of 5 cycles of 94° C. for 15 s and 72° C. for 3 min, 5 cycles of 94° C. for 15 s and 70° C. for 3 min, and 25 cycles of 94° C. for 15 s and 68° C. for 3 min. The second PCR products were separated by electrophoresis, and the sharpest band was isolated, purified using Wizard® SV Gel and PCR Clean-up System (Promega), cloned to pGEM-T Easy Vector (Promega) and identified by commercial sequencing service (Tech Dragon).

Cloning of Brackish Medaka-Derived omChgH Gene 3'-Flanking Region

Inverse-PCR was performed to clone omChgH 3'-flanking region. After restriction endonuclease analysis of cloned coding region genomic DNA sequence (GenBank Accession No. EF392365) of omChgH gene, Nde I gDNA library was constructed by Nde I (Takara) digestion followed by T4 DNA ligase (Takara) ligation. Forward (5'-GAAAATCTGTTTCATCATGGTTCAG-3') (SEQ ID NO:12) and Reverse (5'-TTCACAACTGGTACCCTGTCCTGG-3') (SEQ ID NO:13) primers were designed near omChgH coding region 3'-end and upstream 5'-Nde I cutting site, respectively. Reactions were performed in a 50-μl volume containing 5 μL 10×PCR buffer, 1 μL dNTP (10 μM), 1 μL each primer (10 μM) and 1 μL Taq enzyme (5 U/μL; Takara). The PCR thermal profile consisted of an initial denaturation at 95° C. for 4 min, followed by 35 cycles of 95° C. for 30 s, 60° C. for 30 s and 72° C. for 1 min. The amplicon was identified using the same method as omChgH 5'-flanking region.

Preparation of Transgenic Plasmids omChgH5'-EGFP-olChgH3' plasmids construction: Totally 6595 bp of choriogenin H 5'-upstream region (GenBank Accession No. EF392365) from transcription initiation site was captured after sequential genome walks in Dra I and EcoR V gDNA libraries. In this embodiment, the plasmid ChgH-GFP (K. Krauchi et al., Environ. Sci. Technol. 39(8): 2762-8 (2005)) was used as vector. In this vector, Japanese medaka (*Oryzias latipes*) derived choriogenin H promoter region (represented as olChgH5') and 3'-flanking region (represented as olChgH3') were integrated, between which EGFP coding region was ligated. For easier following, this vector is represented as olChgH5'-EGFP-olChgH3'. After restriction sites analysis of both vector and omChgH 5'-upstream region, omChgH 5'-upstream region from −4827 to +15 from transcription initiation site was amplified using primers with built-in restriction sites: Forward (5'-TGCATG GCATGC TTAATTAA CTGCAG CCCGGG GTCGAC TCGTAC-CTCCAAAACCCAAC-3') (SEQ ID NO:14), Sph I, Pac I, Pst I, Sma I and Sal I restriction sites were underlined sequentially) and reverse (5'-CTCCAGTGCCTTG CCATGGT-3') (SEQ ID NO:15); Nco I site was underlined and translation start code was in bold). PCR fragment was subcloned into Sph I and Nco I restriction enzyme cutting sites of the olChgH5'-EGFP-olChgH3' vector to construct omChgH5'-EGFP-olChgH3' plasmid.

Additionally, two deletion mutants containing omChgH 5'-upstream region from −750 to +15 and from −350 to +15 were also constructed by PCR amplification and enzyme digestion, respectively, using omChgH5'-EGFP-olChgH3' plasmid as a template. The primers used for PCR amplification were 5'-TCGA CTGCAGTGCTCTCACTCTATGGGGTTC-3' (SEQ ID NO:16) (Pst I site was underlined, forward) and 5'-CTC-CAGTGCCTTGCCATGGT-3' (SEQ ID NO:17) (Nco I site was underlined, reverse). The amplicon then replaced the −4827 omChgH5' region of omChgH5'-EGFP-olChgH3' at Pst I and Nco I sites of omChgH5'-EGFP-olChgH3'. −350 omChgH 5'-EGFP-olChgH3' fragment was obtained by Xho I and EcoR I digestion of −4827 omChgH 5'-EGFP-olChgH3' plasmid.

omChgH5'-EGFP-SV40 Plasmid Construction: SV40 polyadenylation signal (represented as SV40 polyA) was amplified from DsRed2-1 vector (Clontech) by 5'-AGCTAC-TAGTCCATCTACATGGCCAAGAAG-3' (SEQ ID NO:18) (forward) and 5'-ATTTTGCCGATTTCGGCCTATTGGT-3' (SEQ ID NO:19) (reverse) primers, and ligated to pGEM®-T Easy vector for amplification. After digestion of by Not I and EcoR I, SV40 polyA replaced olChgH3' region in omChgH5'-EGFP-olChgH3' plasmid to construct plasmid omChgH5'-EGFP-SV40.

omChgH5'-EGFP-omChgH3' plasmids construction: A sequence of ca. 800 bp omChgH 3'-flanking region from transcription terminal (GenBank Accession No. DQ778335) was cloned by inverse-PCR described previously. For omChgH5'-GFP-omchgH3' construction, omChgH 3'-UTR was amplified using forward (5'-TGCAGCGGCCGCCTGT-GAACCGACAGAAG-3') (SEQ ID NO:20) with reverse (5'-CACGGATGTGTGTGTTTACC-3') (SEQ ID NO:21) primers, and 3'-flanking region was cloned by Forward (5'-GAAAATCTGTTTCATCATGGTTCAG-3') (SEQ ID NO:22) with Reverse (5'-TTCACAACTGGTACCCTGTC-CTGG-3') (SEQ ID NO:23) primers. 3'-UTR and 3'-flanking region were then ligated using BD In-Fusion™ Dry-Down PCR Cloning Kits (Clontech) according to the instruction. omChgH translation stop codon downstream region was then PCR amplified by forward (5'-TGCAGCGGCCGCCTGT-GAACCGACAGAAG-3') (SEQ ID NO:24) in combine with Reverse (5'-TTCACAACTGGTACCCTGTCCTGG-3') (SEQ ID NO:25) primers. Amplicon was then ligated into pGEM®-T Easy vector for amplification. This sequence was then subcloned into Not I and EcoR I sites of omChgH5'-GFP-omChgH3' or omChgH5'-GFP-SV40 plasmids to form omChgH5'-GFP-omChgH3' plasmids.

Microinjection of Fish Embryos

Fish embryos were microinjected generally in accordance with Kinoshita et al. (Aquaculture, 143(3-4): 267-276 (1996)) with modifications. In order to maximize incorporation frequency of the transgene and reduce the degree of mosaicism in the founders, transgene solution was microinjected into the plasma of fertilized eggs at the one-cell stage. For easy collection of newly fertilized eggs, a male and a female fish was separated in each mating tank by a separator the day before microinjection. Before microinjection, remove the separator and freshly fertilized eggs can be collected directly from the belly of female fish using a plastic dropper. Eggs were separately from each other by using two fine forceps grasping filaments of embryos and rotating against each other. Microinjection was performed as fast as possible and the timing was rigidly controlled within 30 min past fertilization.

Injections were performed with the aid of stereomicroscope or compound microscope, micromanipulator, and oil or gas pressurized injection apparatus. Embryos were held in interstice of self-made glass cement holder on a glass slide. Transgenic DNA constructs were linearized, dissolved in 10 mM phosphate buffer (pH 7.5) containing 1 mM EDTA, 137 nM NaCl, 3 mM KCl. Linearized transgenic DNA fragments were injected at concentration ranging from 10 to 50 ng/μL.

Promoter Activity of omChgH 5'-Upstream Region

To analyze a region responsible for omChgH gene regulation, fragments containing three different sizes ranging from 4827 bp to 350 bp of omChgH 5'-upstream region fused with EGFP reporter gene were injected into one-cell *O. melastigma* embryos. GFP transient expression was observed in most embryos initiated at 3 days after injection. Hatchlings survived from microinjected embryos were exposed to 5.1 nM E2 for 24 h, and GFP expression was observed using fluorescence stereomicroscope. The incidence of GFP-expressing hatchlings for each construct was calculated (FIG. 1). Though the percentage of GFP fluorescence-positive fish varied slightly, omChgH5'-EGFP-olChgH3' constructs containing 4827 bp (−4827) and 758 bp (−758) 5'-upstream region of omChgH gene, respectively, were suggested to have the same activity at promoting the estrogen-dependent liver-specific expression of the downstream EGFP gene. However, obvious decrease of promoter activity was observed from −758 to −350 omChgH5'-EGFP-olChgH3' constructs, suggesting the existence of certain cis-regulatory element(s) located from −758 to −350 of omChgH 5'-upstream region. While the presence of GFP-positive hatchlings demonstrated that 350 bp omChgH 5'-upstream region had the ability to regulate the estrogen-dependent liver-specific expression of its downstream gene.

Computer analysis identified putative cis-elements including one 5'-ERE-half site (at nt. Position −18), one C/EBP binding site (at nt. Position −158) and one estrogen-response element (ERE; at nt. Position −253) located within the first 350 bp 5'-upstream region, and another C/EBP binding site (at nt. Position −494) between −758 and −350 region of omChgH gene, respectively. The promoter activity demonstrated by −350 omChgH5'-GFP-olChgH3' construct suggests that some or all the three putative cis-elements identified within the first 350 bp 5'-upstream region are important for the regulation of the estrogen-dependent liver-specific expression of the downstream gene. While the obvious decrease of GFP-positive hatchling incidence from −758 to −350 omChgH5'-GFP-olChgH3' construct indicates that the C/EBP binding site at nt. Position −494 of omChgH is important for high cis-regulation of the estrogen-dependent liver-specific expression of downstream gene.

Regulation Effects of omChgH 3'-Flanking Region

Figure 2:
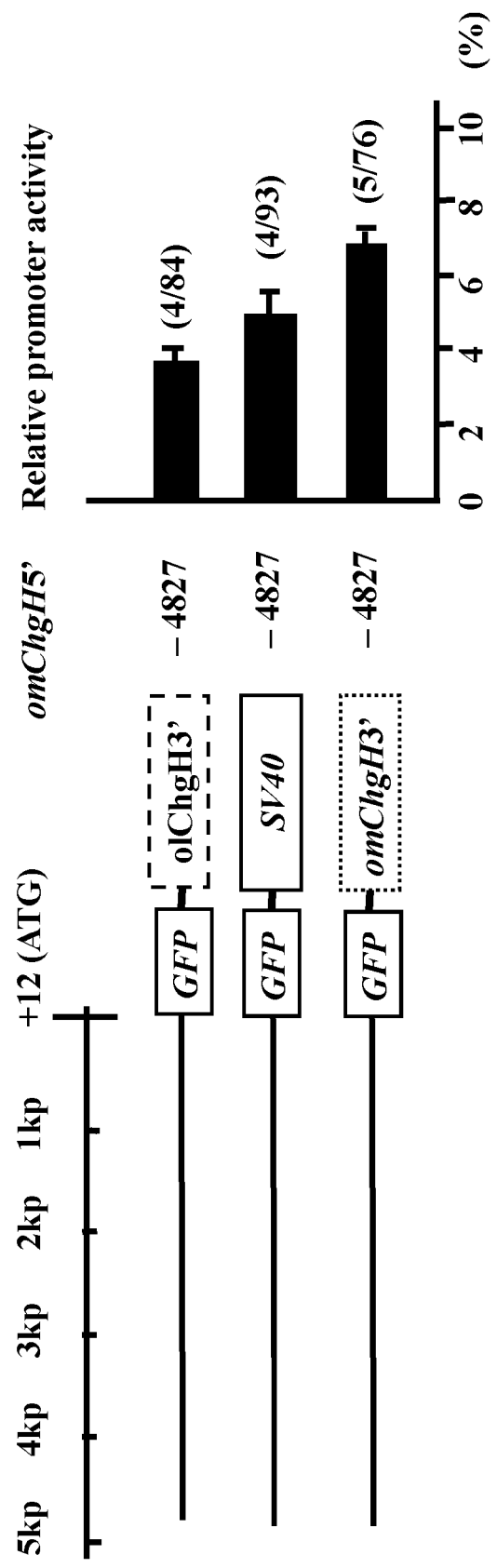
FIG. 2 depicts the effects of mRNA polyadenylation signal of different genes on the relative promoter activity of nucleic acid omChgH promoter-EGFP represented by the frequency of GFP positive larva derived from embryos injected with nucleic acid comprising the omChgH promoter-EGFP (enhanced green fluorescence protein) flanked by olChgH, SV40 or omChgH 3'-flanking region in response to 17β-estradiol.

As to some genes (e.g. vasa, nano), the 3'-flanking region is indispensable for the stability and localization of their mRNAs (M. Tanaka et al., Proc. Natl. Acad. Sci. U.S.A., 98(5): 2544-2549 (2001); M. Koprunner et al., Genes Dev. 15(21):2877-2885 (2001); H. Kurokawa et al., Dev. Growth Differ. 48(3):209-221 (2006)). In this embodiment, the importance of homogenous 3'-flanking region in omChgH transgenic studies was analyzed. olChgH3' of omChgH5'-GFP-olChgH3' fragment was replaced by SV40 polyA and omChgH3'-flanking region, respectively. These fragments were then injected into one-cell *O. melastigma* embryos and observation of estrogen-dependent GFP expression during hatchling stage was carried out as previously described and the results are summarized in FIG. 2. Flanked by SV40 polyA, −4728 omChgH5'-GFP DNA fragment demonstrated the ability to regulate the estrogen-dependent liver-specific expression of GFP fluorescence, and the GFP-positive hatchling incidence was even a little higher than that when it was flanked by olChgH3' but lower than that when it was flanked by omChgH3'. Additionally, higher GFP-positive hatchling incidences also observed in −750 and −350 omChgH5'-GFP-omChgH3' constructs than that of their accordingly omChgH5'-GFP-olChgH3' constructs (FIG. 1). These strongly indicate that homogenous 3'-flanking region is important for the high promoter activity of omChgH5'-GFP transgenic constructs, and the putative elements identified within the 3'-flanking region may explain the difference.

Moreover, results showed that similar promoter activity was observed between −4728 and −758 omChgH5'-GFP-omChgH3' constructs, while obvious decrease of promoter activity was observed in −350 omChgH5'-GFP-omChgH3' construct (FIG. 1). This further confirmed previous results (FIG. 1) that 350 bp omChgH 5'-upstream region was sufficient for regulating the estrogen-dependent liver-specific expression of its downstream gene, while the C/EBP binding site at nt. Position −494 of omChgH enhances the promoter activity.

Identification of Transgenic Fish

Injected embryos were raised for ca. 2-3 months to adult fish. These founders (F0) were then mated with wild-type fish individually. Their embryos were collected for genomic DNA extraction using Accuprep genomic DNA Extraction Kit (Bionner, Korea), and the presence of EGFP transgene was tested by PCR using EGFP specific primers (forward: 5'-TGCTGCCCGACAACCACTACC-3' (SEQ ID NO:26) and reverse: 5'-TTACTTGTACAGCTCGTCCATGC-3' (SEQ ID NO:27)). More embryos of EGFP-positive founders (F0) were collected and progenies (F1) carrying the EGFP transgene were screened by green fluorescence mark after exposure to estrogen (17β-estradiol, 5.1 nM) during hatchling stage. F1 fish expressed EGFP in response to estrogen were stable germ-line transgenic fish that can transfer the transgene to their progenies. Totally 11 germ-line transgenic fish strains were identified. Exposed to the same concentration of estrogen, the transgenic fish strain that showed most sensitive to estrogen was selected for detail analysis.

Transgene EGFP Expression

Figure 3:
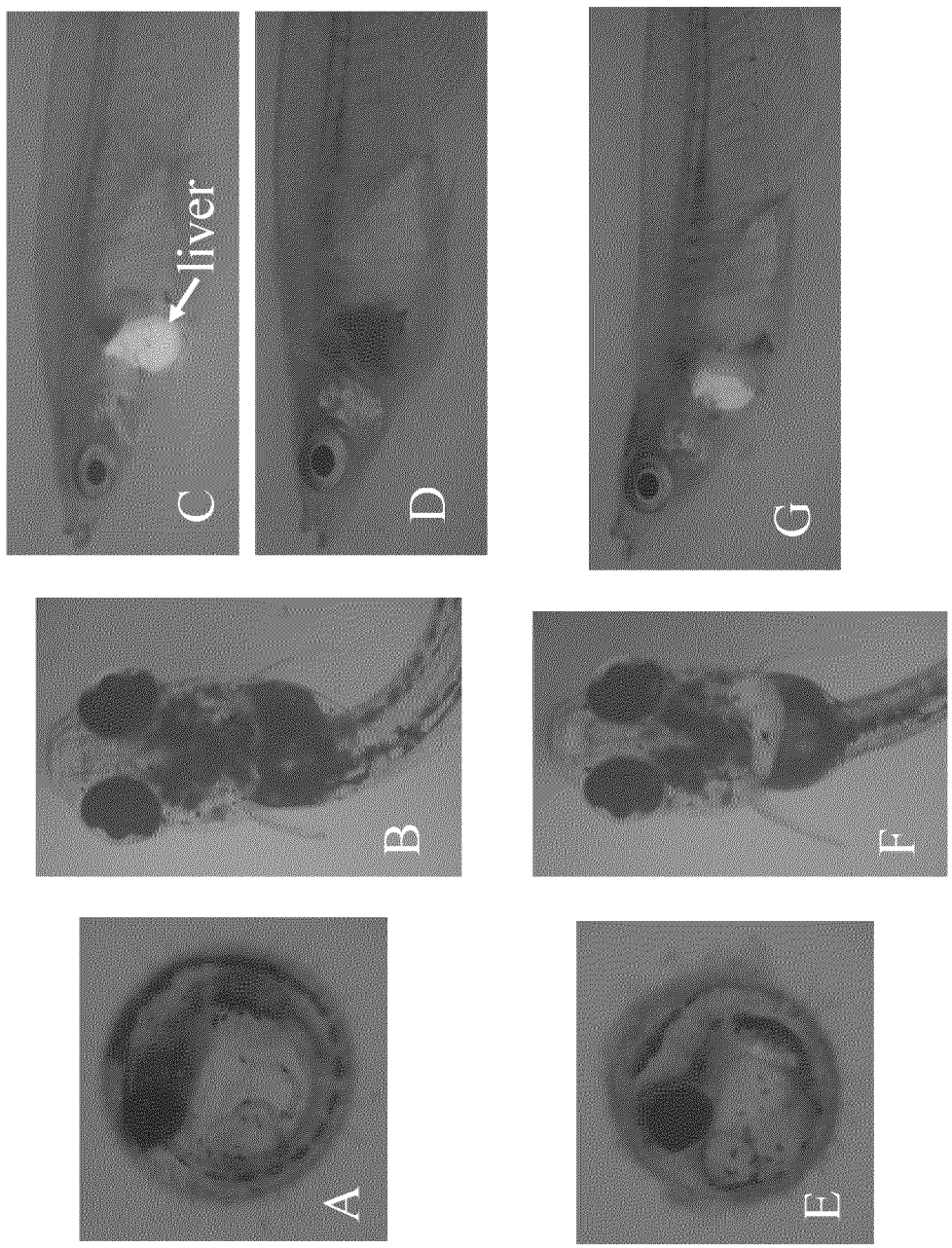
FIGS. 3A-3G depict the native and induced expression of transgene GFP in transgenic fish produced by introduction of a nucleic acid sequence including the omChgH promoter-EGFP transgene. The expression of GFP is exclusively restricted to the liver of adult female fish (FIG. 3C), but not embryo (FIG. 3A), larva (FIG. 3B), or male fish (FIG. 3D).

Without any treatment, the expression of the introduced EGFP in the transgenic brackish medaka is restricted to the reproducing females which synthesize high concentration of estrogen, and no EGFP expression is observed in the liver of embryos, larvae and male fish (FIG. 3). However, when the transgenic brackish medaka fish is exposed to estrogen or estrogen-like chemical substances, EGFP expression can also be induced in the liver of embryos, larvae and male fish (FIG. 3). The expression profile of the introduced EGFP is consistants with the internal expression profile of omChgH in this brackish medaka (X. Chen et al. Ectoxicol. Environ. Saf. 71:200-208 (2008)), except that omChgH protein is a secretary protein and will transport to ovary through blood circulation after its synthesis in the liver, while EGFP is not a secretary protein and will stay in the liver after its synthesis. As the transgenic brackish medaka female fish express EGFP without any outer induction, it is not easy to differentiate inner EGFP expression and induce EGFP by estrogen-like chemical substances. The non-EGFP-expressing embryo, larvae and male transgenic brackish medaka fish, however, serves as great candidate to monitor estrogen-like activity, which is presented as green fluorescence, especially newly hatched larvae, which swims, does not feed and is the most translucent, is the best stage for estrogen-like activity monitoring.

Example 2

Estrogen Exposure Experiments

Figure 4:
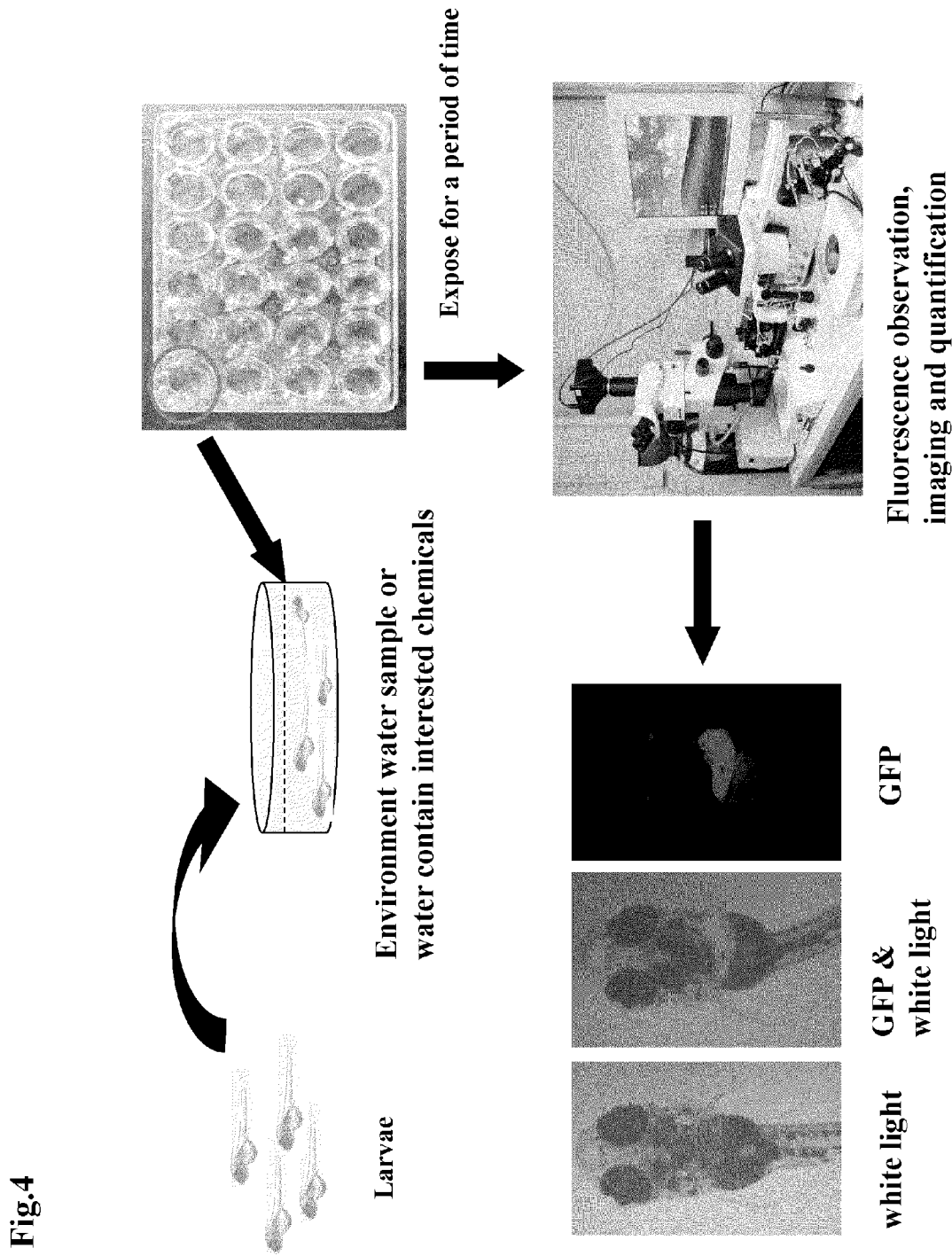
FIG. 4 depicts a flowchart of one embodiment of the use of transgenic fish larvae of the present invention to analyze the estrogen-like activity of a test solution.
Figure 5:
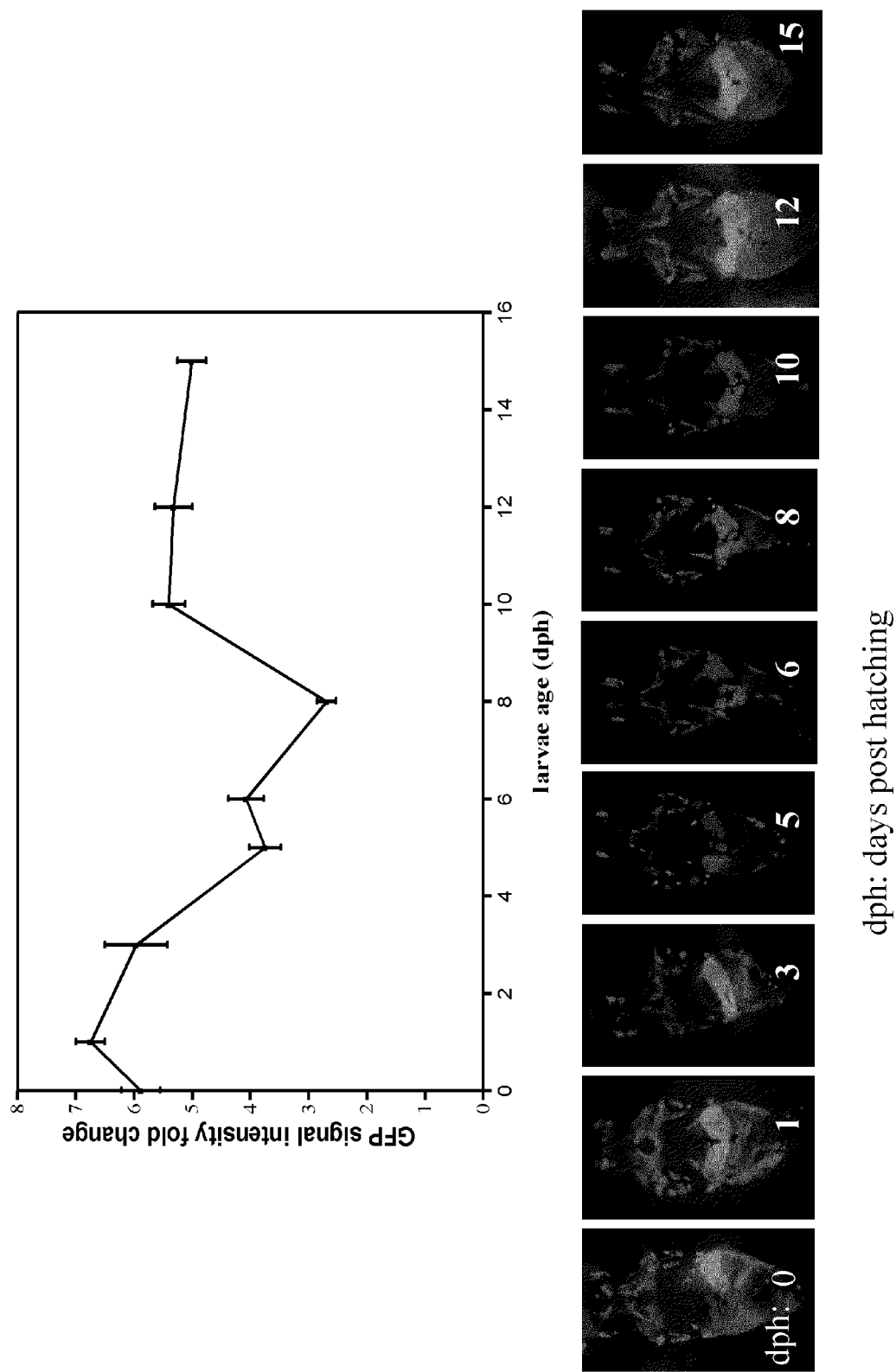
FIG. 5 depicts the estrogen sensitivity of transgenic fish larvae of varying days after fertilization.

A generalized exposure regimen is established in the present art. FIG. 4 presents an example of using transgenic fish larvae to analyze the estrogen-like activity of a test solution. Exposure of transgenic brackish medaka fish (preferably yolk-sac larvae fish) to test solution (containing estrogen or estrogenic substances) is performed at 28° C. The exposure usually takes 24-48 hours. After exposure, the fish will be deposited on the inner side of a petri-dish cover with a small drop of test solution left. The induced EGFP expression in the fish liver will be observed under fluorescence microscope. Yolk-sac larvae are small, exposure can be carried out in utensils like 96-well plate, 24-well plate, petri-dish and so on to save test reagents. Additionally, newly hatched larvae are the most transparent stage, and the transparence can keep up to 15 days after hatch. After 15 days, the larvae will be gradually less transparent due to the development of muscle. The transgenic fish larvae of 1 to 15 days after hatch have similar estrogen sensitivity (FIG. 5).

In response to different concentrations of estrogen or estrogen-like chemical substances, transgenic fish expresses varying quantity of EGFP protein which is presented as varying GFP signal intensity under fluorescence microscope. GFP signal intensity increases with estrogen or estrogen-like chemical substances as long as these substances do not reach the concentration to cause lethal toxicity. To quantify the estrogen-like activity of test solution, fluorescent image of fish liver is recorded using a camera connected with the fluorescence microscope. Liver GFP signal intensity can then be measured using some image analysis software such as Metamorph (Universal Imaging). To reduce the interference of fish autofluorescence, only fish liver area was selected for the analysis. The average signal intensity of the manually marked area calculated using the same software was regarded as GFP signal intensity. Fish liver photos recorded using the same image parameter setting can be compared directly using GFP signal intensity, those photos recorded using varying image parameter settings can also be compared as long as each group contain a common reference control.

Figure 6:
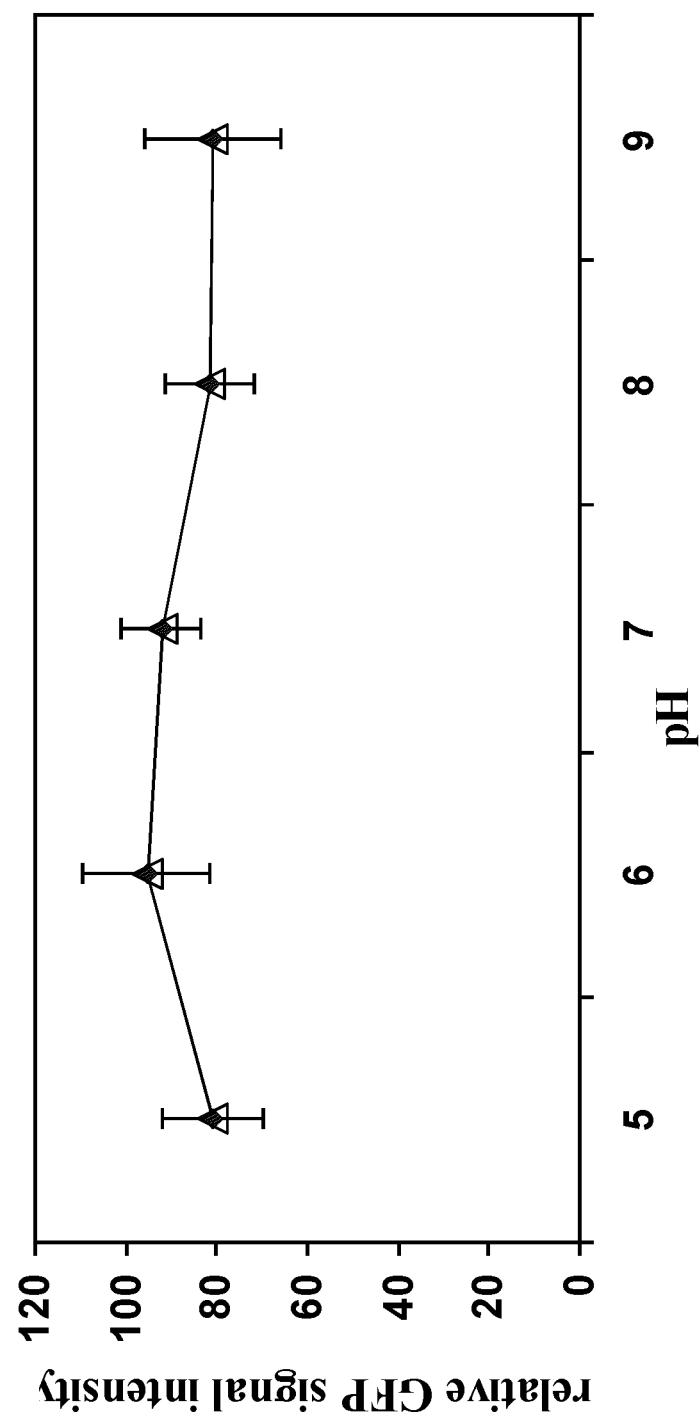
FIG. 6 is a graph showing that pH ranging from 5 to 9 does not affect the response of transgenic fish larvae to 17β-estradiol.
Figure 7:
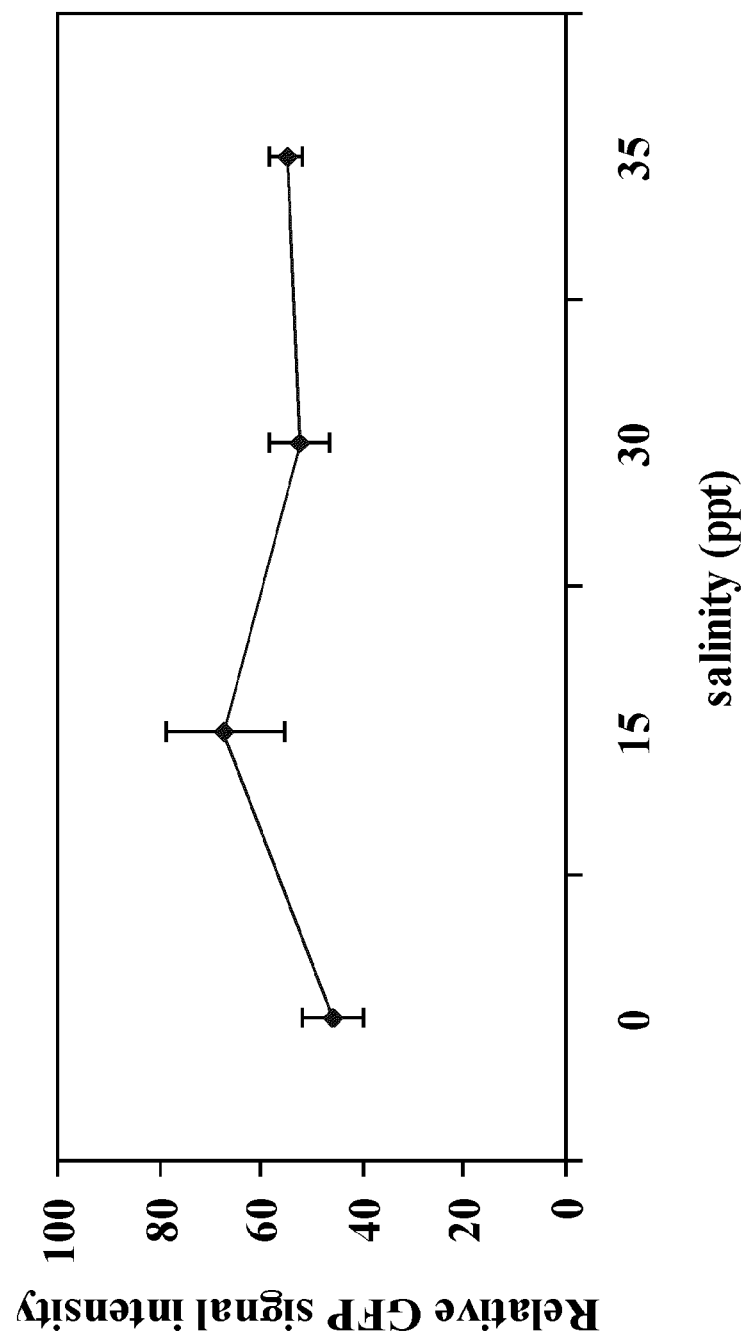
FIG. 7 is a graph showing that salinity ranging from 0 to 35 ppt does not affect the response of transgenic fish larvae to 17β-estradiol.

Considering environmental water samples and other test regents may have varying salinity and pH values, the effects of different salinity and pH on the sensitivity of transgenic brackish medaka fish to estrogen was investigated. Water of different pH values (e.g., 6.0, 7.0, 8.0 and 9.0) or different salinities (e.g., <5 ppt, fresh water; 15 ppt, brackish water; 30 ppt, common marine water; and 35 ppt, high salinity marine water) was used as test solution, into which the same concentration of estrogen (e.g., 5.1 nM) was added. Newly hatched transgenic brackish medaka fish are exposed to these solutions for a period of time (e.g., 24 hours). Fish livers are recorded and their GFP signal intensity were measured as previous described. Statistical analysis of estrogen induced liver GFP signal intensity proved that neither different pH (ranging from 6.0 to 9.0; FIG. 6) nor different salinity (ranging from 0 to 35 ppt; FIG. 7) affected the sensitivity of this transgenic brackish medaka fish to monitor estrogen-like activity.

Example 3

Estrogen-Like Activity Analysis

Natural Estrogens

Figure 8:
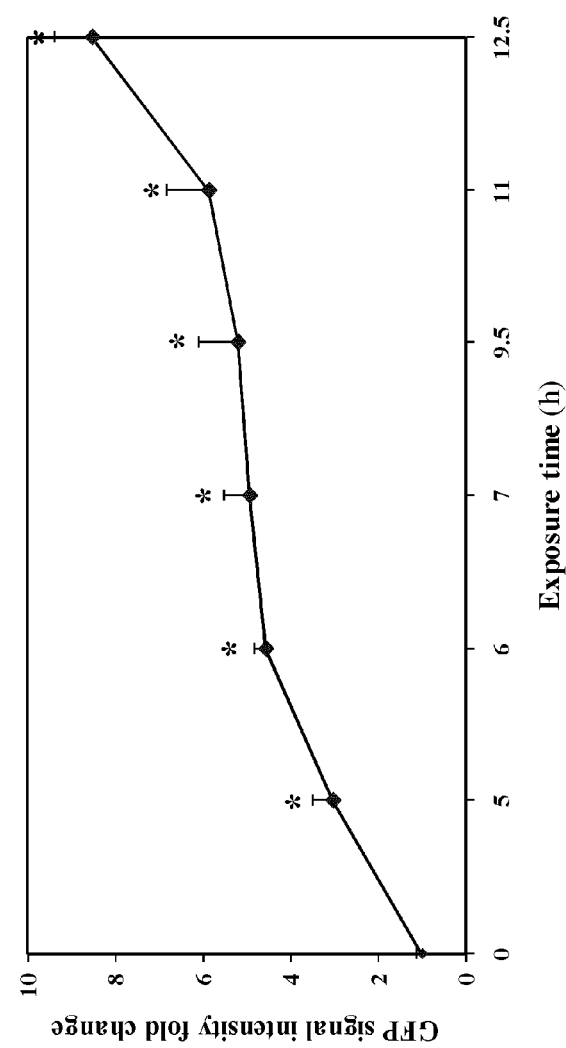
FIG. 8 depicts a time-lapse increase of GFP signal intensity in transgenic larvae in response to estrogen.
Figure 8:
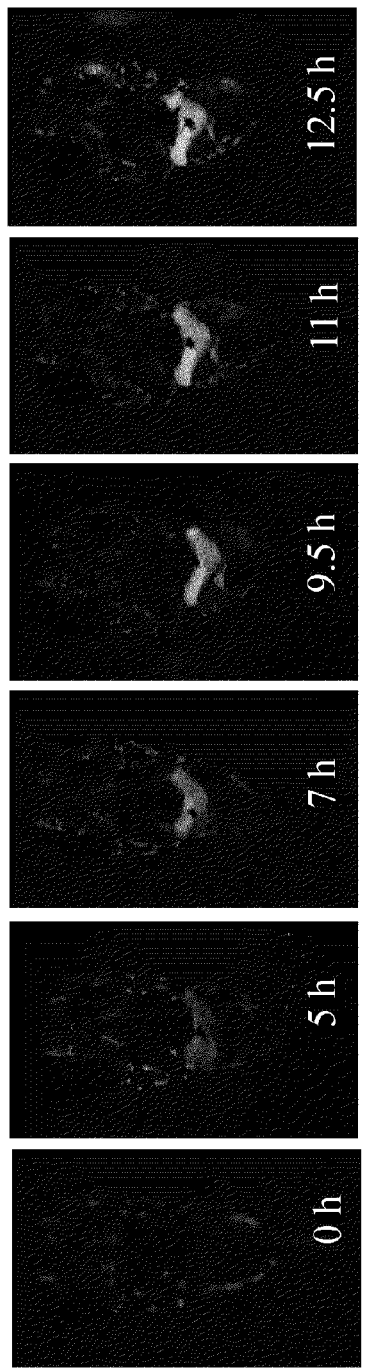
Figure 9:
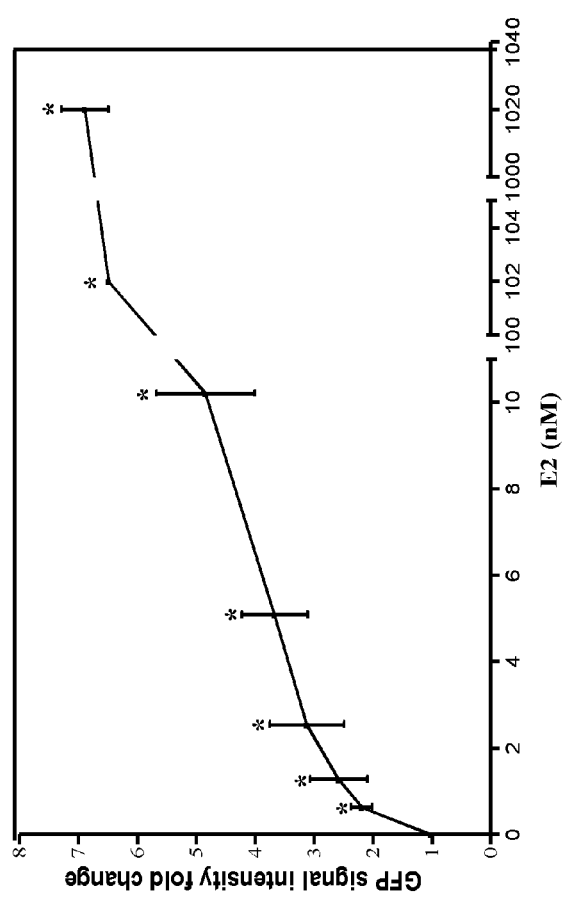
FIG. 9 depicts a dose-response of transgenic fish larvae to 17β-estradiol.
Figure 9:
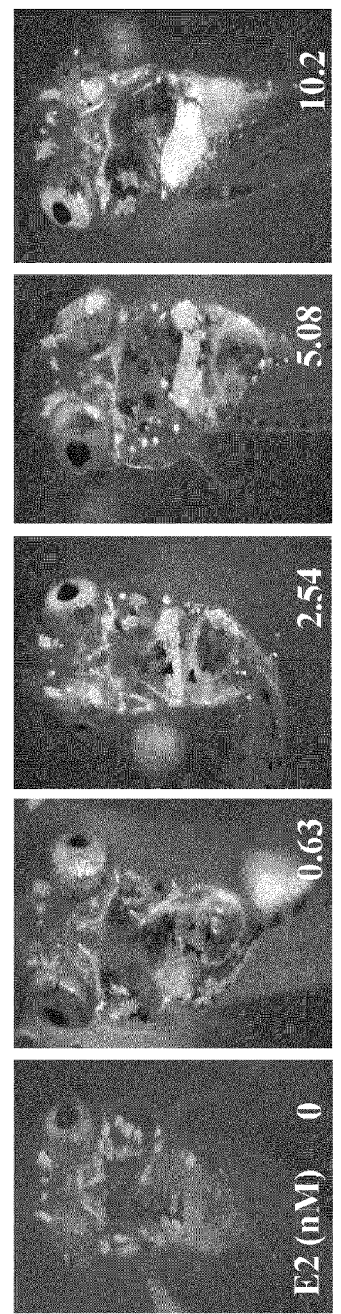

Estrone (E1), 17β-estradiol (E2) and estriol (E3) are natural steroid estrogens. All the three estrogens can induce liver GFP expression in transgenic brackish medaka larvae of present invention at nM level. Of them, E2 has been intensively studied, and is commonly used as a standard estrogen to evaluate the estrogen-like activity of testing reagents. Using transgenic larvae of present invention, induced GFP signal by E2 can usually be observed within 24 hours, and the GFP signal increases with the increasing concentration of E2. At higher E2 concentrations (e.g., 102 or 1020 nM), induced GFP signal intensity can even be observed within 4 hours after onset of exposure, and the signal increases with exposure time (FIG. 8), and reaches saturation within 24 hours. At low E2 concentrations, however, it will take longer for the induced GFP signal to accumulate to become detectable. Thus, by exposing transgenic brackish medaka fish larvae to different concentrations of E2 for a period of time (such as 24 hours), imaging the GFP expressing liver, and then measuring the induced liver GFP signal intensity using image analysis software, a standard curve correlating GFP signal intensity and E2 concentration can be established (GFP-E2 standard curve; FIG. 9). Using the same regimen, and also include one known E2 concentration exposure as reference, the estrogen-like activity of test reagents can then be evaluated as estrogen potency equivalent by referring the induced liver GFP signal to that of GFP-E2 standard curve.

Synthetic Estrogens

Figure 10:
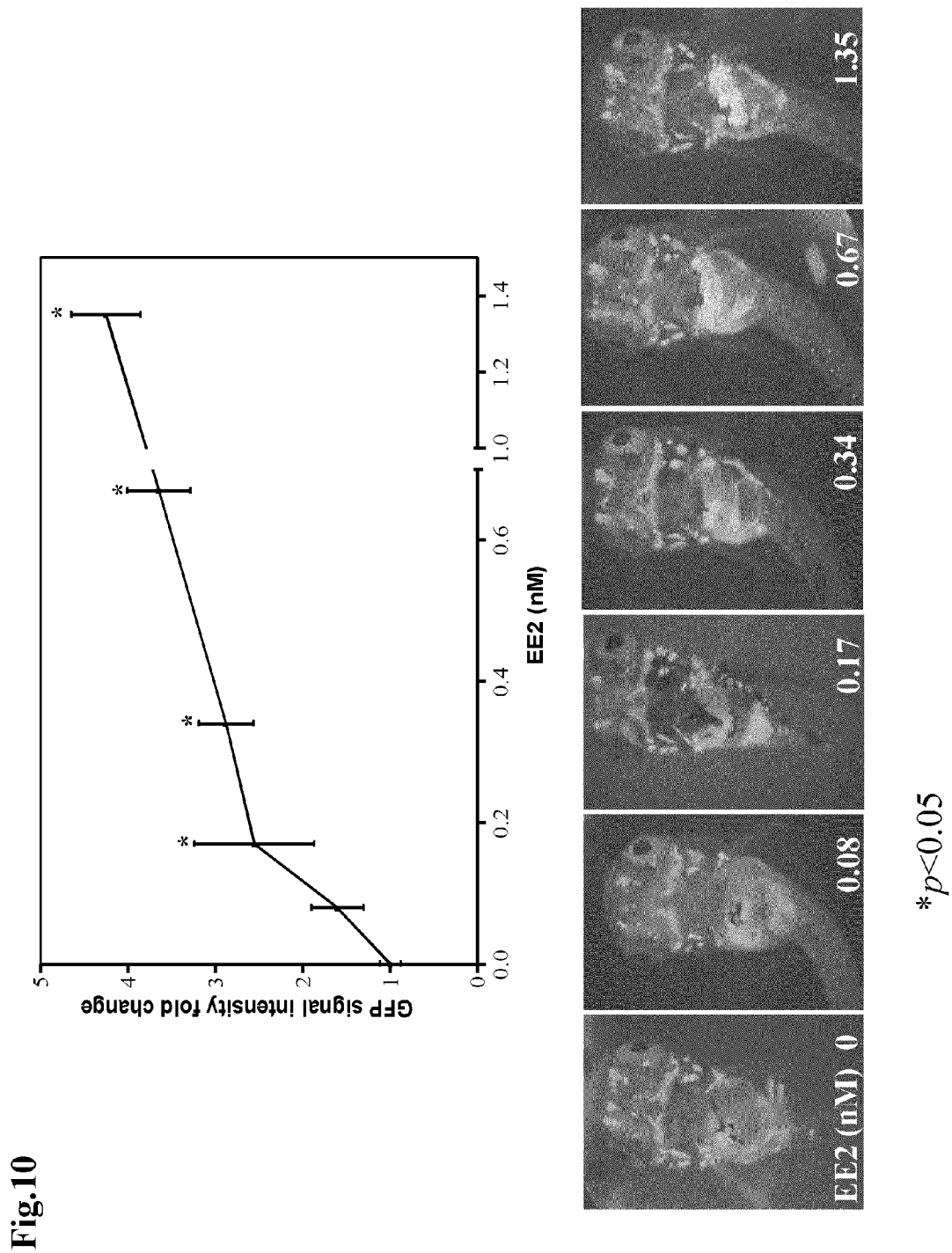
FIG. 10 depicts the dose-response of transgenic fish larvae to synthetic hormone 17α-ethinylestradiol.

17α-ethinylestradiol (EE2) and ethinylestradiol 3-methyl ether, the active compounds of contraceptive pills, are synthetic estrogens. EE2 has been widely studied and the estrogenic activity of which is even stronger than that of E2 (K. Kurauchi et al., Environ. Sci. Technol. 39(8):2762-8 (2005); J. Legler et al., Environ. Technol. 36: 4410-4415 (2002); see FIG. 9 and FIG. 10). By exposing the transgenic larvae fish to the same concentration (e.g. in nM) of EE2 and ethinylestradiol 3-methyl ether for the same period of time (e.g. 24 hours), the induced liver GFP signal is almost the same between EE2 and ethinylestradiol 3-methyl ether, which are stronger than that induced by E2. FIG. 10 depicts the dose-dependent response of the liver GFP signal of present invention to EE2.

Soymilk Phytoestrogens

Figure 11:
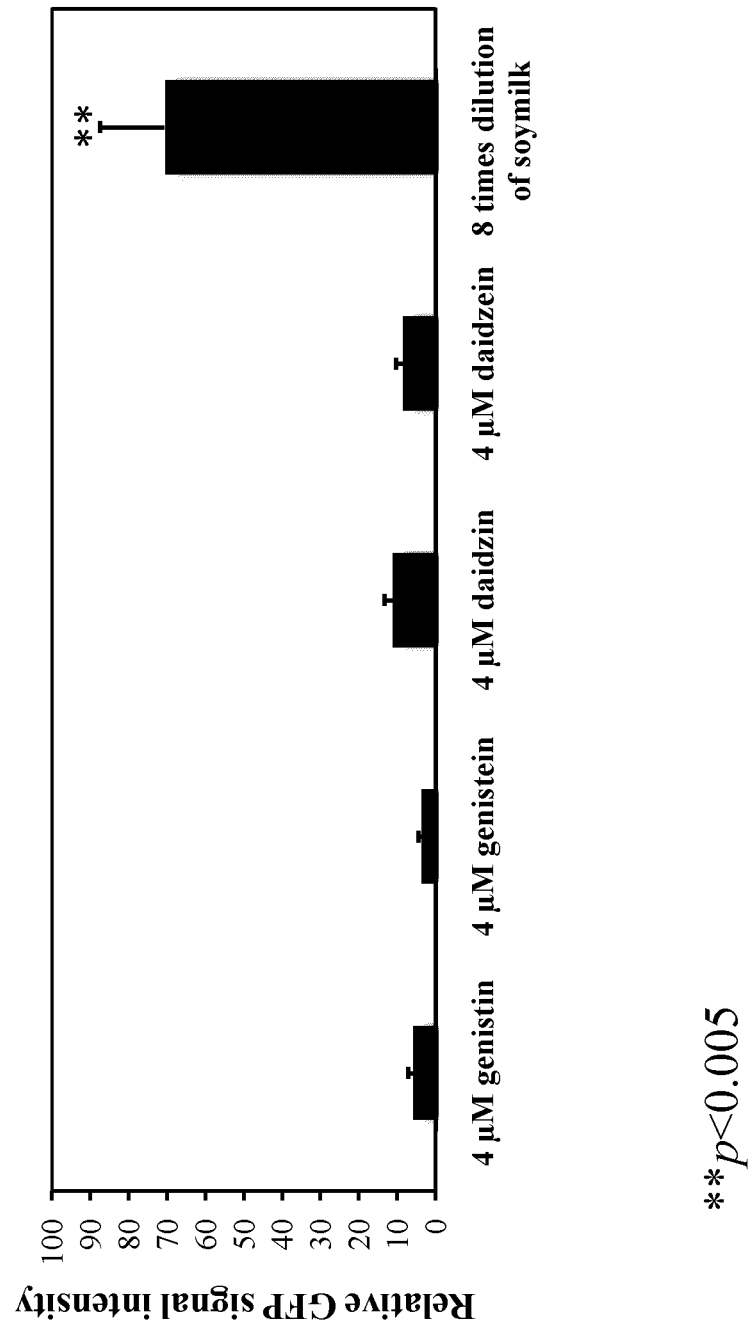
FIG. 11 depicts the liver GFP signal induced by phytoestrogens genistein, genistin, daidzein, and daidzin separately and their combination extracted from soymilk.

Soymilk contains high concentration of phytoestrogens such as genistein, genistin, daidzein and daidzin. Daily consume soymilk is claimed to be good for the health of humans, especially peri- and postmenopausal women, in many aspects (E Lydeking-Olsen et al. Eur J. Nutr. 43(4): 246-257 (2004); M S Kurzer. J. Nutr. 133: 1983S-1986S (2003)). As phytoestrogens like genistein, genistin, daidzein and daidzin are weak estrogens, previous transgenic fish study tried but failed to detect the estrogen activity of genistein (S Scholz et al. Environ Toxicol Chem. 24(10): 2553-2561 (2005)). One recent study found that the estrogen-like activity of pure genistein or genistein in combination with daidzein was not as strong as soymilk (G Rando et al. Toxicol Appl Pharmacol. 237(3): 288-297 (2009)). As pharmaceutical effects of soymilk depends on its estrogen-like activity, it is important to measure the estrogen-like activity of soymilk. Using transgenic medaka larvae fish of present invention, weak GFP signal can be observed in the liver after exposing the larvae to these four phytoestrogens separately at high concentrations for a period of time (e.g. 48 hours). To test the estrogen-like activity of soymilk, phytoestrogens in the soymilk will be firstly extracted out according to procedures we established. Briefly, soymilk is freeze dried and its phytoestrogens are extracted out using methanol. Extract solution is then water evaporated to dryness and phytoestrogens are redissolved in methanol. The concentration of each phytoestrogen can then be quantified by HPLC (high-performance chromatography), and the estrogen-like activity of extracted phytoestrogens can be easily evaluated by measuring induced GFP signal intensity in transgenic fish larvae after exposure to their dilution in water. We found different brand of soymilk has varying estrogen-like activity, and the estrogen-like activities of most soymilks are higher than that of any of the four phytoestrogens alone (e.g., FIG. 11).

Industrial Estrogenic Endocrine Disruptors 4-nonylphenol (NP) and bisphenol A (BPA) are well-known endocrine disruptors originated during industry activities. They can mimic estrogen to induce the expression of estrogen-responsive genes such as estrogen receptor, vitellogenin and choriogenin genes (C. Lee et al., J Health Sci, 48(5): 441-445 (2002)). Our previous study also showed that these two chemicals can induce the expression of choriogenin genes in the host organism of present invention (*Oryzias melastigma*) (X. Chen et al. Ectoxicol. Environ. Saf. 71:200-

208 (2008)). The detection of NP (K. Kurauchi et al., Environ Sci Technol, 39: 2762-2768 (2005)) and BPA (but not NP, Z. Zeng et al., Environ Sci Technol, 39: 9001-9008 (2005)) using transgenic fish have been reported. These two chemicals can also induce GFP expression in the transgenic fish of the present invention.

Cosmetic Estrogenic Chemicals

Figure 12:
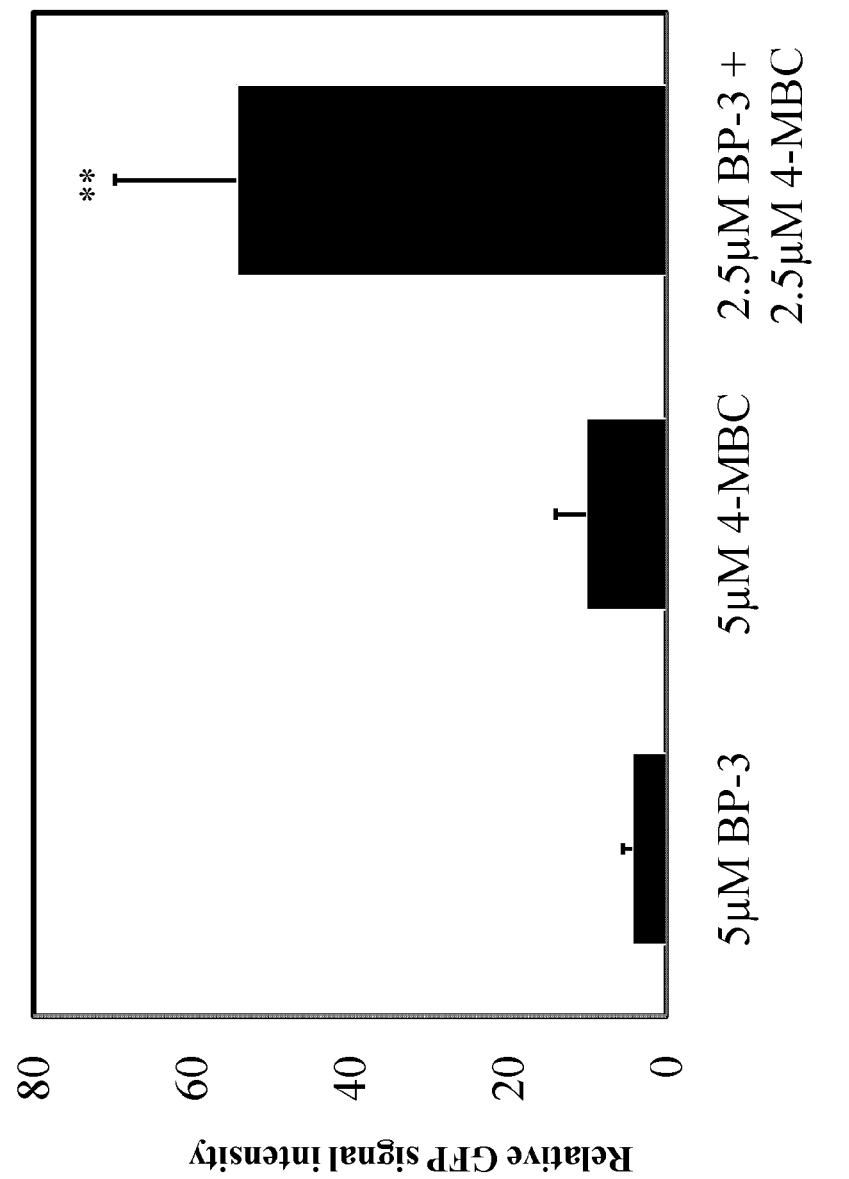
FIG. 12 depicts the liver GFP signal induced by UV filters BP-3 and 4-MBC separately and in combination. Transgenic fish larvae of one embodiment of the present invention are exposed to 4-MBC (5 μM), HMS (5 μM) and the combination of these two compounds mixed at their half concentrations (2.5 μM). The GFP signal induced by their mixture is significantly higher than that of these two compounds.
Figure 13:
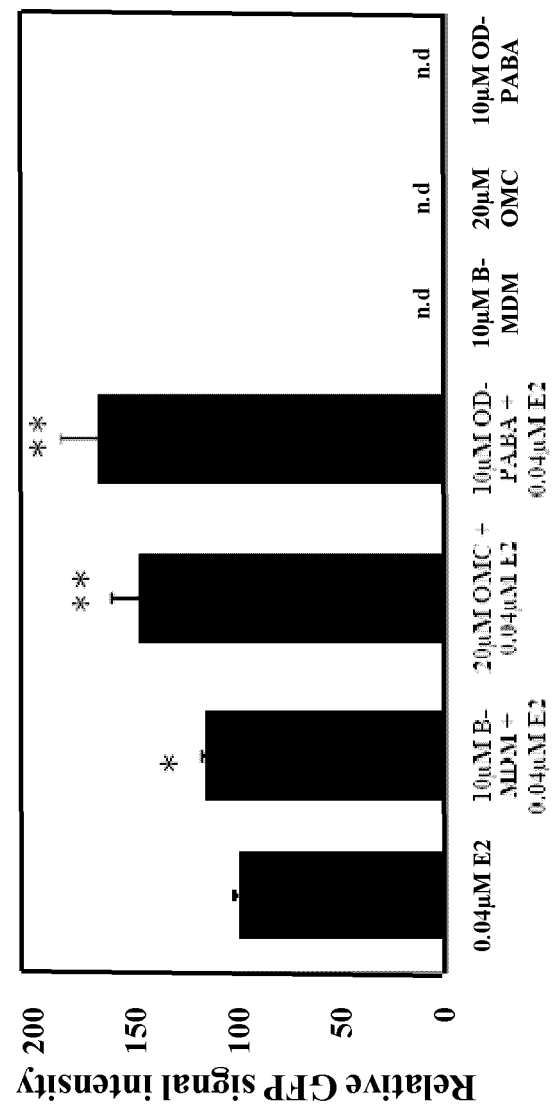
FIG. 13 depicts the liver GFP signal induced by 17β-estradiol alone or in combination with UV filters B-MDM, OMC or OD-PABA.
Figure 14:
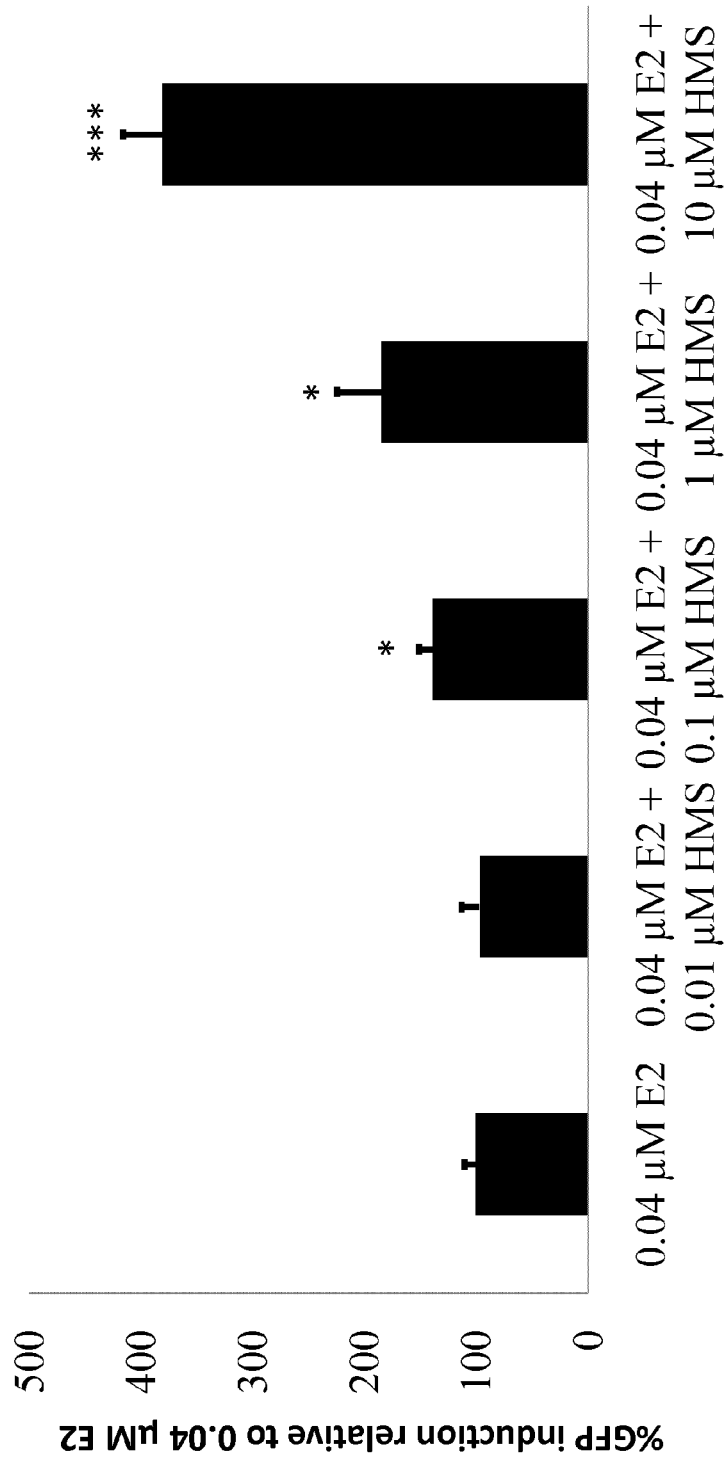
FIG. 14 shows that the liver GFP signal induced by 17β-estradiol can be increased by HMS in a close-dependent manner.

Benzophenone-3 (BP3), 3-(4'-methylbenzylidene-camphor) (4-MBC), homosalate (HMS), octyl dimethyl PABA (OD-PABA), 4-tert-Butyl-4'-methoxydibenzoylmethane (BMDM) and octyl-methoxycinnamate (OMC) are the most commonly used UV blockers in sun creams and cosmetics including lipsticks, skin lotions, hair dyes, shampoos and numerous other products like moldings, jet ink, tires and fabric. Generally, high percentages of UV filters (e.g. up to 10% for BP-3 and 6% for 4-MBC, NR Janjua et al., J Eur Acad Dermatol Venereol. 22(4):456-61 (2008)) are added in the products and a growing use of combinations of different UV filters for absorbing UVA, UVB and UVC light. UV filters enter human blood soon after application (NR Janjua et al., J Eur Acad Dermatol Venereol. 22(4):456-61 (2008)), and present in breast milk of women who used products containing cosmetic UV filters (M Schlumpf et al., Int J Androl, 31(2): 144-151 (2008)). Recent studies showed that many UV filters exhibit estrogenic activity by inducing estrogen receptors (P Y Kunz & K Fent. Toxicol Appl Pharmacol. 217(1): 86-99 (2006); P Y Kunz & K Fent. Toxicol Appl Pharmacol. 234(1): 77-88 (2009). However, study using transgenic zebrafish failed to detect the estrogen-like activity of UV filters (R Schreurs et al. Arch Toxicol. 76: 257-261 (2002)). Using transgenic *O. melastigma* larvae of present invention, we found BP-3 and 4-MBC can induce GFP expression in the liver after some period of exposure (e.g. 24 hours) at concentration higher than 0.65 µM, and the estrogenic activity of BP-3 and 4-MBC mixture is significantly higher than that of these two compounds separately (FIG. 12). Though compounds BMDM, OMC, OD-PABA and HMS, cannot induce the GFP expression in the liver of transgenic *O. melastigma* larvae, the estrogen agonism of BMDM, OMC and OD-PABA can be easily identified by binary exposure with E2 (FIG. 13), and HMS can enhance the estrogenic activity of 17β-estradiol in a dose-dependent manner (FIG. 14).

Example 4

Anti-Estrogen Activity Analysis

Figure 15:
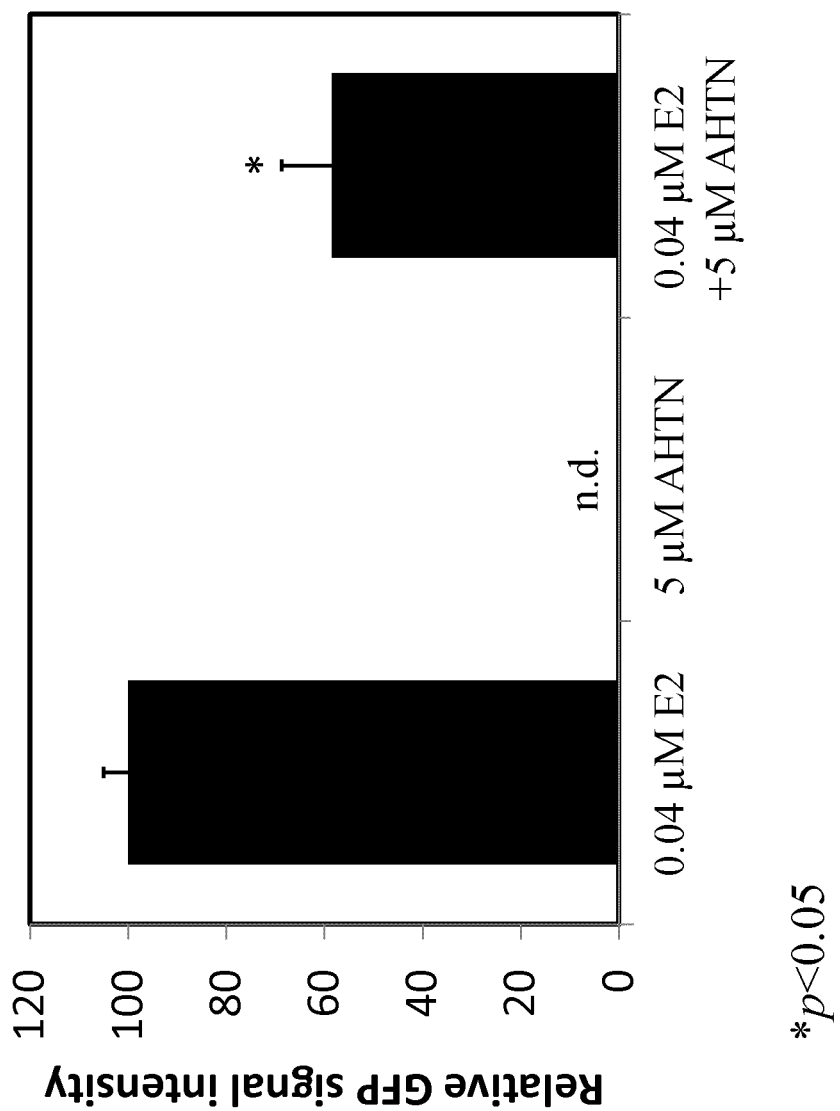
FIG. 15 shows that the liver GFP signal induced by 17β-estradiol can be decreased by polycyclic musk AHTN.

Polycyclic Musk 6-acetyl-1,1,2,4,4,7-hexamethyltetraline (AHTN) is one of the most widely used polycyclic musk. This compound is used as a fragrance ingredient in cosmetics and household cleaning products. According to HERA Risk Assessment reports in 2004, AHTN is produced in an annual volume of 1000 to 5000 tons in one Netherland and UK plant, respectively. According to HERA Risk Assessments, AHTN is not toxic to humans basing on present daily consumption. However, the ubiquitous distribution, high accumulation in environment (A Peck et al. Environ Sci Technol. 40: 5629-5635 (2006)), and bioaccumulation in organisms including human beings (H Nakata et al. Environ Sci Technol. 41: 2216-2222 (2007); S Lignell et al. Environ Sci Technol. 42: 6743-6748 (2008)) raise the concern of scientists. AHTN is found to be estrogen antagonist (RHMM Schreurs et al. Environ Sci Technol. 38: 997-1002 (2004); RHMM Schreurs et al. Toxicol Sci. 83: 264-272 (2005)). The estrogen antagonist activity of AHTN can also be very easily evaluated using transgenic medaka fish of present invention. Just expose transgenic medaka fish larvae to E2 (e.g. 0.04 µM) or E2 incombination with AHTN (e.g. 5 µM) for a period of time (e.g. 24 hours), and then measure the GFP signal intensity induced by E2 with/without the presence of AHTN. The weaker GFP signal induced by E2 in the presence of AHTN indicates this chemical is an estrogen antagonist (FIG. 15).

Example 5

Application of Transgenic *Oryzias Melastigma* Fish to Study Liver Regeneration

Liver plays a central role in metabolic homeostasis by metabolism, synthesis, storage and redistribution of nutrients, carbohydrate, fats and vitamins. At the same time, liver is also the main detoxifying organ of the body through removing waste and xenobiotics by metabolic conversion and biliary excretion. The liver of higher vertebrate, including humans, can precisely regulate its growth and mass and possess high capacity to regenerate after injury. A recent study revealed that fish liver also regenerates after partial hepatectomy in a manner highly similar to that described for mammals (NG Kan et al. FASEB J. fj.09-131730v1 (2009)). As fish share most developmental pathways, physiological and mechanisms and organ systems with humans (AR Cossins and DL Crawford. Nature Rev Genet. 6: 324-333 (2005)), using fish as a model organism for liver regeneration studies may help to understand the molecular and cellular mechanisms underlying liver regeneration. Using transgenic *O. melastigma* fish of present invention, which contains GFP marker for hepatocyte in response to estrogenic endocrine disruptors, will be very useful to reveal the effects of different estrogenic endocrine disruptors on liver regeneration.

Injuries caused by partial hepatectomy of a whole lobe, partial lobe and small scratch surgeries are performed by using protocols employed in previous zebrafish liver regeneration study (N G Kan et al. FASEB J. fj.09-131730v1 (2009)). To study liver regeneration, transgenic adult fish of present invention will be used. Briefly, adult medaka fish are starved for one day and anesthetized in 0.015% tricaine solution before surgery. Fish ventral body is then opened by a 3-4 mm incision and ventral liver lobe is carefully pulled out of the peritoneal cavity and resected at the very base of the lobe with special care. For partial lobe resection and surface scratch surgeries, the ventral lobe is exposed and a small piece of liver tip tissue or a small scratch is introduced using sharp forceps. The remaining liver is then placed back carefully into the peritoneal cavity and the body wall is closed with GLUture (Abbott Laboratories). The fish is then placed into fresh water for recovery. Sham-treated fish are also subjected to the same procedure excluding liver resection.

To analyze the effects of endocrine disruptors on liver regeneration process, fish will be treated with/without E2 or other endocrine disruptor(s). Parameters such as whole fish and liver weight are recorded, and liver shape is also recorded depending on its GFP signal using confocal microscope, and its volume can be measured using image analysis software (e.g. Metamorph, Universal Imaging).

Liver morphology changes during liver regeneration is also investigated. Fish liver at different stages of regeneration are dissected out and fixed in 4% paraformaldehyde (PFA)/phosphate-buffered saline (PBS) at 4° C. overnight, washed with PBS containing 0.1% Tween 20, pre-soaked in O.C.T. medium (Tissue Tek) for two hours and then embedded in O.C.T. and frozen at −80° C. for more than 3 h before sectioned at 10 μM thickness using Leica cryostat. Immunohistochemical staining of sections are performed according to standard protocols. Antibodies such as anti-proliferating cell nuclear antigen (PCNA), anti-prox1, anti-β-catenin and anti-tubulin are included.

Metabolomic and proteomic alteration of liver hepatocyte are also investigated to understand liver regeneration and the effects of endocrine disruptors on liver regeneration mechanisms. Fish recovering from partial hepatectomy are deeply anesthetized in tricaine solution and livers are dissected and incubated in 0.25% trypsin/PBS solution for 5 min. The liver is triturated to single-cell suspension by gentle pipetting and collected by centrifugation (1000 g, 7 min). Cell suspension is processed to flow cytometry and GFP-labeled hepatocytes are collected and protein extraction is performed according to standard protein extraction protocol. Extracted protein is then separated using NuPAGE Novex Bis-Tris Gels (Invitrogen) at 200V for 15 min, and stained with Colloidal Blue Kit (Invitrogen). Protein bands are cut out and destained with destaining solution (60% water, 30% methanol and 10% acetic acid). After dried in a Speed Vac (Savant), the gel is digested with Trypsin Profile IGD Kit (Sigma). The trypsinized protein digests are dried by Speed Vac and resuspend in 0.1% Formaic Acid in water. Peptides are analyzed by HPLC-MS/MS (HPLC: high-performance liquid chromatography, DIONEX Ultimate 300 system; MS/MS: tandem mass spectrometry, BRUKER MicrOTOF-QII). Additionally, iTRAQ (Isobaric tag for relative and absolute quantitation) technique is employed for protein quantitative analysis. The iTRAQ analysis is carried out according to published Nature Protocol (RY Tweedie-Cullen and M Livingstone-Zatchej. Nat. Proc. DIO: 10.1038/nprot.2008.89 (2008)). As a supportive technique, 2-dimension Fluorescence Difference Gel Electrophoresis (2-D DIGE) is also used to analyze the proteomic changes of hepatocytes during liver regeneration. This analysis is performed according to a Nature Protocol (N S Tannu and S E Hemby. Nat Protoc. 1(4): 1732-1742 (2006)).

From the foregoing, although specific embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

REFERENCES

Citation of a reference herein shall not be construed as an admission that such reference is prior art to the present invention. All references cited herein are hereby incorporated by reference in their entirety. Below is a listing of references cited herein:

Legler J, Van den Brink C E, Brouwer A, Murk A J, Van der Saag P T, Vethaak A D, Van der Burg B. Development of a stably transfected estrogen receptor-mediated luciferase reporter gene assay in the human T47D breast cancer cell line. Toxicol Sci, 1999, 48: 55-66.

Chen X, Li V W, Yu R M, Cheng S H. Choriogenin mRNA as a sensitive molecular biomarker for estrogenic chemicals in developing brackish medaka (Oryzias melastigma). Ecotoxicol Environ Saf, 2008, 71: 200-208.

Chen X, Li L, Wong C K C, Cheng S H. Rapid adaptation of molecular resources from zebrafish and medaka to develop an estuarine/marienmodel. Comp Biochem Physiol C Toxicol Pharmacol, 2009, 149: 647-655.

Ekker S C, Stemple D L, Clark M, Chien C B, Rasooly R S, Javois L C. Zebrafish genome project: bringing new biology to the vertebrate genome field. Zebrafish, 2007, 4: 239-251.

Kasahara M, Naruse K, Sasaki S, Nakatani Y, Qu W, Ahsan B, Yamada T, Nagayasu Y, Doi K, Kasai Y, Jindo T, Kobayashi D, Shimada A, Toyoda A, Kuroki Y, Fujiyama A, Sasaki T, Shimizu A, Asakawa S, Shimizu N, Hashimoto S, Yang J, Lee Y, Matsushima K, Sugano S, Sakaizumi M, Narita T, Ohishi K, Haga S, Ohta F, Nomoto H, Nogata K, Morishita T, Endo T, Shin I T, Takeda H, Morishita S, Kohara Y. The medaka draft genome and insights into vertebrate genome evolution. Nature, 2007, 447: 714-719.

Inoue K, Takei Y. Diverse adaptability in oryzias species to high environmental salinity. Zool Sci, 2002, 19: 727-734.

Naruse K. Classification and phylogeny of fishes of the genus Oryzias and its relatives. Fish Biol J Medaka, 1996, 8: 1-9.

Ozato K, Kondoh H, Inohara H, Iwamatsu T, Wakamatsu Y, Okada T S. Production of transgenic fish: introduction and expression of chicken .delta.-crystallin gene in medaka embryos. Cell Differ, 1986, 19: 237-244.

Inoue K, Ozato K, Kondoh H, Iwamatsu T, Wakamatsu Y, Fujita T, Okada T S. Stage-dependent expression of the chicken δ-crystallin gene in transgenic fish embryos. Cell Differ Dev, 1989, 27: 57-68.

Inoue K, Yamashita S, Hata J, Kabeno S, Asada S, Nagahisa E, Fujita T. Electroporation as a new technique for producing transgenic fish. Cell Differ Dev, 1990, 29(2): 123-128.

Tamiya E, Sugiyama T, Masaki K, Hirose A, Okoshi T, Karube I. Spatial imaging of luciferase gene expression in transgenic fish. Nucleic Acids Res, 1990, 18(4): 1072.

Lu J K, Chen T T, Chrisman C L, Andrisani O M, Dixon J E. Integration: expression, and germ-like transmission of foreign growth hormone genes in medaka (Oryzias latipes). Mol Mar Biol Biotechnol, 1992, 1(4/5): 366-375.

Tsai H J, Wang S H, Inoue K, Takagi S, Kimura M, Wakamatsu Y, Ozato K. Initiation of the transgenic lacZ gene expression in medaka (Oryzias latipes) embryos. Mol. Mar Biol Biotechnol, 1995, 4(1): 1-9.

Winn R N, Van Beneden R J, Burkhart J G. Transfer, Methylation and Spontaneous Mutation Frequency of ΦX174am3cs70 sequences in Medaka (Oryzias latipes) and Mummichog (Fundulus heteroclitus): Implications for Gene Transfer and Environmental Mutagenesis in Aquatic Species. Marine Environ Res, 1995, 40(3): 247-265.

Cossins A R, Crawford D L. Fish as models for environmental genomics. Nature Rev Genet, 2005, 6: 324-333.

Sumpter J P, Xenoendocrine disrupters—environmental impacts. Toxicol Lett, 1998, 102-103: 337-342.

Kawamura T, Sakai S, Omura S, Hori-e R, Kawahara T, Kinoshita M, Yamashita I. Estrogen inhibits development of yolk veins and causes blood clotting in transgenic medaka fish over expressing estrogen receptor. Zoolog Sci, 2002, 19(12): 1355-61.

Ueno T, Yasumasu S, Hayashi S, Iuchi I. Identification of choriogenin cis-regulatory elements and production of estrogen-inducible, liver-specific transgenic Medaka. Mech Dev, 2004, 121(7-8): 803-15.

Kurauchi K, Nakaguchi Y, Tsutsumi M, Hori H, Kurihara R, Hashimoto S, Ohnuma R, Yamamoto Y, Matsuoka S, Kawai S, Hirata T, Kinoshita M. In vivo visual reporter system for detection of estrogen-like substances by transgenic medaka. Environ Sci Technol, 2005, 39(8): 2762-8.

Zeng Z, Shan T, Tong Y, Lam S H, Gong Z. Development of estrogen-responsive transgenic medaka for environmental monitoring of endocrine disrupters. Environ Sci Technol, 2005, 39(22): 9001-8.

Hano T, Oshima Y, Kinoshita M, Tanaka M, Mishima N, Ohyama T, Yanagawa T, Wakamatsu Y, Ozato K, Honjo T. *Quantitative bioimaging analysis of gonads in olvas-GFP/ST-II YI* Medaka (transgenic *Oryzias latipes*) exposed to ethinylestradiol. Environ Sci Technol, 2007, 41(4): 1473-9.

Salam M A, Sawada T, Ohya T, Ninomiya K, Hayashi S. Detection of environmental estrogenicity using transgenic medaka hatchlings (*Oryzias latipes*) expressing the GFP-tagged choriogenin L gene. J Environ Sci Health A Tox Hazard Subst Environ Eng, 2008, 43(3): 272-7.

Legler J, Broekhof J L M, Brouwer A, Lanser P H, Murk A J, van der Saag P T, Vethaak A D, Wester P, Zivkovic D, van der Burg B. A novel in vivo bioassay for (xeno-)estrogens using transgenic zebrafish. Environ Sci Technol, 2000, 34: 4439-4444.

Legler J. Zeinstra L M, Lanser P H, Bogerd J, Brouwer, Vethaak ADVoogt P D, Murk A J, van der Burg B. Comparison of in vivo and in vitro reporter gene assay for short-term screening of estrogenic activity. Environ Sci Technol, 2002, 36: 4410-4414.

Tong S K, Mouriec K, Kuo M W, Pellegrini E, Gueguen M M, Brion F, Kah O, Chung B C. A cyp19alb-gfp (aromatase B) transgenic zebrafish line that expresses GFP in radial glial cells. Genesis, 2009, 47(2): 67-73.

Kinoshita M, Toyohara H, Sakaguchi M, Inoue K. A stable line of transgenic medaka (*Oryzias latipes*) carrying the CAT gene. Aquaculture, 1996, 143 (3-4): 267-276.

Tanaka M, Kinoshita M, Kobayashi D, Nagahama Y. Establishment of medaka (*Oryzias latipes*) transgenic lines with the expression of green fluorescent protein fluorescence exclusively in germ cells: A useful model to monitor germ cells in a live vertebrate. Proc Natl Acad Sci USA, 2001, 98 (5): 2544-2549.

Koprunner M, Thisse C, Thisse B, Raz E. A zebrafish nanos-related gene is essential for the development of primordial germ cells. Genes Dev, 2001, 15 (21): 2877-2885.

Kurokawa H, Aoki Y, Nakamura S, Ebe Y, Kobayashi D, Tanaka M. Time-lapse analysis reveals different modes of primordial germ cell migration in the medaka *Oryzias latipes*. Dev Growth Differ, 2006, 48 (3): 209-221.

Lee C, Jeon S H, Na J G, Choi Y J, Park K. Sensitive of mRNA expression of vitellogenin, choriogenin and estrogen receptor by estrogenic chemicals in medaka *Oryzias latipes*. J Health Sci, 2002, 48(5): 441-445.

Janjua N R, Kongshoj B, Andersson A M, Wulf H C. Sunscreens in human plasma and urine after repeated whole-body topical application. J Eur Acad Dermatol Venereol, 2008, 22(4): 456-61.

Schlumpf M, Durrer S, Faass O, Ehnes C, Fuetsch M, Gaille C, Henseler M, Hofkamp L, Maerkel K, Reolon S, Timms B, Tresguerres J A, Lichtensteiger W. Developmental toxicity of UV filters and environmental exposure: a review. Int J Androl, 2008, 31(2): 144-51.

Kunz P Y, Fent K. Estrogenic activity of UV filter mixtures. Toxicol Appl Pharmacol, 2006, 217(1): 86-99.

Kunz P Y, Fent K. Estrogenic activity of ternary UV filter mixtures in fish (*Pimephales promelas*)—an analysis with nonlinear isobolograms. Toxicol Appl Pharmacol, 2009, 234(1): 77-88.

Peck A M. Linebaugh E K Hornbuckle K C. Synthetic musk fragrances in Lake Erie and Lake Ontario sediment ores. Environ Sci Technol, 2006, 40: 5629-5635.

Lignell S. Darnerud P. Aune M. Cnattingius S. Hajslova J. Setkova L. Glnn A. Temporal trends of synthetic musk compounds in mother's milk and associations with personal use of perfumed products. Environ Sci Technol, 2008, 42: 6743-6748.

Kurzer M S. Phytoestrogen supplement use by women. J Nutr, 2003, 133: 1983S-1986S.

Lydeking-Olsen E, Beck-Jensen J E, Setchell K D, Holm-Jensen T. Soymilk or progesterone for prevention of bone loss—a 2 year randomized, placebo-controlled trial. Eur J Nutr, 2004, 43(4): 246-57.

Rando G, Ramachandran B, Rebecchi M, Clana P, Maggi A. Differential effect of pure isoflavones and soymilk on estrogen receptor activity in mice. Toxicol Appl Pharmacol, 2009, 237(3): 288-97.

Kan N G, Junghans D, Izpisua Belmonte J C. Compensatory growth mechanisms regulated by BMP and FGF signaling mediate liver regeneration in zebrafish after partial hepatectomy. FASEB J, 2009. fj.09-131730v1.

Cossins A R, Crawford D L, Fish as models for environmental genomics. Nature Rev let. 2005, 6: 324-333.

Tweedie-Cullen R Y, Livingstone-Zatchej M. Quantitative analysis of protein expression using iTRAQ and mass spectrometry. Nat Protoc, 2008, DIO: 10.1038/nprot.2008.89.

Tannu N S, Hemby S E. Two-dimensional fluorescence difference gel electrophoresis for comparative proteomics profiling. Nat Protoc, 2006, 1(4): 1732-1742.

What is claimed is:

1. An expression cassette comprising:
a reporter nucleotide sequence encoding a reporter protein;
an estrogen-responsive 5'-regulatory nucleotide sequence selected from the group consisting of SEQ ID NO:2, SEQ ID NO:3, and SEQ ID NO:4, wherein the regulatory nucleotide sequence is operably linked 5' to the reporter nucleotide sequence to induce expression of the reporter protein in the presence of estrogen or an estrogen-like compound; and
a 3'-regulatory region operably linked 3' to the reporter nucleotide sequence.

2. The expression cassette according to claim 1, wherein the reporter protein is an autofluorescent protein.

3. The expression cassette according to claim 2, wherein the autofluorescent protein is selected from the group consisting of an enhanced green fluorescent protein (EGFP), a green fluorescent protein (GFP), a blue fluorescent protein (BFP), a yellow fluorescent protein (YFP), and a red fluorescent protein (RFP).

4. The expression cassette according to claim 1, wherein the 3'-regulatory region comprises an mRNA polyadenylation signal.

5. The expression cassette according to claim 4, wherein the mRNA polyadenylation signal is the 3'-flanking region of a choriogenin H gene of a medaka fish selected from the group consisting of Oryzias melastigma and Oryzias latipes.

6. The expression cassette according to claim 5, wherein the 3'-flanking region of the choriogenin H gene comprises the 3'-UTR (untranslated region) and the polyadenylation tail sequences of the choriogenin H gene.

7. The expression cassette according to claim 1, wherein the 3'-regulatory region comprises the nucleotide sequence of SEQ ID NO:5.

8. A host cell transduced with the expression cassette according to claim 1.

9. A transgenic cell of an aquatic animal, said transgenic cell comprising at least one expression cassette according to claim 1.

10. The transgenic cell according to claim 9, wherein the aquatic animal is selected from the group consisting of an Oryzias species and a Danio species.

11. The transgenic cell according to claim 10, wherein the Oryzias species is selected from the group consisting of Oryzias melastigma and Oryzias latipes.

12. An expression cassette comprising:
a reporter nucleotide sequence encoding a reporter protein;
an estrogen-responsive 5'-regulatory nucleotide sequence isolated from a medaka fish, wherein the regulatory nucleotide sequence is operably linked 5' to the reporter nucleotide sequence to induce expression of the reporter protein in the presence of estrogen or an estrogen-like compound; and
a 3'-regulatory region operably linked 3' to the reporter nucleotide sequence, wherein the 3'-regulatory region comprises the nucleotide sequence of SEQ ID NO:5.

13. The expression cassette according to claim 12, wherein the 5'-regulatory nucleotide sequence is isolated from a brackish medaka fish of the species Oryzias melastigma.

14. The expression cassette according to claim 13, wherein the 5'-regulatory nucleotide sequence is derived from the promoter region of a choriogenin H gene of Oryzias melastigma, said choriogenin H gene having a nucleotide sequence of SEQ ID NO:1.

15. The expression cassette according to claim 12, wherein the reporter protein is an autofluorescent protein.

16. The expression cassette according to claim 15, wherein the autofluorescent protein is selected from the group consisting of an enhanced green fluorescent protein (EGFP), a green fluorescent protein (GFP), a blue fluorescent protein (BFP), a yellow fluorescent protein (YFP), and a red fluorescent protein (RFP).

17. A host cell transduced with the expression cassette according to claim 12.

18. A transgenic cell of an aquatic animal, said transgenic cell comprising at least one expression cassette according to claim 12.

19. The transgenic cell according to claim 18, wherein the aquatic animal is selected from the group consisting of an Oryzias species and a Danio species.

20. The transgenic cell according to claim 19, wherein the Oryzias species is selected from the group consisting of Oryzias melastigma and Oryzias latipes.

* * * * *